US010968536B2

(12) United States Patent
Brown et al.

(10) Patent No.: US 10,968,536 B2
(45) Date of Patent: Apr. 6, 2021

(54) METHODS AND COMPOSITIONS FOR SEQUENCING

(71) Applicants: JumpCode Genomics, Inc., Carlsbad, CA (US); The Scripps Research Institute, La Jolla, CA (US)

(72) Inventors: Keith Brown, Carlsbad, CA (US); Daniel R. Salomon, La Jolla, CA (US); Steven Head, La Jolla, CA (US); Azeem Siddique, La Jolla, CA (US); Phillip Ordoukhanian, La Jolla, CA (US)

(73) Assignees: JUMPCODE GENOMICS, INC., Carlsbad, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/553,495

(22) PCT Filed: Feb. 25, 2016

(86) PCT No.: PCT/US2016/019609
§ 371 (c)(1),
(2) Date: Aug. 24, 2017

(87) PCT Pub. No.: WO2016/138292
PCT Pub. Date: Sep. 1, 2016

(65) Prior Publication Data
US 2018/0237950 A1    Aug. 23, 2018

Related U.S. Application Data

(60) Provisional application No. 62/120,734, filed on Feb. 25, 2015.

(51) Int. Cl.
*C40B 40/08* (2006.01)
*C12N 15/10* (2006.01)

(52) U.S. Cl.
CPC .......... *C40B 40/08* (2013.01); *C12N 15/1093* (2013.01)

(58) Field of Classification Search
CPC ..................... C40B 40/08; C12N 15/1093
See application file for complete search history.

(56) References Cited

U.S. PATENT DOCUMENTS

| 2001/0031466 | A1 | 10/2001 | Malek |
| 2005/0255089 | A1 | 11/2005 | Chiorini et al. |
| 2006/0040297 | A1 | 2/2006 | Leamon et al. |
| 2006/0252060 | A1 | 11/2006 | Willis et al. |
| 2009/0036325 | A1 | 2/2009 | McKernan et al. |
| 2009/0098548 | A1 | 4/2009 | Ason et al. |
| 2009/0264299 | A1 | 10/2009 | Drmanac et al. |
| 2010/0287628 | A1 | 11/2010 | Ostertag et al. |
| 2012/0252015 | A1 | 10/2012 | Hindson et al. |
| 2012/0258892 | A1 | 10/2012 | Wang |
| 2013/0203605 | A1* | 8/2013 | Shendure ........... C12N 15/1093 506/2 |
| 2013/0315886 | A1 | 11/2013 | Gage et al. |
| 2014/0356867 | A1 | 12/2014 | Peter et al. |
| 2014/0357523 | A1 | 12/2014 | Zeiner et al. |
| 2015/0159174 | A1 | 6/2015 | Frendewey et al. |
| 2015/0225773 | A1 | 8/2015 | Farmer et al. |
| 2016/0034169 | A1 | 2/2016 | Brown et al. |
| 2016/0053304 | A1 | 2/2016 | Wurtzel et al. |
| 2016/0090622 | A1 | 3/2016 | Liu et al. |
| 2016/0376663 | A1 | 12/2016 | Brown et al. |
| 2018/0273933 | A1* | 9/2018 | Gunderson .......... C12Q 1/6869 |
| 2019/0153528 | A1 | 5/2019 | Brown |
| 2020/0181700 | A1 | 6/2020 | Brown et al. |

FOREIGN PATENT DOCUMENTS

| CN | 102439177 A | 5/2012 |
| JP | 2003508082 A | 3/2003 |
| WO | WO-9916908 A2 | 4/1999 |
| WO | WO-0000632 A1 | 1/2000 |
| WO | WO-2004081225 A2 | 9/2004 |
| WO | WO-2008134596 A2 | 11/2008 |
| WO | WO-2012048113 A2 | 4/2012 |
| WO | WO-2012061832 A1 | 5/2012 |
| WO | WO-2013176772 A1 | 11/2013 |
| WO | WO-2013191775 A2 | 12/2013 |
| WO | WO-2015002780 A1 | 1/2015 |
| WO | WO-2015131101 A1 | 9/2015 |
| WO | WO-2016022931 A1 | 2/2016 |

(Continued)

OTHER PUBLICATIONS

Brouns, S.J. Molecular biology. A Swiss army knife of immunity. Science 337(6069)808-9 (Aug. 17, 2012).
Carpenter, et al. Pulling out the 1%: Whole-Genome Capture for the Targeted Enrichment of Ancient DNA Sequencing Libraries. The American Journal of Human Genetics 93, 852-864, 2013.
Deltcheva, et al. CRISPR RNA maturation by trans-encoded small RNA and host factor RNase III. Nature. Mar. 31, 2011;471(7340):602-7. doi: 10.1038/nature09886.
Dolinsek, et al. Depletion of unwanted nucleic acid templates by selective cleavage: LNAzymes, catalytically active oligonucleotides containing locked nucleic acids, open a new window for detecting rare microbial community members. App. Environ Microbiol 79(5); 1534-1544 (Mar. 2013).
Gao, X et al. In vivo cancer targeting and imaging with semiconductor quantum dots, Nature Biotechnology, 22(8);969-976 (Jul. 18, 2004).

(Continued)

*Primary Examiner* — Robert H Havlin
(74) *Attorney, Agent, or Firm* — Wilson Sonsini Goodrich & Rosati

(57) ABSTRACT

Methods, compositions and kits are provided herein for insertional modification of nucleic acids by, for example transposase-mediated covalent insertion of insertion sequence into a sample nucleic acid molecule. Using sequence of the insertion to direct amplification of adjacent nucleic acid sequence, and using bar codes to map amplified sequence to partitions, one can map sample nucleic acid sequence to single molecules of the nucleic acid sample that are derived directly from the sample nucleic acid molecule.

10 Claims, 13 Drawing Sheets

(56) References Cited

FOREIGN PATENT DOCUMENTS

| WO | WO-2016100955 A2 | 6/2016 |
|---|---|---|
| WO | WO-2017015075 A1 | 1/2017 |
| WO | WO-2017218512 A1 | 12/2017 |
| WO | WO-2018114706 A1 | 6/2018 |

OTHER PUBLICATIONS

Nickitas-Etienne, Athina. International Application No. PCT/US2015/014242 International Preliminary Report on Patentability dated Aug. 9, 2016.

Moussaid, El Mostafa. International Application No. PCT/US2015/018115 International Preliminary Report on Patentability dated Aug. 30, 2016.

Copenheaver, Blaine R. International Application No. PCT/US2015/018115 International Search Report and Written Opinion dated May 29, 2015.

Young, Lee W. International Application No. PCT/US2015/8014242 International Search Report and Written Opinion dated Jul. 30, 2015.

Wezyk, Magdalena. International Application No. PCT/US2017/017530 International Search Report and Written Opinion dated May 15, 2017.

Jiang, W. et al. Demonstration of CRISPR/Cas9/sgRNA-mediated targeted gene modification in Arabidopsis, tobacco, sorghum and rice. Nucleic Acids Res. (Nov. 2013), 41(20):e188.

Jinek et al. A programmable dual-RNA-guided DNA endonuclease in adaptive bacterial immunity. Science 337:816-821 (2012).

Kolpashchikov, D. An Elegant Biosensor Molecular Beacon probe: Challenges and Recent Solutions, Scientifica 2012; 1-17 (Dec. 3, 2012) Article ID 928783.

Laurent, St G. III et al. A Line-1 component to human aging: do LINE elements exact a longevity cost for evolutionary advantage? Mechanisms of Ageing and Development, 131(5); 299-305 (May 1, 2010).

Lee, E. et al. Landscape of Somatic Retrotransposition in Human Cancers, Science 337(6097); 967-971 (Jun. 28, 2012) Supplement.

Li, W. et al. Activation of transposable elements during aging and neuronal decline in Drosophila, Nature Neuroscience 16(5);529-531 (Apr. 7, 2013).

Soriano, V. et al. Hepatitis C virus-RNA clearance in HIV-coinfected patients with chronic hepatitis C treated with pegylated interferon plus ribavirin. Antiviral Therapy, 9;505-509 (2004).

Terns, et al. CRISPR-based adaptive immune systems. Curr Opin Microbiol. Jun. 2011;14(3):321-7.

Vlad, Sc et al. Protective effects of NSAIDs on the development of Alzheimer disease. Neurology, 70(19); 1672-1677 (May 6, 2008).

Zhang, F. et al. CRISPR/Cas9 for genome editing: Progress, Implications and challenges. Human Molecular Genetics 23(R1):R40-R46 (Mar. 20, 2014).

European Patent Application No. 15754498.2 European Search Report dated Nov. 27, 2017.

Iskow, Rebecca C. et al. Natural Mutagenesis of Human Genomes by Endogenous Retrotransposons, CELL 141(1):1253-1261 (Jun. 1, 2010).

Shukla, Ruchi et al. Endogenous Retrotransposition Activates Oncogenic Pathways in Hepatocellular Carcinoma, CELL 153(1):101-111 (Mar. 1, 2013).

Adiconis, Xian et al. Comparative analysis of RNA sequencing methods for degraded or low-input samples, Nature Methods, 10(7):623-629 (May 19, 2013).

European Application No. 15746731.7 Search Report dated Sep. 5, 2017.

Green, S.J. et al. Suicide Polymerase Endonuclease Restriction, a novel technique for enhancing PCR amplification of minor DNA templates, Applied and Environmental Microbiology, 71(8):4721-4727 (Aug. 1, 2005).

International Application No. PCT/US2016/019609 International Preliminary Report on Patentability dated Aug. 29, 2017.

International Application No. PCT/US2017/017530 International Preliminary Report on Patentability dated Aug. 23, 2018.

Jinek, M. et al. A programmable dual-RNA-guided DNA endonuclease in adaptive bacterial immunity. Science 337, Supp. pp. 1-37 (2012).

Kantarjian, H.M. et al. Dose escalation of imatinib mesylate can overcome resistance to standard-dose therapy in patients with chronic myelogenous leukemia. BLOOD, 101(2):473-475 (Jan. 15, 2003).

Lerat, E. et al. Influence of the transposable element neighborhood on human gene expression in normal and tumor tissues. Gene 396:303-311 (2007).

U.S. Appl. No. 15/116,404 Non-Final Office Action dated May 23, 2018.

U.S. Appl. No. 15/121,725 Final Office Action dated Sep. 6, 2018.

U.S. Appl. No. 15/121,725 Non-Final Office Action dated Feb. 9, 2018.

Bhargava et al., Technical variations in low-input RNA-seq methodologies. Scientific Reports 4:3678, 1-10 (2014).

Brouilette et al., A simple and novel method for RNA-seq library preparation of single cell cDNA analysis by hyperactive Tn5 transposase. Developmental Dynamics 241(10):1584-1590 (2012).

Gomaa et al., Programmable Removal of Bacterial Strains by Use of Genome-Targeting CRISPR-Cas Systems. mBio 5(1):e00928-e00913 (2014).

U.S. Appl. No. 15/121,725 Office Action dated Aug. 1, 2019.

Gasiunas et al., Cas9—crRNA ribonucleoprotein complex mediates specific DNA cleavage for adaptive immunity in bacteria. PNAS109(39):E2579-E2586 (2012).

PCT/US2020/017707 International Search Report and Written Opinion dated May 21, 2020.

U.S. Appl. No. 15/121,725 Final Office Action dated Apr. 13, 2020.

PCT/US2020/052652 International Search Report and Written Opinion dated Dec. 29, 2020.

U.S. Appl. No. 15/121,725 Non-Final Office Action dated Nov. 10, 2020.

\* cited by examiner

Mutational Insertion Mediated Amplification

In vitro transcription from T7 promoter
creates RNA copies of genome

T7 promoter sequence randomly inserted into genomic DNA by transposase

FIG. 8

A)
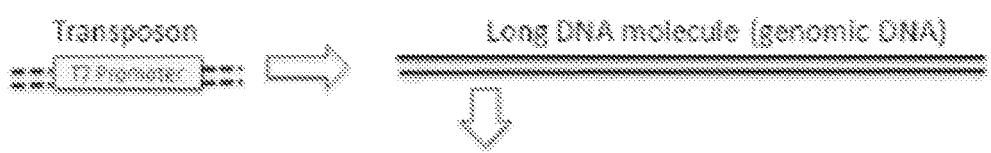

B) T7 Promoters inserted into long dsDNA with high frequency (500-2kb average)

Linear amplification of DNA is obtained through In Vitro Transcription

Reverse Transcription using Rd1-adapter tailed random primers and biotin nucleotides creates partial NGS library

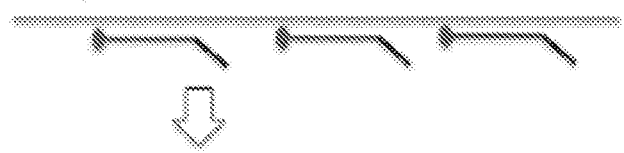

C)

Capture on streptavidin beads and convert to full NGS libraries through second strand cDNA synthesis followed by low cycle PCR

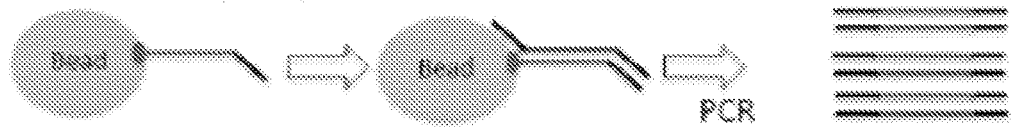

FIG. 14A-D
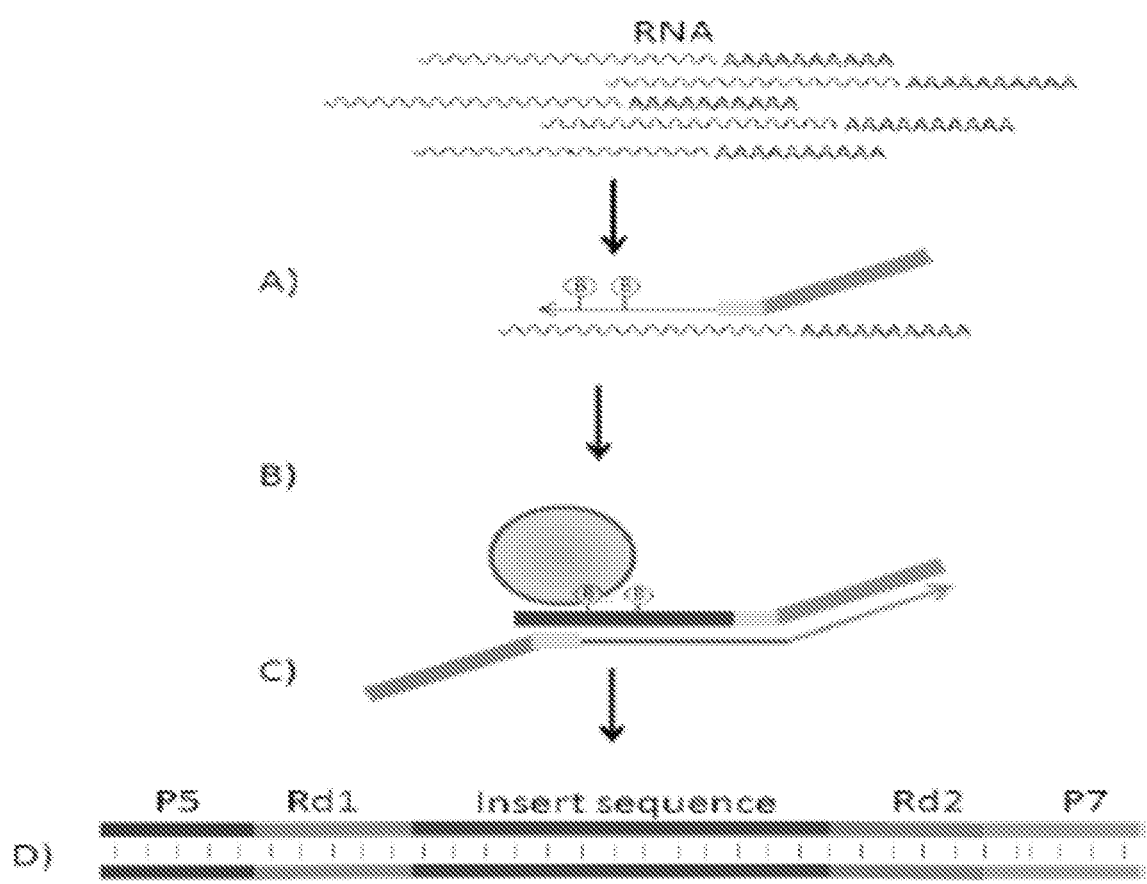

METHODS AND COMPOSITIONS FOR SEQUENCING

RELATED APPLICATIONS

The present application is a national stage entry of International Application No. PCT/US2016/019609 filed Feb. 25, 2016, which claims priority to U.S. Provisional Application Ser. No. 62/120,734, filed Feb. 25, 2015, the contents of which are hereby incorporated by reference in their entirety.

BACKGROUND OF THE INVENTION

Human genome sequencing is becoming a rapid, low cost procedure. This is in large part due to a dramatic increase in the capacities of current DNA sequencers. However, the short read lengths of these sequencers pose a challenge to genome assembly. Numerous strategies of dilution based molecule labeling have been devised to address this challenge. However, these methods are often cumbersome and have flaws that require these techniques be used in addition to standard genome sequencing. Particular problems include allelic dropout, template switching and chimera formation.

SUMMARY OF THE INVENTION

Methods disclosed herein comprise transposase mediated (and other types of enzyme-mediated) insertion of a nucleic acid insert sequence into a plurality of sites within individual molecules of a nucleic acid sample, thereby producing a long contiguous DNA molecule comprising regions or fragments of target DNA interspersed with insertional nucleic acids. Exemplary enzymes include recombinases, such as an integrase or a transposase. In some cases the enzyme is an integrase. In some cases the enzyme is a transposase, such as Tn5 transposase. Other transposases, integrases, or recombinase enzymes are contemplated and are consistent with the disclosure herein.

Methods and compositions herein relate to multiply tagging a nucleic acid sample with an insert nucleic acid fragment used to direct PCR or other amplification of adjacent nucleic acid sequence. The sequence is used to direct RNA transcription of adjacent nucleic acid sequence into RNA that can be concurrently or subsequently reverse-transcribed into RNA that can be amplified or sequenced by downstream methods. The insertion sequence facilitates obtaining nucleic acid sequence information such as nucleic acid sequence information adjacent to the insertion site. In some alternate embodiments insert nucleic acid fragment sequence is used as a primer binding site to direct primer-extension-mediated library generation, either as an alternative or in combination.

Disclosed herein are methods suitable for the generation of accurate, highly amplified libraries to be used for de novo sequencing of nucleic acid samples. Libraries generated hereby achieve highly accurate linear amplification of genomic samples derived from a sample as small as a single cell or less. The amplification is highly efficient and largely uniform throughout the sample, such that as much as 90% or more of the original sample is amplified 1000× or more, and such that the vast majority of the amplified library (as much as 85% or more) is present at a level within 4× of the mean. These parameters indicate that the amplification is both very high and largely uniform throughout the sample, rendering it particularly suitable for downstream analysis.

Amplification is achieved through the random insertion of a promoter sequence throughout a sample, followed by transcription-based generation of an intermediate RNA library. The intermediate RNA library consists of members that are derived directly from the sample template rather than having their synthesis be directed from prior synthesis intermediates as is the case in PCR based, phi-29 based, or other amplification methods. As a result, errors that may be introduced in the synthesis of a particular library intermediate RNA molecule are not amplified and do not propagate throughout the process of library generation. Intermediates are synthesized directly from the sample, and thus any errors introduced in a library constituent are likely to be unique to that molecule. Thus, independent of the overall error rate in library synthesis, errors in synthesis are likely to be unique or at least very rare in the intermediate library. As a result, they are easily distinguished from mutations present in the sample, even rare mutations, in downstream sequence analysis.

Another benefit of the library's RNA intermediates is that, unlike PCR or DNA synthesis-based library amplification, the 3' ends of RNA intermediates do not serve as primers for further synthesis. Thus, chimeric molecule formation is dramatically reduced in library generation relative to methods relying on PCR or phi-29.

Libraries are generated through the random introduction of promoter sequences into sample DNA. Insertion sequences are introduced through transposase treatment, recombinase treatment, invertase treatment or any other treatment, enzymatic or otherwise, that preserves phase information of the original sample. Tn5 treatment is a preferred insertion approach, but others are contemplated and consistent with the production of the libraries herein.

A benefit of the methods herein is that insertion and amplification are largely independent of the sequence of the sample prior to insertion.

Repeat regions are more easily sequenced because random insertion produces an 'insertion fingerprint' that renders otherwise repetitive regions unique for the purpose of library synthesis. By introducing a random insertion pattern, one is able to use the insertion pattern to map sequence reads to the locus harboring that insertion pattern. Thus repetitive regions, like loci harboring large multimeric line repeats, sine repeats, or other repetitive elements, are accurately mapped by the methods and libraries herein, while using conventional methods such loci may collapse to a single monomer at best.

Additionally, GC biases in the sample do not impact intermediate or final library synthesis, as RNA transcription is much less vulnerable to GC content than is PCR or other primer annealing based amplification approaches.

Accordingly, the methods and RNA intermediate libraries presented herein represent a substantial improvement over approaches otherwise available for the production of sequencing libraries for the sequencing of nucleic acid sample such as genomic samples.

Methods, compositions and sequence libraries are suitable for the generation of synthetic long read sequences from nucleic acid samples as small as sub-genomic samples or smaller. Starting from a small population of cells or even a single cell, nucleic acids are diluted to sub-genomic amounts prior to library generation, thereby avoiding sampling bias that may emerge when starting from bulk material, and reduce the number of compartments required on a library construction and sequencing workflow. Samples are amplified linearly, such as from nucleic acid fragments randomly inserted into the nucleic acid sample, to reduce amplification bias that may emerge from alternate amplification systems, such as per-based exponential sample amplification, phi-29 based amplification, or any system where a sample template is copied and the copies are used as templates for further intermediate generation. Linear amplification is accomplished through RNA polymerase promoter-directed synthesis of RNA molecules from nucleic acid fragments that have been randomly inserted into the nucleic acid sample. As the amplification intermediates are RNA molecules, they do not serve as templates for further intermediate synthesis, and in the event of hybridization to one another or to the sample, they do not prime extension to form further intermediates.

A benefit of the generation of RNA polymerase promoter-directed synthesis of RNA molecules from the nucleic acid fragments randomly inserted into the nucleic acid sample is that the resultant RNA library is derived directly from the sample nucleic acid, rather than from intermediate synthesis products that serve as templates. RNA molecules do not serve as templates for further RNA synthesis, and free RNA molecule 3' OH moieties do not support further extension upon reannealing to the original sample, other intermediates or other regions of the molecule itself.

As a consequence, artifactual errors common to some sequencing libraries are avoided. In particular, errors in RNA molecule synthesis are not propagated, and will occur independently of one another. Thus unlike approaches involving exponential amplification of intermediates, individual errors in library synthesis are independent of one another and are each likely to be individually rare. Rare errors are easily identified in the context of the full library sequence, and are easily excluded. This is in contrast to libraries involving exponential amplification, where errors that occur in early intermediate synthesis are propagated exponentially, and can become so abundant as to be difficult to distinguish from allelic variation or rare events such as mutations in a subset of the cells of a sample, such as a tumor cell subset.

Chimeric artifacts are dramatically reduced if not effectively eliminated because the 3' OH of synthesized RNA intermediates are not suitable for template directed extension upon their melting and reannealing in subsequent steps of synthesis. 3' end reannealing is a substantial source of chimeric artefact formation in alternate systems, because the resulting chimeric molecules are difficult to distinguish from translocations, duplications inversions or deletions in the original sample.

Long repeat regions are resolved, even in situations where the long repeats occur at multiple loci in a sample. Insertion of nucleic acid fragments randomly inserted into the nucleic acid sample superimposes a level of uniqueness throughout the sample (an 'insertion fingerprint'), such that sequences obtained from repetitive regions are mapped, in combination with their superimposed nucleic acid fragment random insertion patters, to unique loci of the sample. Thus, regions that are difficult to amplify, difficult to sequence and difficult to map to unique loci of a repetitive genome sample are far more easily and more accurately sequenced using the methods, compositions and libraries disclosed herein.

RNA polymerase-directed synthesis of an RNA intermediate library also avoids synthesis biases that often skew PCR-amplified libraries. RNA polymerase-directed synthesis of an RNA intermediate library is largely independent of GC concentration of the substrate, so there is a dramatic reduction in GC bias in the finalized library.

Through the methods herein, one synthesizes an RNA library having 90% or greater coverage of the original sample in the RNA library or in its reverse-transcribed DNA library product. Through multiple rounds of linear amplification, the level of amplification is remarkable—samples are amplified from 100×, or 1000×, up to 1,000,000× or greater relative to an original sample such as a sub-haploid sample derived from a single cell. This coverage is strikingly uniform relative to PCR-based libraries, such that often at least 85% of the synthesized library is present at a level within 4× (or ¼×) of the mean or median level of amplification of the sample overall.

Using the methods and workflows presented herein, these benefits are obtained without additional time relative to some library generation approaches currently in use.

Thus, a sample as small as a sub-haploid genomic sample from a single cell is amplified, uniformly and to a level far above that needed for most library sequencing methods. Chimeric library artefacts are dramatically reduced if not eliminated, and synthesis errors are easily identified and culled from the final library sequence. Variation is introduced into regions that are repetitive at a single locus or at multiple loci or both, such that repetitive regions are easily sequenced and assigned a correct size and position within a genomic scaffold or sequence.

Alternately, some embodiments comprise annealing primers to nucleic acid fragments that have been randomly inserted into the nucleic acid sample, and extension to form library intermediates.

Provided herein are methods of sequencing a nucleic acid sample, such as a nucleic acid sample having a sequence comprising an element repeated at a first region and a second region. Some such methods comprise inserting a nucleic acid tag having a nucleic acid tag sequence into the first region at a first repeat site generating a first sequence read comprising element sequence and nucleic acid tag sequence at the first repeat site, and a second sequence read comprising element sequence spanning the first repeat site from the nucleic acid sample, and assigning the first sequence read comprising repetitive element sequence and nucleic acid tag sequence at a first repeat site to the first region. Various aspects of these methods are recited below, contemplated as distinct or in combination. Methods are contemplated to optionally include aspects wherein the repeat site comprises a position within a repetitive element or wherein the region comprises a locus of a genome that harbors a repeat site. Methods optionally comprises assigning the second sequence read comprising repetitive element sequence spanning the repeat site to the second region. It is further contemplated that the nucleic acid tag comprises RNA promoter sequence. Nucleic acid tags comprising RNA promoter sequences include at least one of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. RNA promoter sequences are contemplated to comprise a T7 sequence. Also contemplated in methods herein is inserting a nucleic acid tag having a nucleic acid tag sequence into a second site in the element at a second region. Methods may also include assigning a third sequence read comprising repetitive element sequence and comprising nucleic acid tag sequence at the second site to the second region. Methods are also contemplated comprising inserting at least two nucleic acid tags having nucleic acid tag sequences into at least two sites in the element at two or more regions at an average density of no more than 1 insertion per 500 basepairs.

Some methods contemplated herein involve converting a multimeric repeat nucleic acid region that is not uniquely sequenceable into a unique region. Some of such methods comprise treating the isolated nucleic acid sample comprising a repeated nucleic acid region that is not uniquely sequenceable a using a random insertional mutagen to insert a tag into one copy of said repeated nucleic acid region, thereby rendering said one copy of said repeated nucleic acid region unique, obtaining sequence reads from the insertionally mutagenized isolated nucleic acid sample, and assigning sequence reads having a repeated nucleic acid region sequence and a tag sequence to a unique repeated nucleic acid region. Various aspects of these methods are recited below, contemplated as distinct or in combination. Some methods optionally comprise inserting two or more nucleic acid tags having nucleic acid tag sequences into two or more sites in the element at two or more regions at an average density of no more than 1 insertion per 500 basepairs. It is further contemplated that the nucleic acid tag comprises an RNA promoter. Nucleic acid tags comprising RNA promoter sequences include at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. RNA promoter sequences are contemplated to comprise at least one of T7, T3 and SP6. RNA promoter sequences are also contemplated to comprise T7. It is further contemplated that the method comprises contacting said insertionally mutagenized isolated nucleic acid sample to an RNA polymerase. Also contemplated in methods herein is generation of a population of RNA molecules comprising tag sequence and repeated nucleic acid region sequence. Methods also include sequence reads, wherein the sequence reads are obtained from the population of RNA molecules. Further contemplated are methods wherein the population of RNA molecules is reverse transcribed to generate DNA molecules. Methods herein are also contemplated to comprise aspects wherein the random insertional mutagen comprises a transposase. Contemplated herein are methods wherein the transposase is at least one transposase selected from the list consisting of Tn5 transposase, sleeping beauty transposase, piggybac transposase, and Mariner transposase. Transposases contemplated herein comprise a Tn5.

Also provided herein are isolated nucleic acid samples, such as isolated nucleic acid samples treated with an insertional mutagen. Some such nucleic acid samples comprise a first repeat element interrupted by a tag at a first position and a second copy of said repeat element is interrupted by said tag at a second position, such that sequence reads comprising tag sequence and repeat element sequence indicative of said tag at said first position uniquely map to said first repeat element. Various aspects of these nucleic acid samples are recited below, contemplated as distinct or in combination. Nucleic acid samples contemplated herein optionally comprise two or more nucleic acid tags having nucleic acid tag sequences at two or more sites in the repeat element at two or more regions at an average density of no more than 1 insertion per 500 basepairs. Nucleic acid tags comprising RNA promoter sequences include at least one of the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. RNA promoter sequences are contemplated to comprise at least one of the list consisting of a T7, T3, and SP6. RNA promoter sequences are contemplated to comprise a T7 promoter. Insertional mutagens of the nucleic acid samples contemplated herein a transposase selected from the list consisting of Tn5 transposase, sleeping beauty transposase, piggybac transposase, and Mariner transposase. Alternatively, insertional mutagens contemplated herein comprise an integrase. Repeat elements of the nucleic acid samples contemplated herein are selected from the group consisting of a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, a transposable element, a LINE, and a SINE. Nucleic acid samples herein are contemplated to optionally be used to create an RNA library generated by contacting a nucleic acid sample to an RNA polymerase. Alternatively, nucleic acid samples herein are contemplated to be used to create a DNA library generated by contacting a RNA library herein to a reverse-transcriptase.

Additional nucleic acid samples contemplated herein include a genomic nucleic acid sample sequencing library comprising a plurality of RNA molecules. Some such plurality of RNA molecules comprise a first end comprising tag sequence and a second end comprising genomic nucleic acid sample sequence, wherein at least 90% of said genomic nucleic acid sample such as a human genomic sample is represented in said plurality of RNA molecules. Various aspects of these nucleic acid sequencing libraries are recited below, contemplated as distinct or in combination. Also provided, nucleic acid sequencing libraries contemplated herein comprise a plurality of RNA molecules generated directly from the genomic nucleic acid sample. Optionally, such nucleic acid sequencing libraries comprise at least 95% of said genomic nucleic acid sample is represented in said plurality of RNA molecules. Alternatively, such nucleic acid sequencing libraries comprise at least 99% of said genomic nucleic acid sample is represented in said plurality of RNA molecules. Nucleic acid sequencing libraries provided herein also comprise a sample wherein said sample is amplified at least 100× relative to said genomic sample. Alternatively, nucleic acid sequencing libraries provided herein comprise a sample wherein said sample is amplified at least 1000× relative to said genomic sample. Also provided in nucleic acid sequencing libraries herein are sequencing libraries wherein at least 85% of said amplified sample is present at a level that is no more than 4× of a mean amplification level. Nucleic acid sequencing libraries contemplated herein include libraries wherein said RNA promoter sequence comprises at least an identifiable portion promoter is at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. RNA promoter sequences in nucleic acid sequencing libraries herein alternatively comprise at least one of T7, T3 and SP6. RNA promoter sequences in nucleic acid sequencing libraries optionally comprise a T7 promoter sequence. Also provided herein are nucleic acid sequencing libraries wherein said genomic nucleic acid sample is treated to insert a nucleic acid encoding said RNA promoter sequence into said genomic nucleic acid sample. Optionally, nucleic acid libraries include libraries comprising a genomic nucleic acid sample contacted to an integrase. Alternatively, nucleic acid libraries include libraries comprising a genomic nucleic acid sample contacted to a transposase. Transposases contacted to a genomic nucleic acid sample in nucleic acid sequencing libraries contemplated herein comprise a transposase is selected from the list consisting of Tn5 transposase, sleeping beauty transposase, piggybac transposase, and Mariner transposase. Optionally, transposases contacted to genomic nucleic acid samples in nucleic acid sequencing libraries include Tn5. Included in nucleic acid sequencing libraries, are DNA libraries, such as a DNA library comprising a RNA library provided herein contacted to a reverse-transcriptase.

Nucleic acid samples herein are also contemplated to include genomic nucleic acid sample sequencing libraries, such as a genomic nucleic acid sample sequencing library comprising a plurality of RNA molecules. Such plurality of RNA molecules are transcribed directly from the genomic nucleic acid sample, such that no RNA molecule serves as a template for a second RNA molecule. Various aspects of these nucleic acid sequencing libraries are recited below, contemplated as distinct or in combination. For example, genomic nucleic acid sample sequencing libraries are contemplated to comprise populations wherein at least 90% of said genomic nucleic acid sample is represented in said library. Some genomic nucleic acid sample sequencing libraries are contemplated to comprise at least 95% of said genomic nucleic acid sample is represented in said library. Optionally, genomic nucleic acid sequencing libraries comprise at least 99% of said genomic nucleic acid sample is represented in said library. It is further contemplated that genomic nucleic acid sample sequencing libraries comprise a sample is amplified at least 100× relative to said genomic sample. Alternatively, it is contemplated that said sample is amplified at least 1000× relative to said genomic sample. Optionally, the genomic nucleic acid sample sequencing library comprises a library wherein at least 85% of said amplified sample is present at a level that is no more than 4× of a mean amplification level. Genomic nucleic acid sample sequencing libraries herein further comprise at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Alternatively, genomic nucleic acid sequencing libraries include an RNA promoter sequence comprising at least one of T7, T3 and SP6. Optionally, genomic nucleic acid sequencing libraries include an RNA promoter sequence comprising a T7 promoter sequence.

Also provided herein are isolated nucleic acid samples, such as nucleic acid samples comprising an isolated genomic nucleic acid sample into which a exogenous promoter is inserted at an average density of at least 1 insertion per 5 kb. Various aspects of these isolated nucleic acid samples are recited below, contemplated as distinct or in combination. For example, nucleic acid samples contemplated herein include samples wherein the exogenous promoter is inserted at an average density of no more than 1 insertion per 500 basepairs. Optionally, the nucleic acid sample is contacted to an RNA polymerase. Nucleic acid samples herein are also contemplated to include samples comprising a plurality of RNA molecules comprising exogenous promoter sequence and isolated genomic nucleic acid sample sequence. Optionally, nucleic acid samples are contemplated to include samples wherein 90% of the isolated genomic nucleic acid sample sequence is represented by said plurality of RNA molecules. Alternatively, 95% of the isolated genomic nucleic acid sample sequence is represented by said plurality of RNA molecules. Alternatively, 99% of the isolated genomic nucleic acid sample sequence is represented by said plurality of RNA molecules. Also contemplated herein, nucleic acid samples are amplified at least 100× relative to said genomic sample. Optionally, nucleic acid samples are amplified at least 1000× relative to said genomic sample. Further nucleic acid samples contemplated comprise at least 85% of said amplified sample is present at a level that is no more than 4× of a mean amplification level.

Also provided herein are isolated nucleic acid samples, such as a nucleic acid sample comprising a plurality of repetitive elements having a length of at least 300 to 500 base pairs, wherein at least 50%, 60%, 70%, 80%, or 90% or greater than 90% of said plurality of repetitive elements are independently interrupted by at least one species of randomly inserted tag. Various aspects of these isolated nucleic acid samples are recited below, contemplated as distinct or in combination. For example, nucleic acid samples wherein the plurality of repetitive elements have a length of at least 6000 base pairs. Nucleic acid samples are also contemplated to include at least one species of randomly inserted tag comprising a nucleic acid encoding a promoter sequence. RNA promoters included in nucleic acid samples herein optionally include at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. RNA promoters herein optionally comprise at least one of T7, T3 and SP6. RNA promoters alternatively comprise a T7 promoter sequence. Nucleic acid samples herein are also contemplated to include samples wherein said sample is contact to an RNA polymerase. Further contemplated of nucleic acid samples herein are samples wherein RNA molecules representing at least 90% of said nucleic acid sample are generated. Alternatively, RNA molecules representing at least 95% of said nucleic acid sample are generated. Optionally, RNA molecules representing at least 99% of said nucleic acid sample are generated. Also contemplated is a nucleic acid sample wherein said sample is subsequently contacted to a DNase.

Methods provided herein also include methods of generating a modified nucleic acid. Some such methods comprise combining an insertional nucleic acid comprising an adapter sequence that is flanked by nucleic acid integrase recognition sequences; a target nucleic acid molecule; and a nucleic acid integrase, wherein the nucleic acid integrase covalently inserts the insertional nucleic acid into the target nucleic acid at a first location and at a second location within the target nucleic acid molecule, said first location and said second location being separated by at least 200 bp. Various aspects of these methods are recited below, contemplated as distinct or in combination. Methods optionally comprise said first location and said second location are separated by at least 500 bp. Alternatively, said first location and said second location are separated by at least 750 bp, 1.0 kb, 1.5 kb, 2.0 kb, 2.5 kb. Alternatively, said first location and said second location are separated by at most 2.0 kb, 1.5 kb, or 1 kb or less than 1 kb.

Methods provided herein also include methods of generating a plurality of multi-insert nucleic acids. Some such methods comprise combining an insertional nucleic acid comprising an adapter sequence that is flanked by nucleic acid integrase recognition sequences; a plurality of target nucleic acids; and a nucleic acid integrase, wherein the nucleic acid integrase cleaves one or more of the plurality of target nucleic acids to produce one or more recombination sites, recognizes the nucleic acid integrase recognition sequences; and inserts the insertional nucleic acid into the one or more recombination sites to generate the plurality of multi-insert nucleic acids. Various aspects of these methods are recited below, contemplated as distinct or in combination. Contemplated herein are methods wherein the adapter sequence comprises an RNA promoter sequence. Further contemplated are methods wherein the adapter sequence comprises at least one of T7, T3 and SP6 RNA promoter sequence. Also contemplated are methods wherein the adapter sequence comprises T7 RNA promoter sequence. Methods contemplated herein optionally further comprise adding a PCR primer to the plurality multi-insert nucleic acids, wherein the PCR primer anneals to the insertional nucleic acid or a portion thereof, and amplifying one or more of the plurality of multi-insert nucleic acids or a portion thereof. Optionally, the PCR primer anneals to the adapter sequence or portion thereof. Methods contemplated herein alternatively further comprise diluting the plurality of multi-insert nucleic acids into a plurality of containers, to produce a first plurality of diluted multi-insert nucleic acids in a first container and a second plurality of diluted multi-insert nucleic acids in a second container. Methods contemplated herein optionally comprise diluting the plurality of multi-insert nucleic acids into a plurality of containers dilutes the plurality of multi-insert nucleic acids such that a single multi-insert nucleic acid is present in each container of the plurality of containers. In methods contemplated herein the plurality of multi-insert nucleic acids optionally comprises genomic DNA, and wherein diluting the plurality of multi-insert nucleic acids into a plurality of containers dilutes the genomic DNA such that a haplotype frequency in a container is very low. Alternatively, in methods herein the plurality of containers comprises a container selected from a tube, a microwell and a droplet. Optionally, methods of generating a plurality of multi-insert nucleic acids further comprise providing a first PCR primer comprising a first tag to the first container, wherein at least a portion of the first PCR primer anneals the insertional nucleic acid or portion thereof; providing a second PCR primer comprising a second tag to the second container, wherein at least a portion of the second PCR primer anneals to the insertional nucleic acid or portion thereof, and wherein the second tag is different than the first tag; providing a nucleic acid polymerase into the first container and the second container; amplifying the first plurality of diluted multi-insert nucleic acids or portions thereof, thereby producing a first plurality of tagged nucleic acids; and amplifying the second plurality of diluted multi-insert nucleic acids or portions thereby producing a second plurality of tagged nucleic acids. Alternatively, in such methods herein the first tag comprises a first tag nucleic acid sequence and the second tag comprises a second tag nucleic acid sequence, wherein the first tag nucleic acid sequence and the second tag nucleic acid sequence are different. Optionally, the nucleic acid polymerase is a phi29 DNA polymerase and the insertional nucleic acid comprises random primer annealing sites. Optionally, the nucleic acid polymerase is T7 polymerase and the insertional nucleic acid comprises a T7 primer annealing site. Methods contemplated herein optionally further comprise introducing a reverse transcriptase and random primers. Optionally, methods contemplated herein further comprise cleaving the insertional nucleic acid of the plurality of multi-insert nucleic acids to produce a plurality of multi-insert nucleic acid fragments, wherein each multi-insert nucleic acid fragment is flanked by the first portion of the insertional nucleic acid and the second portion of the insertional nucleic acid. Optionally, methods are contemplated wherein the cleaving occurs before adding the first and/or second PCR primer and the amplifying. Alternatively, methods herein further comprise pooling the first plurality of tagged nucleic acids and the second plurality of tagged nucleic acids. Methods herein optionally further comprise adding an affinity molecule to the first plurality of tagged nucleic acids and/or the second plurality of tagged nucleic acids. Optionally, the affinity molecule is biotin. Also contemplated herein are methods further comprising capturing the first plurality of tagged nucleic acids and/or the second plurality of tagged nucleic acids via the affinity molecule. Alternatively, methods herein further comprise sequencing the first plurality of tagged nucleic acids and the second plurality of tagged nucleic acids. Also contemplated herein are methods wherein the first portion of the insertional nucleic acid comprises a first portion of the adapter sequence and the second portion of the insertional nucleic acid comprises a second portion of the adapter sequence. Optionally, the first portion of the adapter sequence and the second portion of the adapter sequence comprise a different sequence. Alternatively, the first portion of the adapter sequence is the same as the second portion of the adapter sequence. Alternatively, the first portion of the adapter sequence and the second portion of the adapter sequence are adjacent prior to combining the insertional nucleic acid, plurality of target nucleic acids and integrase. Optionally, the first portion of the adapter sequence is an inverted sequence of the second portion of the adapter sequence. Alternatively, the first portion of the adapter sequence and the second portion of the adapter sequence form a palindromic sequence. Optionally, the nucleic acid integrase is a transposase. Optionally, herein, the transposase is a Tn5 transposase. Alternatively, herein, the nucleic acid integrase recognition sequences are mosaic ends. Methods contemplated herein alternatively comprise the ratio of transposase to insertional nucleic acid set such that insertional nucleic acids are introduced at an average density of 500 bp to 2 kb over a span of at least 3 insertional nucleic acid insertion sites.

Also provided herein are nucleic acid molecules, such as nucleic acid molecules comprising a chromosome-sized target nucleic acid and a plurality of insertional nucleic acids, wherein the plurality of insertional nucleic acids are distributed at a plurality of recombination sites throughout the target nucleic acid at an average density of at least one insert per 10 kb. Various aspects of these nucleic acid molecules are recited below, contemplated as distinct or in combination. Nucleic acid molecules contemplated herein comprise molecules wherein the insertional nucleic acid comprises a primer annealing sequence. Optionally, the insertional nucleic acid comprises a first primer annealing sequence and a second primer annealing sequence. Alternatively, the first primer annealing sequence and the second primer annealing sequence are adjacent. Alternatively, the first primer annealing sequence and the second primer annealing sequence are different. Alternatively, the first primer annealing sequence is an inverted sequence of the second primer annealing sequence. Alternatively, the first primer annealing sequence and the second primer annealing sequence comprise the same sequence. Alternatively, the first primer annealing sequence and the second primer annealing sequence form a palindrome. Optionally, the insertional nucleic acid comprises a transcriptional promoter. Nucleic acid molecules herein are also contemplated wherein the insertional nucleic acid encodes a promoter selected from the list of promoters consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Optionally, the insertional nucleic acid encodes a promoter selected from the list of promoters consisting of a T7, T3, and SP6. Optionally, the insertional nucleic acid encodes a T7 promoter. Nucleic acid molecules herein are contemplated wherein the transcriptional promoter is recognized by an RNA polymerase. Optionally, the insertional nucleic acid comprises a mosaic end, wherein the mosaic end is recognized by a transposase. Nucleic acid molecules are also contemplated herein wherein the target nucleic acid comprises a plurality of target nucleic acid fragments separated by one or more of the insertional nucleic acids of the plurality of inserted nucleic acids. Optionally, nucleic acid molecules are contemplated wherein each insertional nucleic acid of the plurality of insertional nucleic acids occurs at an average frequency of about 500 base pairs to about 2000 base pairs within the target nucleic acid. Optionally, the target nucleic acid comprises DNA. Optionally, the DNA comprises genomic DNA. Optionally, the DNA is mammalian DNA.

Also provided herein are insertional nucleic acid molecules, such as insertional nucleic acids comprising an adapter sequence and two mosaic ends, wherein the mosaic ends are recognized by a transposase. Various aspects of these nucleic acid molecules are recited below, contemplated as distinct or in combination. Optionally, contemplated herein are insertional nucleic acids wherein the adapter sequence comprises a first primer binding site and a second primer binding site, wherein the first primer binding site and a second primer binding site are adjacent, and the two mosaic ends flank the adapter sequence. Alternatively, the first primer binding site is an inverted sequence of the second primer binding site. Alternatively, the first primer binding site is a palindromic sequence of the second primer binding site. Alternatively, the first primer binding site and the second primer binding site comprise a different sequence. Also contemplated herein are insertional nucleic acids wherein the insertional nucleic acid, from 5' to 3', comprises a first mosaic end, a first primer binding site, a second primer binding site and a second mosaic end. Optionally, the adapter sequence comprises a transcriptional promoter.

Also provided herein are kits comprising insertional nucleic acids, such as kits comprising an insertional nucleic acid, wherein the oligonucleotide comprises a mosaic end that is recognized by a transposase; and a transposase. Various aspects of these kits are recited below, contemplated as distinct or in combination. Optionally contemplated herein the insertional nucleic acid further comprises an adapter sequence. Alternatively, the adapter sequence is flanked by a first mosaic end and a second mosaic end. Alternatively, the adapter sequence comprises a primer annealing sequence. Alternatively, kits contemplated herein further comprise a PCR primer that anneals to the primer annealing sequence. Optionally, the PCR primer comprises a tag. Alternatively contemplated herein are kits wherein a first PCR primer comprises a first tag and a second PCR primer comprises a second tag, wherein the first tag and the second tag are different. Optionally contemplated herein are kits further comprising a plurality of containers. Alternatively, the plurality of containers comprises a microwell plate. Also contemplated herein are kits wherein one or more containers of the plurality of containers contains a mixture comprising one or more of the transposase, a portion of the plurality of insertional nucleic acids and the first/second PCR primers. Alternatively, the transposase is a Tn5 transposase. Optionally contemplated herein are kits further comprising a polymerase.

Also provided herein are target nucleic acid molecules, such as target nucleic acid molecules comprising a first nucleic acid insert sequence at a first insertion site, a first nucleic acid insert sequence at a second insertion site, and a first nucleic acid sequence at a third insertion site, wherein said first insertion site and said second insertion site are separated by at least 250 bp of nucleic acid molecule sequence that is not first nucleic acid insert sequence. Various aspects of these target nucleic acid molecules are recited below, contemplated as distinct or in combination. Optionally contemplated herein said first nucleic acid insert sequence comprises a left border and a right border bound by a transposase. Alternatively contemplated herein said left border is bound by a transposase if not covalently linked to flaking sequence on either side of said left border. Alternatively, said right border is bound by a transposase if not covalently linked to flaking sequence on either side of said right border. Optionally, target nucleic acids are contemplated wherein a transposon directs covalent insertion of a molecule having said first nucleic acid insertion sequence into a nucleic acid molecule to generate a target nucleic acid molecule. Alternatively, said second insertion site and said third insertion site are separated by at least 250 bp of nucleic acid molecule sequence that is not first nucleic acid insert sequence. Optionally contemplated herein are nucleic acid molecules comprising a fourth insertion site, wherein said third insertion site and said fourth insertion site are separated by at least 250 bp of nucleic acid molecule sequence that is not first nucleic acid insert sequence. Alternatively, a first insertion site and a second insertion site are separated by at most 2.5 kb. Alternatively, said first nucleic acid insert sequence comprises a first primer binding site. Also contemplated herein are nucleic acid molecules, wherein said first nucleic acid insert sequence comprises a palindromic sequence such that a first primer binding site is present in a first orientation and a second orientation, said second orientation being antipolar to said first orientation. Optionally, said first nucleic acid insert sequence comprises a restriction endonuclease cleavage site between said first primer binding site orientation and said second primer binding site orientation. Alternatively, said first nucleic acid insert sequence comprises a first primer binding site and a second primer binding site. Alternatively, said first nucleic acid insert sequence comprises a restriction endonuclease cleavage site between said first primer binding site and said second primer binding site. Alternatively, said first nucleic acid insert sequence comprises an RNA polymerase promoter. Optionally, the RNA polymerase promoter is a T7 RNA polymerase promoter.

Also provided herein are compositions, such as compositions comprising a nucleic acid molecule comprising a first nucleic acid insert sequence at a first insertion site, a first nucleic acid insert sequence at a second insertion site, and a first nucleic acid sequence at a third insertion site, wherein said first insertion site and said second insertion site are separated by at least 250 bp of nucleic acid molecule sequence that is not first nucleic acid insert sequence, and a population of oligonucleotide primers, said population of oligonucleotide primers comprising a plurality of oligonucleotide primers each having sequence reverse complementary to said first nucleic acid insert sequence, and each of said plurality of oligonucleotide primers having a common barcode sequence. Various aspects of these compositions are recited below, contemplated as distinct or in combination. Compositions herein optionally are contemplated wherein said common barcode sequence corresponds to said nucleic acid molecule. Alternatively, said common barcode sequence corresponds to a container of said composition. Alternatively, said common barcode sequence corresponds to at least one container of a plurality of containers of said composition. Compositions herein are optionally contemplated wherein said container is a well in a multiwell plate. Alternatively, said container is a droplet. Alternatively, said container is a micelle.

Methods provided herein also include methods of assigning nucleic acid molecule-specific sequence information. Some such methods comprise: obtaining a nucleic acid sample comprising a nucleic acid molecule, inserting an insertion sequence into said nucleic acid molecule at a first site, amplifying nucleic acid molecule sequence adjacent to said first site, and sequencing said nucleic acid molecule sequence adjacent to said first site. Various aspects of these methods are recited below, contemplated as distinct or in combination. Contemplated herein are methods wherein optionally inserting said insertion sequence comprises contacting said nucleic acid with a nucleic acid integrase. Alternatively, said nucleic acid integrase comprises a transposase. Methods contemplated herein optionally comprise inserting an insertion sequence into said nucleic acid molecule at a second site, said second site separated from said first site by about 500 bp to 3 kb. Alternatively, said amplifying comprises contacting said insertion sequence with a first primer that anneals to said first insertion sequence at said first insertion site. Alternatively, said amplifying comprises contacting said insertion sequence with a second primer that anneals to said first insertion sequence at a second insertion site. Alternatively, methods herein comprise segregating said nucleic acid sample among a plurality of partitions prior to said amplifying. Optionally, said first primer sequence comprises a first tag that corresponds to a subset of said plurality of said partitions. Alternatively, said second primer sequence comprises a second tag that corresponds to a subset of said plurality of said partitions. Alternatively, said first tag and said second tag comprise identical sequence. Alternatively, said first tag and said second tag comprise non-identical sequence. Methods herein alternatively comprise contacting said first insertion sequence to an RNA polymerase prior to said amplifying. Optionally, said RNA polymerase is a T7 RNA polymerase. Methods herein optionally comprise contacting said first insertion sequence with DNase subsequent to contacting to an RNA polymerase. Methods herein optionally comprise contacting said first insertion sequence with reverse-transcriptase subsequent to contacting to an RNA polymerase. Alternatively, contacting said first insertion sequence with reverse-transcriptase concurrently with contacting said first insertion sequence with RNA polymerase.

Methods provided herein also include methods of telomere end mapping. Some such methods comprise inserting a plurality of nontelomeric extension supporting sequences into a telomeric region, extending nucleic acids from the insertion sites so as span additional insertion sites, sequencing the extension products, and assigning a telomeric order to an extension terminus common to a plurality of extension products. Various aspects of these methods are recited below, contemplated as distinct or in combination. Contemplated herein are methods wherein the nontelomeric extension supporting sequences comprise primer binding sites. Alternatively, the nontelomeric extension supporting sequences comprise RNA polymerase promoters. Optionally, the RNA polymerase promoters are selected from the list of promoters consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6. Alternatively, the RNA polymerase promoters are selected from the list of promoters consisting of T7, T3, and SP6. Alternatively, the RNA polymerase promoters are T7 promoters. Also contemplated herein are methods wherein the nontelomeric extension supporting sequences comprise promoter pairs, directing RNA transcription in opposite directions. Optionally, the extension products comprise RNA molecules. Alternatively, the extension products comprise 5' insertion border sequence and 3' telomere sequence. Alternatively, some extension products span at least one independent insertion site.

BRIEF DESCRIPTION OF THE DRAWINGS

The novel features of particular embodiments of the invention are set forth with particularity in the specification herein and in the appended claims. Elucidation and elaboration of the features and advantages of the present invention will be obtained by reference to the following detailed description that sets forth illustrative embodiments, in which the principles of the invention are utilized, and the accompanying drawings of which:

FIGS. 8A-8C depict an exemplary workflow.

FIG. 8A depicts T7 promoter sites introduced into genomic DNA using a transposase.

FIG. 8B depicts a one-pot isothermal reaction, the genomic DNA sequence is amplified by IVT and copied into first strand cDNA using biotin labeled nucleotides and random primers with molecular barcodes and the Illumina read 1 (Rd1) sequence on the 5' end.

FIG. 8C depicts capture of the first strand cDNA on streptavidin beads followed by second strand cDNA synthesis with random primers containing the Illumina read 2 (Rd2) sequence on the 5' end.

FIGS. 14A-14D depict an exemplary workflow for RNA-Rapid Library Prep (RNA-RLP).

FIG. 14A depicts RNA converted to cDNA in a reverse transcription reaction using a modified random primer that has an Illumina (Rd1) adapter sequence upstream of the random portion. Biotin-dCTP and biotin-dUTP are used in the reaction to modify the cDNA for subsequent ease of capture and purification.

FIG. 14B depicts capture of the cDNA/RNA with solid-support bound streptavidin beads and washing away the RNA under denaturing conditions generating the solid-support bound cDNA products.

FIG. 14C depicts products copied in a second strand synthesis reaction using an Illumina (Rd2) random primer and a polymerase that has good strand displacement activity ensuring the Rd1 and Rd2 adapter sequences are copied onto the final DNA molecule.

FIG. 14D depicts the solid support bound containing DNA duplex added directly to a PCR reaction for amplification with the full Illumina adapter sequences P5-Rd1 and P7-index-Rd2 in the PCR primers.

FIG. 15A depicts a genomic locus having a repetitive sequence.

FIG. 15B depicts the same region following random insertion of a nucleic acid fragment having an RNA promoter region.

FIG. 15C depicts the synthesis of RNA intermediates of varying length from the inserted RNA promoters.

FIG. 15D depicts assembly of library components into an accurate map of the repetitive region by anchoring the library constituents using their insertion sites in their repetitive contexts to assemble the region, and to put it into its genomic context using reads that extend into adjacent non-repetitive regions.

DETAILED DESCRIPTION OF THE INVENTION

Figure 1:
FIG. 1 depicts an exemplary insertional nucleic acid.

Insertional mutagenesis has been used for genome mapping of cancers and other disease. Methods include genome editing techniques, retroviral mutagenesis, and transposition, among others. Herein we describe methods for insertional modification of nucleic acids to facilitate subsequent analysis (e.g. sequencing). This is accomplished through the production of highly amplified, uniformly dense libraries that are clear of chimeric and amplification artefacts. These libraries are produced from a number of suitable samples, of amounts as low as those found in sub-genomic single-cell nucleic acid samples.

Some of such methods comprise transposition or transposase treatment, dilution and amplification of nucleic acids. Some of these methods comprise inserting inverted adapter sequences into a target DNA (e.g. genomic DNA), wherein the insertional nucleic acid sequences provide RNA promoter regions or, alternately or in combination, primer annealing sites.

Disclosed herein are methods for generating sequencing data suitable for genome phasing and de novo assembly which is superior to the conventional practice of reference based alignments. The advantages of the added phase information as well as the more accurate genome sequence assembly made possible by a de novo strategy have applications in human genome sequencing, agricultural biotechnology as well as sequencing genomes of novel organisms. The approaches disclosed herein involve sequencing samples as small as sub genomic fractions of a single individual's DNA, for example in compartments such as droplets in an emulsion using molecular barcodes to assign sequencing reads to their original sub genomic fraction. Sub genomic fractions are then de novo assembled into "synthetic long reads" that span up to 10-100 kb or more of individual DNA molecules. These synthetic long reads are combined computationally to generate longer contigs and map the whole genome sequence. Thus in some cases single-cell nucleic acid sequencing is accomplished de novo without the aid of a reference genome.

The approaches disclosed herein are able to overcome some significant flaws in conventional methods taught in the art or in use. The common steps involved in all synthetic long read technology include: 1) dilution of long DNA molecules, 2) amplification of those molecules, and then 3) the creation of labeled NGS libraries from this material. Compartmentalization such as micro droplet technology is ideally suited for the first step and there are a number of commercial systems available for its implementation. A notable difference between synthetic long read methods disclosed herein and conventional methods occurs in the amplification of a small number of long DNA molecules (step 2).

Multiple strand displacement amplification, long range PCR and combinations of the two (MALBEC) have been presented as possible sequence library generation approaches. While these approaches work to amplify small amounts of template DNA, all introduce significant amplification bias, GC bias, and sequence artifacts such as chimeric molecules from open 3' ends folding back on themselves and continuing polymerization. These artifacts are often clonally amplified and may represent a significant percentage of sequence reads. As a result, these artifacts cause an increase in the number of false positive mutations in a data set, and are difficult to extract or distinguish from the true sample sequence. In particular, differentially amplified artefacts are easily confused with allelic variation as may occur in a diploid sample, or with mutations that occur in a subpopulation of a heterogeneous sample, such as a tumor cell sample.

The resulting data, incorporated into many genomes assembled using these previously published methods, has gaps and sequence artifacts that can only be overcome, if at all, by combining the synthetic long read data with that of a standard high coverage genome assembly. This may result in greater than 2.5 times the cost of data generation by having to combine data sets from two distinct technologies.

Disclosed herein are methods that achieve amplification and packaging of a sample into a sequence-compatible library without the generation of the artefactual defects of the prior art approaches.

Some methods rely upon RNA promoter-polymerase systems, for example T7, T3, and SP6-based systems to drive transcription-based amplification to overcome bias through linear amplification of an RNA intermediate that is incapable of forming chimeric library artefacts. RNA promoter-polymerase systems, for example T7, T3, and SP6-based systems are relied upon to gain uniform coverage across a broad range of GC content in a sample. A benefit of some aspects of this approach is that chimeric molecules are not formed. Another benefit of some embodiments is that polymerase errors are not amplified as each copy of the sample DNA such as genomic DNA is derived from the original template molecule. Moreover, combining amplification and labeling in a single step allows for the use of existing high throughput droplet systems. Another substantial benefit of using a system or method disclosed herein is that, by relying upon random or semirandom insertion of sequences such as RNA polymerase promoter sequences (e.g., T7, T3 and SP6 promoter sequences, among others) into native DNA allows for the creation of novel sequence patterns in otherwise indistinguishable repetitive DNA regions. Thus, even the most complex or challenging repetitive regions of the human or other genome to be assembled are sequenced accurately, even down to the base pair position with all variations detected (see FIG. 8A, FIG. 8B, and FIG. 8C).

Disclosed herein are data showing partitioning of DNA into sub genomic fractions and creation of barcoded sequencing libraries from the DNA. The data may be created through a number of approaches, such as using random priming with primers containing, for example, over 1,000, over 10,000, over 100,000, over 1,000,000, 10,000,000 or more different barcodes followed by second strand cDNA synthesis and PCR amplification (see FIG. 9).

To obtain sufficient coverage per molecule in a given compartment to successfully de novo assemble the reads, DNA is amplified in a given compartment or droplet while simultaneously making barcoded sequencing libraries in parallel in a "one pot reaction". Genomic DNA is amplified via synthesis of RNA intermediates driven by RNA promoter sequences inserted at random throughout a genome. A single promoter sequence is relied upon to drive transcription throughout a sample. Alternately two or more promoters are used, either to optimize promoter activity or to increase diversity of the tags in the resulting library, or both. Promoter insertion is effected through a number of approaches, such as through transposase mediated insertion of T7 promoter nucleic acid molecules, often at high frequency.

Figure 10:
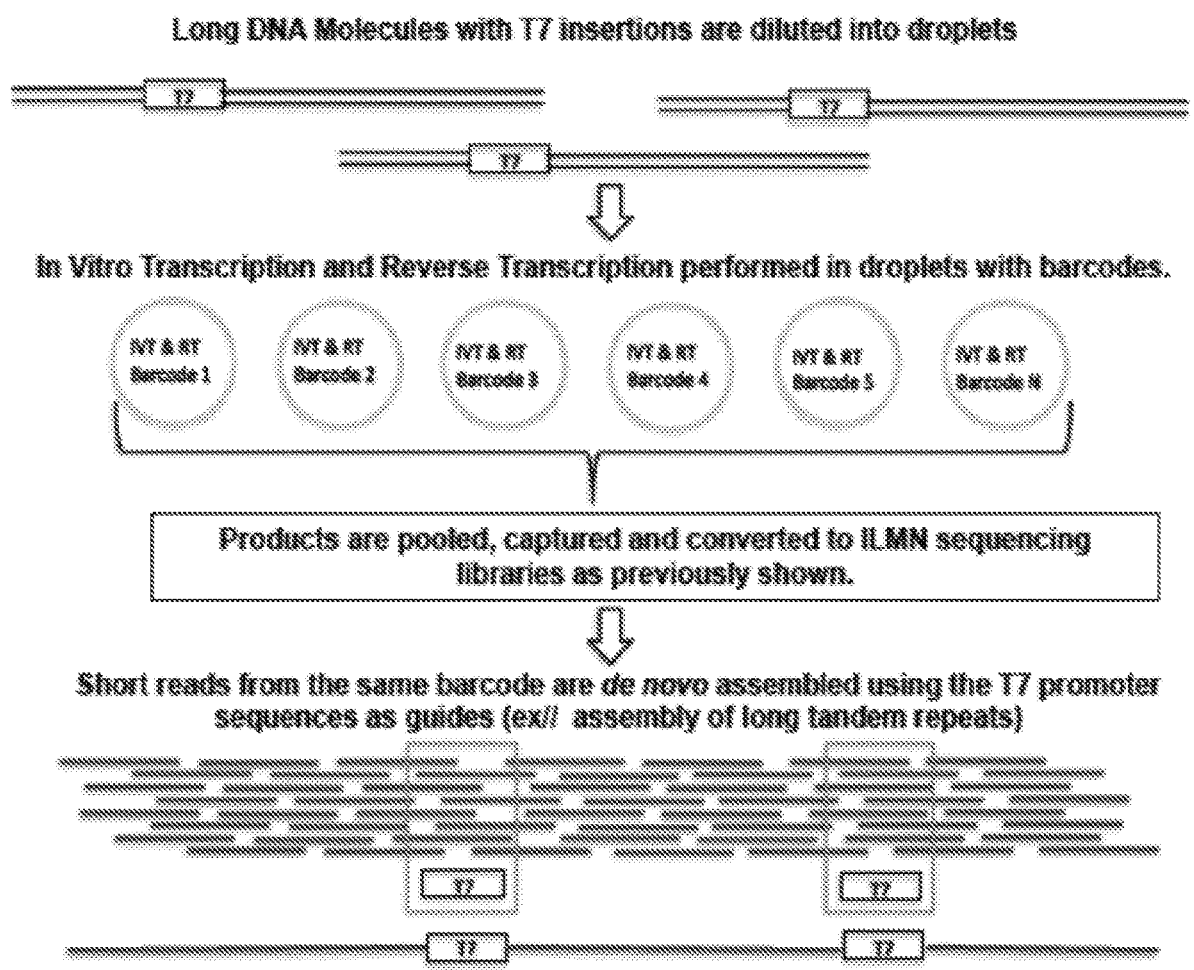
FIG. 10 depicts exemplary droplet conversion and de novo assembly of long molecules.
Figure 11:
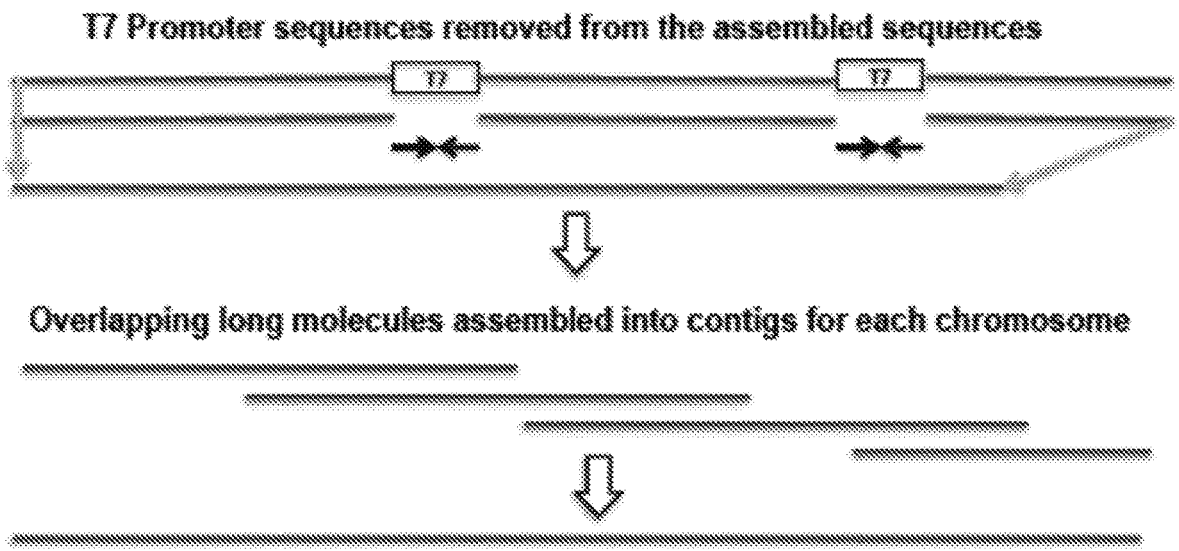
FIG. 11 depicts whole genome de novo assembly from individual contig sequences after T7 site removal.
Figure 12:
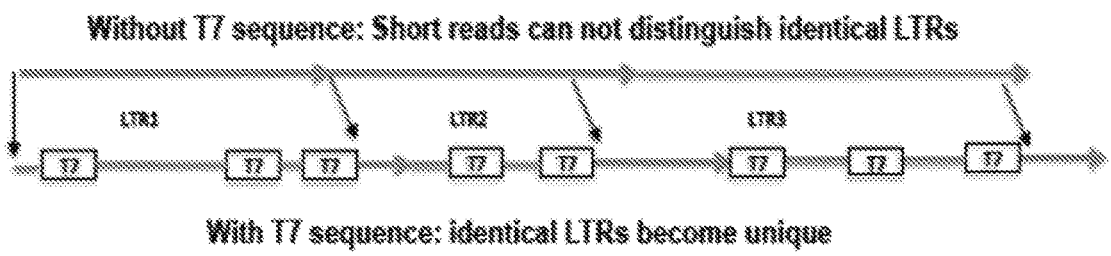
FIG. 12 depicts T7 insertions guide assembly of long tandem repeats (LTRs).

The genomic DNA is diluted and compartmentalized, such as depicted herein (FIG. 10). Alternate compartmentalization approaches are compatible with the disclosure herein. For example, the "one-pot" IVT/cDNA synthesis prep is applied in the droplets. This approach allows libraries to be made with sufficient coverage per molecule to assemble the DNA sequence of each compartment (optionally assisted by using the barcode information to identify reads belonging to an individual compartment) and then using the "synthetic long reads" created from each compartment to assemble and phase the whole genome (FIG. 11 and FIG. 12).

A feature of some aspects of these approaches is the generation of adequate sequencing coverage of each compartmentalized sub genomic DNA fraction. In some cases adequate sequence coverage of sub genomic DNA fractions is necessary, or variant phasing becomes challenging and requires additional sequencing (and thus higher cost) and may complicate de novo sequencing.

The incorporation of a genomic amplification strategy to the compartmentalized sub genomic DNA fractions by the methods disclosed herein solves this challenge in various embodiments. Existing whole genome amplification (WGA) methods utilize a random priming approach with a highly processive, strand displacing polymerase (e.g., phi29). It has been shown that phi29—based WGA methods are highly effective at amplification of very small sub genomic quantities of DNA (as little as 100 fg or ⅟₃₀th of a human haploid genome). However, in many instances these highly processive DNA polymerases introduce artifacts into the synthesized product. Often, these artifacts that cannot be overcome with increased sequencing depth.

There are several flaws with some approaches relying upon highly processive DNA polymerases such as phi29 based WGA. Some of these flaws in various embodiments include 1) highly biased amplification favoring a very narrow GC content range, 2) the high abundance of sequence artifacts (inversions and tandem repeats) that are created during the amplification process and 3) the propagation of these sequence artifacts and polymerase errors that are exponentially amplified during the reaction. Any of these defects can pose a problem to de novo assembly algorithms.

Approaches disclosed herein include novel combinations of in vitro transcription (IVT)-based amplification with a highly efficient genome wide RNA promoter insertion strategy, such as a transposase-based T7 promoter insertion strategy, that allows for de novo human genome sequencing. Said novel combination utilizes insertion of one or more RNA promoters at a chosen frequency randomly throughout the genome. Random insertion techniques involve but are not limited to use of transposases, integrases, viral insertion, and other techniques or methods known in the art. A wide range of RNA promoters are consistent with the approaches herein. T7, T3 or SP6 are exemplary promoters because of their size and compatibility with simple, robust, single-protein polymerase enzymes. However, a more complete list of suitable RNA promoters includes but is not limited to T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, U6, and other RNA promoters known in the art. These approaches enable minimally biased amplification of sub genomic DNA fractions, reduction or elimination of sequence artifacts, and removal of clonally amplified polymerase errors.

Libraries are linearly amplified directly from the DNA sample rather than tracing their lineage through PCR amplicons or synthesized DNA intermediates. Library intermediates are unable to prime further DNA synthesis. As a result, synthesis errors are not perpetuated, and synthesized intermediates do not generate chimeric molecules due to mispriming. Furthermore, synthesis errors appear as unique and independent of one another, and are therefore easily distinguished from genuine allelic variation in the underlying nucleic acid sample.

Short reads from the same sub-genomic DNA fraction are jointly de novo assembled to produce long contiguous sequences. The random promoter (e.g., T7) insertion events change the sequence construct of long repetitive sequences that would otherwise be identical in the human genome, thereby producing a unique "barcode" or "insertion fingerprint" of promoter insertion sites such as T7 insertion sites in otherwise identical repeat loci. The pattern of insertion events is random and will thus vary among insertion regions, even regions that are otherwise identical or difficult to distinguish even over long sequence distances. Thus, the insertion of nucleic acid fragment such as promoter sequence into a sample has the effect of creating a random "barcode," "insertion fingerprint," or data tag for each repeat region into which insertion occurs. As a result, otherwise indistinguishable repeat regions are uniquely and differentially tagged by their promoter insertion patterns. Reads or library molecules that span the inserted promoters are thus mappable to one or another repetitive region in common, based upon the insertion pattern that they are consistent with. The synthetic long molecules read through these "barcoded" repeats allowing the full repeat sequence to be de novo assembled for both pairs of chromosomes. By further relying upon reads that extend into adjacent non-repetitive regions of a sample, one is able to map these repetitive sequences accurately not only in terms of their repeat number or region size, but also in terms of their position within the overall sample scaffold sequence. This feature of some embodiments of the present disclosure enables de novo assembly of complex, repetitive samples, such as eukaryotic genomic samples including the human genome.

Methods disclosed herein comprise transposase mediated (and other types of enzyme-mediated) insertion of a nucleic acid insert sequence into a plurality of sites within individual molecules of a nucleic acid sample, thereby producing a long contiguous DNA molecule comprising regions or fragments of target DNA interspersed with insertional nucleic acids. Exemplary enzymes include recombinases, such as an integrase or a transposase. In some cases the enzyme is an integrase. In some cases the enzyme is a transposase, such as Tn5 transposase. Other transposases, integrases, or recombinase enzymes are contemplated and are consistent with the disclosure herein.

Methods and compositions herein relate to multiply tagging a nucleic acid sample with an insert nucleic acid fragment used to direct in vitro transcription, PCR, phi-29 amplification or other amplification of adjacent nucleic acid sequence. The sequence is used to direct RNA transcription of adjacent nucleic acid sequence into RNA that can be concurrently or subsequently reverse-transcribed into DNA. The DNA can be amplified or sequenced by downstream methods. Amplification of DNA, even via PCR, does not negate the benefits of RNA based linear amplification of the library intermediates.

The insertion sequence facilitates obtaining nucleic acid sequence information such as nucleic acid sequence information adjacent to the insertion site. In alternate embodiments insert nucleic acid fragment sequence is used as a primer binding site to direct primer-extension-mediated library generation, either as an alternative or in combination.

Most frequently, a single insertion nucleic acid fragment population is used. Alternatively, multiple different insertions are added, for example iteratively, to a single nucleic acid sample or to a subset of a nucleic acid sample. Insertions are sometimes selected such that insertion sequences added in multiple iterations are differentially tagged, so that one can identify at which insertional iteration a nucleic acid insertion was added. Optionally, an insertion tag corresponds to a compartment such as a well, droplet or micelle, or a set of wells, droplets or micelles to which at least one aliquot of a sample has been partitioned. Tags are located adjacent to primer binding sites such that, upon amplification, the tag sequence is included in any amplicon generated, such that an amplicon can be identified with a tagged insertion event. Alternately, some insertion sequences are untagged.

Definitions

A partial list of relevant definitions is as follows.

"Amplified nucleic acid" or "amplified polynucleotide" can be any nucleic acid or polynucleotide molecule whose amount has been increased at least two fold by any nucleic acid amplification or replication method performed in vitro as compared to its starting amount. For example, an amplified nucleic acid can be obtained from a polymerase chain reaction (PCR) which amplifies DNA in an exponential manner (for example, amplification to $2^n$ copies in n cycles). Amplified nucleic acid can also be obtained from a linear amplification.

"Amplification product" can refer to a product resulting from an amplification reaction such as a polymerase chain reaction.

An "amplicon" can be a polynucleotide or nucleic acid that is the source and/or product of natural or artificial amplification or replication events.

The term "biological sample" or "sample" generally refers to a sample that is generated de novo or that is wholly or in part isolated from a biological entity. The biological sample may show the nature of the whole of the biological entity from which it is obtained. Examples include, without limitation, bodily fluids, dissociated tumor specimens, cultured cells, and any combination thereof. Biological samples can come from one or more individuals. One or more biological samples can come from the same individual. One non limiting example would be if one sample came from an individual's blood and a second sample came from an individual's tumor biopsy. Examples of biological samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, microbiota, meconium, breast milk and/or other excretions. The samples may include nasopharyngeal wash. Examples of tissue samples of the subject may include but are not limited to, connective tissue, muscle tissue, nervous tissue, epithelial tissue, cartilage, cancerous or tumor sample, or bone. The sample may be provided from a human or animal. The sample may be provided from a mammal, including vertebrates, such as murines, simians, humans, farm animals, sport animals, or pets. The sample may be collected from a living or dead subject. The sample may be collected fresh from a subject or may have undergone some form of pre-processing, storage, or transport.

Nucleic acid sample as used herein refers to a nucleic acid sample for which sequence information is to be determined. A nucleic acid sample may be extracted from a biological sample above. Alternatively, a nucleic acid sample can be artificially synthesized, synthetic, or de novo synthesized. Often, the DNA sample is genomic, while in alternate cases the DNA sample is derived from a reverse-transcribed RNA sample. Some genomic samples, such as of viruses, are quite small. However, as used herein, a 'genomic' sample is often used in reference to a free-living organism's genome, such as a human, plant such as an agricultural crop, or even a human or plant or animal pathogen. In general. Such genomic samples comprise substantially large amounts of genomic information, such that amplification of a fraction of such sample such as 50% or greater of such a sample comprises amplification of a substantially large amount of sequence information.

"Bodily fluid" generally can describe a fluid or secretion originating from the body of a subject. Bodily fluids can be a mixture of more than one type of bodily fluid mixed together. Some non-limiting examples of bodily fluids can be: blood, urine, bone marrow, spinal fluid, pleural fluid, lymphatic fluid, amniotic fluid, ascites, sputum, or a combination thereof.

"Complementary" or "complementarity," or "reverse-complementarity" can refer to nucleic acid molecules that are related by base-pairing. Complementary nucleotides are, generally, A and T (or A and U), or C and G (or G and U). Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100%) complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Hybridization temperatures are generally at least about 2° C. to about 6° C. lower than melting temperatures ($T_m$).

A "barcode" or "molecular barcode" is any sequence information used to label or identify adjacent nucleic acid molecule sequence. The barcode can label a molecule such as a nucleic acid or a polypeptide. The material for labeling can be associated with information. A barcode can be called a sequence identifier (i.e. a sequence-based barcode or sequence index). A barcode can be a particular nucleotide sequence, or a particular insertion pattern, for example within a repetitive region of a genome. A barcode can be used as an identifier. A barcode can be a different size molecule or different ending points of the same molecule. Barcodes can include a specific sequence within the molecule and a different ending sequence. For example, a molecule that is amplified from the same primer and has 25 nucleotide positions is different than a molecule that is amplified and has 27 nucleotide positions. The addition positions in the 27mer sequence can be considered a barcode. A barcode can be incorporated into a polynucleotide. A barcode can be incorporated into a polynucleotide by many methods. Some non-limiting methods for incorporating a barcode can include molecular biology methods. Some non-limiting examples of molecular biology methods to incorporate a barcode are through primers (e.g., tailed primer elongation), probes (i.e., elongation with ligation to a probe), or ligation (i.e., ligation of known sequence to a molecule).

A barcode can be incorporated into any region of a polynucleotide. The region can be known. The region can be unknown. The barcode can be added to any position along the polynucleotide. The barcode can be added to the 5' end of a polynucleotide. The barcode can be added to the 3' end of the polynucleotide. The barcode can be added in between the 5' and 3' end of a polynucleotide. A barcode can be added with one or more other known sequences. One non-limiting example is the addition of a barcode with a sequence adapter.

Barcodes can be associated with information. Some non-limiting examples of the type of information a barcode can be associated with information include: the source of a sample; the orientation of a sample; the region or container a sample was processed in; the adjacent polynucleotide; or any combination thereof.

Barcodes can be made from combinations of sequences (different from combinatorial barcoding) and can be used to identify a sample or a genomic coordinate and a different template molecule or single strand the molecular label and copy of the strand was obtained from. A sample identifier, a genomic coordinate and a specific label for each biological molecule may be amplified together. Barcodes, synthetic codes, or label information can also be obtained from the sequence context of the code (allowing for errors or error correcting), the length of the code, the orientation of the code, the position of the code within the molecule, and in combination with other natural or synthetic codes.

Incorporation of a barcode into a nucleic acid molecule indicates that the nucleic acid was present in a given sample at a given time period. Contiguous adjacent nucleic acid sequence sharing a common barcode or a common bar code pair is inferred to have been derived from a common molecule, particularly if the sample is diluted to less than an average of 2×, 1.5×, 1×, 0.7×, 0.5×, or 0.3× haploid genomes prior to barcode introduction.

Barcodes can be added before pooling of samples. When the sequences are determined of the pooled samples, the barcode can be sequenced along with the rest of the polynucleotide. The barcode can be used to associate the sequenced fragment with the source of the sample.

Barcodes can also be used to identify the strandedness sample. One or more barcodes can be used together. Two or more barcodes can be adjacent to one another, not adjacent to one another, or any combination thereof. Adapter orientation is often used to determine strandedness. For example, if an "A" adapter is always in the 5'-3' direction in a first primer extension reaction, then one can infer the read starting from the A adapter would be the compliment of the strand that was initially primed.

Barcodes can be used for combinatorial labeling.

As indicated herein, standard single-letter amino acid residue abbreviations as known in the art are used to refer to the twenty amino acids involved in cellular ribosomally driven polypeptide synthesis. Thus, "L372P" for example, refers to a Leucine to Proline missense mutation at position 372 of a polypeptide.

"Combinatorial labeling" is a method by which two or more barcodes are used to label. The two or more barcodes can label a polynucleotide. The barcodes, each, alone can be associated with information. The combination of the barcodes together can be associated with information. A combination of barcodes can be used together to determine in a randomly amplified molecule that the amplification occurred from the original sample template and not a synthetic copy of that template. The length of one barcode in combination with the sequence of another barcode can be used to label a polynucleotide. The length of one barcode in combination with the orientation of another barcode can be used to label a polynucleotide. In other cases, the sequence of one barcode can be used with the orientation of another barcode to label a polynucleotide. The sequence of a first and a second bar code, in combination with the distance in nucleotides between them, is used to label or to identify a polynucleotide. The sequence of a first and a second bar code, in combination with the distance in nucleotides between them and the identity of the nucleotides between them, is used to label or to identify a polynucleotide.

"Degenerate" can refer to a nucleic acid or nucleic acid region that is comprised of random bases, for example as determined by comparison to other constituents of a population sharing other common characteristics. The terms "degenerate" and "random" can be used interchangeably when referring to nucleic acid sequences (e.g., "degenerate primers" or "random primers" or "degenerate probes" or "random probes"). The degenerate region can be of variable length. The degenerate region can comprise some portion of the whole nucleic acid (e.g., a semi-degenerate primer). The degenerate region can comprise the whole nucleic acid (e.g., a "degenerate primer"). A degenerate nucleic acid mix, or semi-degenerate nucleic acid mix may be comprised of every possible combination of base pairs, less than every possible combination of base pairs, or some combination of base pairs, a few combinations of base pairs, or a single base pair combination. A degenerate primer mix, or semi-degenerate primer mix can comprise mixes of similar but not identical primers.

"Double-stranded" can refer to two polynucleotide strands that have annealed through complementary base-pairing, such as in a reverse-complementary orientation.

"Known oligonucleotide sequence" or "known oligonucleotide" or "known sequence" can refer to a nucleic acid fragment such as a polynucleotide or longer nucleic acid sample molecule having a total or partial sequence that is known. A known oligonucleotide sequence can correspond to an oligonucleotide that has been designed, e.g., a universal primer for next generation sequencing platforms (e.g., Illumina, 454), a probe, an adaptor, a tag, a primer, a molecular barcode sequence, an identifier. A known sequence can comprise part of a primer. A known oligonucleotide sequence may not actually be known by a particular user but can be constructively known, for example, by being stored as data which may be accessible by a computer. A known sequence may also be a trade secret that is actually unknown or a secret to one or more users but may be known by the entity who has designed a particular component of the experiment, kit, apparatus or software that the user is using.

"Library" can refer to a collection of nucleic acids. A library can contain one or more target fragments. The target fragments can be amplified nucleic acids. In other instances, the target fragments can be nucleic acid that is not amplified. A library can contain nucleic acid that has one or more known oligonucleotide sequence(s) added to the 3' end, the 5' end or both the 3' and 5' end. The library may be prepared so that the fragments can contain a known oligonucleotide sequence that identifies the source of the library (e.g., a molecular identification barcode identifying a patient or DNA source). Two or more libraries can be pooled to create a library pool. Libraries may also be generated with other kits and techniques such as transposon mediated labeling, or "tagmentation" as known in the art. Kits may be commercially available, such as the Illumina NEXTERA kit (Illumina, San Diego, Calif.).

"Locus specific" or "loci specific" can refer to one or more loci corresponding to a location in a nucleic acid molecule (e.g., a location within a chromosome or genome). Loci can be associated with genotype. Loci may be directly isolated and enriched from the sample, e.g., based on hybridization and/or other sequence-based techniques, or they may be selectively amplified using the sample as a template prior to detection of the sequence. Loci may be selected on the basis of DNA level variation between individuals, based upon specificity for a particular chromosome, based on CG content and/or required amplification conditions of the selected loci, or other characteristics that will be apparent to one skilled in the art upon reading the present disclosure. A locus may also refer to a specific genomic coordinate or location in a genome as denoted by the reference sequence of that genome.

"Long nucleic acid" can refer to a polynucleotide of at least 1, 2, 3, 4, 5, 6, 7, 8, 9, or 10 kilobases or longer.

The term "melting temperature" or "$T_m$" commonly refers to the temperature at which a population of double-stranded nucleic acid molecules becomes half dissociated into single strands. Equations for calculating the $T_m$ of nucleic acids are well known in the art. One equation that gives a simple estimate of the $T_m$ value is as follows: $T_m=81.5+16.6(\log 10[Na^+])0.41(\%[G+C])-675/n-1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references can include more sophisticated computations, which take structural as well as sequence characteristics into account for the calculation of $T_m$.

"Nucleotide" can refer to a base-sugar-phosphate combination. Nucleotides are monomeric units of a nucleic acid sequence (e.g., DNA and RNA). The term nucleotide includes naturally and non-naturally occurring ribonucleoside triphosphates ATP, TTP, UTP, CTG, GTP, and ITP, for example and deoxyribonucleoside triphosphates such as dATP, dCTP, dITP, dUTP, dGTP, dTTP, or derivatives thereof. Such derivatives can include, for example, [aS] dATP, 7-deaza-dGTP and 7-deaza-dATP, and, for example, nucleotide derivatives that confer nuclease resistance on the nucleic acid molecule containing them. The term nucleotide as used herein also refers to dideoxyribonucleoside triphosphates (ddNTPs) and their derivatives. Illustrative examples of dideoxyribonucleoside triphosphates include, ddATP, ddCTP, ddGTP, ddITP, ddUTP and ddTTP, for example.

"Polymerase" can refer to an enzyme that links individual nucleotides together into a strand, using another strand as a template.

"Polymerase chain reaction" or "PCR" can refer to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, can be amplified to obtain thousands, millions, or billions of replicates. The polymerase chain reaction can be used to detect and measure very small amounts of DNA and to create customized pieces of DNA.

The term "polynucleotides" or "nucleic acids" may include but is not limited to various DNA, RNA molecules, derivatives or combination thereof. These may include species such as dNTPs, ddNTPs, DNA, RNA, peptide nucleic acids, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA.

A "primer" generally refers to an oligonucleotide used to, e.g., prime nucleotide extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific nucleic acid region.

"Primer extension product" can refer to the product resulting from a primer extension reaction using a contiguous polynucleotide as a template, and a complementary or partially complementary primer to the contiguous sequence.

"Sequencing," "sequence determination," and the like generally refers to any and all biochemical methods that may be used to determine the order of nucleotide bases in a nucleic acid.

A "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

The term "biotin," as used herein, is intended to refer to biotin (5-[(3aS,4S,6aR)-2-oxohexahydro-1H-thieno[3,4-d] imidazol-4-yl]pentanoic acid) and any biotin derivatives and analogs. Such derivatives and analogs are substances which form a complex with the biotin binding pocket of native or modified streptavidin or avidin. Such compounds include, for example, iminobiotin, desthiobiotin and streptavidin affinity peptides, and also include biotin-.epsilon.-N-lysine, biocytin hydrazide, amino or sulfhydryl derivatives of 2-iminobiotin and biotinyl-ε-aminocaproic acid-N-hydroxysuccinimide ester, sulfo-succinimide-iminobiotin, biotin-bromoacetylhydrazide, p-diazobenzoyl biocytin, 3-(N-maleimidopropionyl) biocytin. "Streptavidin" can refer to a protein or peptide that can bind to biotin and can include: native egg-white avidin, recombinant avidin, deglycosylated forms of avidin, bacterial streptavidin, recombinant streptavidin, truncated streptavidin, and/or any derivative thereof.

An "RNA promoter" as used herein is a DNA molecule that directs an RNA polymerase to initiate transcription.

A "subject" generally refers to an organism that is currently living or an organism that at one time was living or an entity with a genome that can replicate. The methods, kits, and/or compositions of the disclosure can be applied to one or more single-celled or multi-cellular subjects, including but not limited to microorganisms such as bacterium and yeast; insects including but not limited to flies, beetles, and bees; plants including but not limited to corn, wheat, seaweed or algae; and animals including, but not limited to: humans; laboratory animals such as mice, rats, monkeys, and chimpanzees; domestic animals such as dogs and cats, agricultural animals such as cows, horses, pigs, sheep, goats; and wild animals such as pandas, lions, tigers, bears, leopards, elephants, zebras, giraffes, gorillas, dolphins, and whales. The methods of this disclosure can also be applied to germs or infectious agents, such as viruses or virus particles or one or more cells that have been infected by one or more viruses.

A "support" can be solid, semisolid, a bead, a surface. The support can be mobile in a solution or can be immobile.

The term "unique identifier" may include but is not limited to a molecular bar code, or a percentage of a nucleic acid in a mix, such as dUTP.

"Repetitive sequence" as used herein refers to sequence that does not uniquely map to a single position in a nucleic acid sequence data set. Some repetitive sequence can be conceptualized as integer or fractional multiples of a repeating unit of a given size and exact or approximate sequence.

A "palindrome" or "palindromic sequence" as used herein refers to a nucleic acid sequence that is the same whether read 5' (five-prime) to 3' (three prime) on one strand or 5' to 3' on the complementary strand with which it forms a double helix.

An "inverted sequence" as used herein refers to a sequence that is the reverse sequence or reverse complement sequence relative to another sequence. A sequence is inverted if, upon (conceptually) rotating the molecule on which it is found by 180 degrees, the sequence as read in the same direction is the same sequence.

A "haplotype" as used herein refers to a collection of specific alleles in a cluster of tightly-linked genes on a chromosome that are likely to be inherited together.

A "sub-haploid" fraction as used herein refers to a genomic sample that is diluted to or that otherwise comprises less than one haploid complement of nucleic acid material.

The term "about" as used herein in reference to a number refers to a set including that number plus a range of values spanning plus or minus 10% of that number.

Before the present methods, compositions and kits are described in greater detail, it is to be understood that this invention is not limited to particular method, composition or kit described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, compositions and kits are provided for producing multi-insert nucleic acids. These methods, compositions and kits find use in a number of application, such as whole-genome sequencing. These and other objects, advantages, and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I. Methods of Insertional Modification of Nucleic Acids & in Silico Sequencing

A. Introducing Insertional Nucleic Acids into Target Nucleic Acids to Produce Multi-Insert Nucleic Acids Disclosed herein are methods of generating a plurality of multi-insert nucleic acids, the methods comprising combining: an insertional nucleic acid that comprises an RNA polymerase promoter flanked by nucleic acid integrase recognition sequences; a plurality of target nucleic acids; and a nucleic acid recombinase such as a transposase, wherein the nucleic acid integrase cleaves one or more of the plurality of target nucleic acids to produce one or more recombination sites within the target nucleic acids; recognizes the nucleic acid integrase recognition sequences; and inserts the insertional nucleic acid into the one or more insertion sites to generate the plurality of multi-insert nucleic acids. Conditions for transposase or other recombinase or invertase activity are known to those of skill in the art.

Insertion reactions are performed using reagents at concentrations so as to effect a desired insertion density in the sample. Desired insertion densities vary, but are often in the range of one insert for each 500 bp to 2 kb, 3 kb, 4 kb, or 5 kb or greater. Desired insertion density often varies with RNA synthesis extension success, such that conditions resulting in longer RNA intermediate molecules, such as 10 kb, 20 kb, 30 kb or greater, facilitate less dense insertion events. In alternate cases, the one or more insertion sites are separated by an average distance selected from less than 100 bp, less than 200 bp, less than 300 bp, less than 400 bp, less than 500 bp, less than 600 bp, less than 700 bp, less than 800 bp, less than 900 bp, less than 1000 bp, less than 1100 bp, less than 1200 bp, less than 1300 bp, less than 1400 bp, less than 1500 bp, less than 1600 bp, less than 1700 bp, less than 1800 bp, less than 1900 bp, less than 2000 bp, less than 2100 bp, less than 2200 bp, less than 2300 bp, less than 2400 bp, less than 2500 bp, less than 2600 bp, less than 2700 bp, less than 2800 bp, less than 2900 bp and less than 3000 bp. In some cases, insertion sites are separated by an average distance of about 500 bp. In some cases, insertion sites are separated by an average distance of about 1000 bp. In some cases, insertion sites are separated by an average distance of about 1500 bp. In some cases, insertion sites are separated by a distance dependent on the ratio of target nucleic acid to integrase.

Target Nucleic Acids

The methods disclosed herein comprise insertional modification of one or more target nucleic acids. Exemplary target nucleic acid comprises DNA, such as double stranded DNA. Target nucleic acid(s) often comprise genomic DNA, or cDNA libraries or other DNA sources. A wide range of organisms are suitable sources for genomic DNA, such as eukaryotic, eubacterial or archaeal sources. Non-limiting sample sources include animal DNA, plant DNA, or generally, DNA is isolated from a biological sample such as a blood sample, a bodily fluid sample, a hair sample, a skin sample, a saliva sample, etc., as indicated elsewhere herein and as contemplated by one of skill in the art.

Target nucleic acids can be obtained from a population of cells. For example some target nucleic acids are obtained from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cells, or more than 100 cells. The methods and compositions herein are consistent with obtaining target nucleic acids from a single cell, and even subdividing the target nucleic acids into sub genomic fractions.

Target nucleic acids are provided at an amount selected from about 1 pg, 2 pg, 3 pg, 3.2 pg, 4 pg, 5 pg, 6 pg, 7 pg, 8 pg, pg, 10 pg, 20 pg, 30 pg, 40 pg, 50 pg, 60 pg, 70 pg, 80 pg 90 pg, 100 pg, 200 pg, 300 pg, 400 pg, 500 pg, 600 pg, 700 pg, 800 pg, 900 pg, 1 ng, 2 ng, 3 ng, 4 ng, 5 ng, 6 ng, 7 ng, 8 ng, 9 ng, 10 ng, 11 ng, 12 ng, 13 ng, 14 ng, 15 ng, 16 ng, 17 ng, 18 ng, 19 ng, 20 ng, 21 ng, 22 ng, 23 ng, 24 ng, 25 ng, 26 ng, 27 ng, 28 ng, 29 ng, 30 ng, 31 ng, 32 ng, 33 ng, 34 ng, 35 ng, 36 ng, 37 ng, 38 ng, 39 ng, 40 ng, 41 ng, 42 ng, 43 ng, 44 ng, 45 ng, 46 ng, 47 ng, 48 ng, 49 ng, 50 ng, 51 ng, 52 ng, 53 ng, 54 ng, 55 ng, 56 ng, 57 ng, 58 ng, 59 ng, 60 ng, 61 ng, 62 ng, 63 ng, 64 ng, 65 ng, 66 ng, 67 ng, 68 ng, 69 ng, 70 ng, 71 ng, 72 ng, 73 ng, 74 ng, 75 ng, 76 ng, 77 ng, 78 ng, 79 ng, 80 ng, 81 ng, 82 ng, 83 ng, 84 ng, 85 ng, 86 ng, 87 ng, 88 ng, 89 ng, 90 ng, 91 ng, 92 ng, 93 ng, 94 ng, 95 ng, 96 ng, 97 ng, 98 ng, 99 ng or 100 ng, and a value outside of the range defined by the above-mentioned list. Often, the target nucleic acids are obtained/provided at an amount of about 50 ng.

One library generation approach comprises isolating 10-20 cells worth of DNA, subjecting the DNA to an insertion treatment, then size selecting and diluting the sample into droplets. In vitro transcription and optionally reverse transcription using barcoded primers is performed in the droplets. Other partitions, such as microwells, are also contemplated and consistent with the disclosure herein.

Alternately, a single cell nucleic acid complement is obtained and subjected to insertion treatment as disclosed herein or as understood by one of skill in the art. The inserted sample is then diluted into sub genomic fractions that serve as starting points for library generation. Sub genomic fractions are partitioned into droplets, wells, microwells or other partitions, and then subjected to library generation via in vitro transcription or other nucleic acid extension as disclosed herein. Starting with single cell nucleic acid genomes has an advantage over starting with bulked multi-cell nucleic acid samples and aliquotting single-cell equivalent or sub-cellular equivalents because bulking and dilution runs the risk that, by chance, some regions of a genome will be over-represented or underrepresented in the aliquots.

Insertional Nucleic Acids

Disclosed herein are methods of inserting an insertional nucleic acid into a target nucleic acid. Some methods comprise introducing a plurality of insertional nucleic acids into a target nucleic acid. Often, each insertional nucleic acid of the plurality of insertional nucleic acids consists of a same sequence. Alternatively, one or more of the insertional nucleic acids of the plurality of insertional nucleic acids consist of a different sequence.

Some insertional nucleic acids disclosed herein have a minimal nucleotide length while having the ability to insert into a target nucleic acid. For example, core insertional nucleic acids have a left border nucleic acid, an RNA promoter such as a T7, T3, or SP6 promoter and a right border nucleic acid. Some insertional nucleic acid described herein are transposable nucleic acid elements, such as a Tn5 transposon comprising the necessary left and right mosaic end sequences necessary for transposition and an RNA promoter, such as a T7, T3, or SP6 promoter. Insertional nucleic acids optionally comprise a tag sequence. In some cases, the insertional nucleic acid comprises two RNA promoters, such as two T7, T3, or SP6 promoters which direct transcription in opposite directions. In some cases, the insertional nucleic acid comprises two different RNA promoters, such as a T7 and a T3, a T7 and a SP6, or a T3 and a SP6 promoter which direct transcription in opposite directions. Such insertional nucleic acids allow from RNA transcription to occur in two directions from one location in the target nucleic acid. This is particularly useful when sequencing certain types of target nucleic acid such as repeat regions and telomeres.

A number of insertion nucleic acid fragments are consistent with the disclosure herein. A core nucleic acid fragment comprises a left and right border required for transposase binding, transpososome assembly, and insertion into a sample such as a genomic nucleic acid sample, and also comprises an RNA polymerase promoter sequence. Thus, in preferred minimal insertion fragment examples, an insert comprises 60 or fewer base pairs, comprising a first transposase border of as few as 23, 22, 21, 20, 19, 18, 17 bases or fewer, an RNA promoter such as a T7 promoter of 25, 24, 23, 22, 21, 20, 19, 18, 17 or fewer bases, and a second transposase border, for a total in some cases of fewer than 60 bases. Small inserts are preferred because they occupy a smaller proportion of the total sequence reads of the sample when formatted into a sequencing library and sequenced, although in alternate cases a larger insert comprising additional nucleic acid sequence or information is employed The insertional nucleic acid ends comprise mosaic ends (ME) or other sequence ends that are recognized by the transposase or other insertional enzymes and required for insertion.

Nested between mosaic ends are found one or more RNA polymerase promoters or other sequence. As discussed herein, T7, T3, and SP6 are preferred in many cases, but a broad range of RNA promoters are contemplated, including T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, U6, and other RNA promoters known in the art.

In minimal insert examples, the insert comprises a single RNA promoter bounded by an ME or other transposase or invertase or recombinase sequence at either end. In these examples insert size is minimized, for example to minimize the amount of insertion sequence in the final sequenced library. Alternately, insertions further include a second RNA polymerase promoter site, such as a site positioned antiparallel to the first so that they direct RNA polymerase extension in opposite directions from the insertion. Such a configuration effectively doubles the number of RNA intermediates generated from a single whole-sample insertion event. Insertions optionally include a barcode sequence, optionally positioned so as to be transcribed, so that the transcription fragments are differentially barcoded by insertion sequence. In alternate embodiments or in combination, library constituents are barcoded through downstream processing of the library RNA intermediates such as during their reverse-transcription into a DNA library.

Some alternative insertion strategies involve insertion populations, whereby the majority of inserts are as described above, but are provided with a percentage of 'gapped' inserts whereby the left and right borders are not connected in a loaded transposon. These gapped inserts are effective if some sample fragmentation is desired, as their insertion results in breakage and local loss of phase information. In some cases gapped inserts are employed at a frequency of 1%, 2%, 3%, 4%, 5%, 6%, 7%, 8%, 9%, 10% or other proportion of the total insert population.

Some alternative insertion strategies involve inserts having transcription termination sites upstream of the promoter sequence, so as to prevent read-through from transcripts extending from upstream of the promoter. Such inserts are preferred if one wants to limit overall or average transcript extension. Much like the 'gapped' inserts, above, inserts having transcription termination sites are often used in insertion populations, for example at a frequency of 1%, 2%, 3%, 4%, 5%, 6%, 7%, 8%, 9%, 10% or other proportion of the total insert population Some alternate embodiments rely upon primer annealing and extension rather than RNA polymerase-driven RNA synthesis alone. These embodiments comprise one or more of the following elements, alone or in combination. The double stranded insertional nucleic acid comprises an adapter sequence between the mosaic ends. The adapter sequence comprises a first adapter sequence and a second adapter sequence. Thus, the methods result in producing multiple contiguous DNA sequences, where the inverted adapter sequences are split by stretches of gDNA of a desired length (e.g. 5'-19 bp ME←-adapter-B adapter→-gDNA insert-19 bp ME-←FA adapter-B adapter→ . . . repeat N times through full length contiguous sequence). The primer binding site and the ME sequence may overlap. Some insertion sequences additionally have a tag sequence adjacent to the ME sequence such that amplification from the primer results in an amplicon having a barcode sequence. The barcode sequence is unique to the insert, or alternatively is common to all inserts introduced at a given iteration of an iterative insertion process. The first adapter sequence and the second adapter sequence are arranged in an inverted configuration (e.g. inverted adapter sequences) or a palindromic configuration. The adapter sequences may comprise a primer annealing sequence. Primers that anneal to the adapter sequences are designed to amplify the genomic DNA between the insertional sequences, as indicated by the arrows in the example above. Some primers comprise a tag. The tag is optionally specific to a subset of the genomic DNA. Some methods comprise sequencing the amplified genomic DNA. Sequencing may comprise a next generation sequencing (NGS) method or modification thereof.

Some insertion nucleic acid fragments are synthesized to include a preferred restriction endonuclease or other cleavage site, so that nucleic acid samples treated with an insert can be cleaved at insertion sites.

Thus, both preferred RNA polymerase promoter-directed library generation and primer-extension mediated library generation are contemplated herein. These approaches are not mutually inconsistent, as RNA polymerase promoter regions are also suitable primer binding sites.

Transposase

Methods disclosed herein comprise inserting an insertion fragment such as those discussed herein into a nucleic acid sample. A number of approaches to insertion into the sample are compatible with the disclosure herein, including enzymatic insertion, for example through use of a recombinase, an invertase or a transposase.

Some methods herein use a transposase to treat the target nucleic acids. Methods consistent with the disclosure herein incorporate one or a plurality of consistent elements as recited below and herein. Often, an enzyme is selected to so as not to fragment or otherwise damage the target nucleic acids aside from the insertion process. The transposase reaction is often conducted in a minimal amount of time in order to obtain a density of transposition events at one insertion per 500 to 2000 base pairs, or 3000 base pairs, 4000 base pairs, 5000 base pairs or greater than 5000 base pairs. The transposase binds an insertional nucleic acid and catalyzes insertion or movement of the insertional nucleic acid into a target nucleic acid (e.g. genomic DNA). Some exemplary transposases have DNase activity. Some of the transposases have RNase activity. The transposase often has integrase activity. A retroviral integrase or an enzyme possessing this activity is consistent with the methods herein. A polynucleotidyl transferase is consistent with the methods herein. The transposase is optionally an *Escherichia* bacterial transposase. The transposase is optionally a *Shewanella* bacteria transposase. An exemplary transposase is Tn5 transposase. Some transposase examples demonstrate at least 10%, 15%, 20%, 25%, about 30%, 35%, 40%, 45%, 50%, 55%, 60%, 65%, 70%, 75%, 80%, 85%, 90%, 95% or 99% or greater sequence identity to a Tn5 transposase. Some transposases comprises at least one mutation relative to Tn5, such as a mutation that increases the catalytic activity of the transposase. Some exemplary mutations include L372P, using standard one letter nucleic acid abbreviations. Some transposases comprise a DDE motif, understood cases to comprise an aspartate at amino acid 97, an aspartate at amino acid 188 and a glutamate at amino acid 326 in standard numberings of transposases such as Tn5. Alternately, the DDE motif is mutated to an EED motif (e.g. the aspartates are mutated to glutamates and the glutamate is mutated to aspartate at amino acids 97, 188 and 326, respectively). Alternately, the transposase comprises a DDD motif, or a DEE motif, or an EEE motif. A compatible transposase is a Tc1/mariner-type transposase. Another compatible transposase is a sleeping beauty transposase, such as the sleeping beauty transposase is SB100X. Alternately or in combination, the transposase demonstrates at least 10%, 15%, 20%, 25%, about 30%, 35%, 40%, 45%, 50%, 55%, 60%, 65%, 70%, 75%, 80%, 85%, 90%, 95% or 99% or greater sequence identity to SB100X sleeping beauty transposase.

Alternative approaches to sample insertion are consistent with the methods herein. In some cases an important feature of the insertion approach is that it preserves phase information of the nucleic acid molecules into which the inserts are introduced. Although transposase treatment accomplishes this goal, other approaches are similarly contemplated, and any number of approaches that effect insertion at random or otherwise at the desired densities, in some cases without impacting nucleic acid phase information, are contemplated herein and are consistent with the libraries presented herein.

In some alternatives, promoter sequences can be inserted using for example, a nuclease that chews back at a nicked site exposing single stranded genomic DNA. Then a T7 promoter sequence with a random primer can be hybridized. The chewed back portion can then be extended and ligated to the 5' end of T7 promoter. Alternatively, long molecules (10-100 kb) of genomic DNA can be ligated to T7 promoter sequences to effectively introduce the promoter sites randomly within the genome.

Other Reagents for Insertion Reaction

The methods disclosed herein comprise combining the integrase such as a transposase, the insertional nucleic acid(s) and target nucleic acid(s) in a reaction buffer. Buffers consistent with the disclosure herein often comprises magnesium and are devoid of sodium diethyl sulfate (SDS), as SDS may denature the integrase (e.g. transposase). A number of transposase reaction conditions are known in the art, and the disclosure herein is consistent with a plurality of variations on reaction conditions.

Ratios of Transposase Enzyme to Insertional Nucleic Acids & Target Nucleic Acids A number of ratios are contemplated herein. Generally, reagents are selected to effect local insertion densities of about 500 bp to 2 kb within a sample nucleic acid molecule. Often reagents are selected to effect global insertion densities of about 500 bp to 2 kb within a sample nucleic acid molecule, or within each nucleic acid molecule in a sample. Reagents are optionally selected to effect local or global insertion densities of about 500 bp to 5 kb. Often, reagents are selected to effect local or global insertion densities of about 400 bp, 500 bp, 600 bp, 700 bp, 800 bp, 900 bp, 1 kb, 1.2 kb, 1.4 kb, 1.5 kb, 1.7 kb, 1.8 kb, 2 kb, 2.5 kb, 3 kb, 3.5 kb, 4 kb, 4.5 kb, 5 kb, 5.5 kb, 6 kb, 6.5 kb, 7 kb, 8 kb, 9 kb, or 10 kb within a sample nucleic acid molecule or within each nucleic acid molecule in a sample. An insertion density is sometimes chosen based on the length of RNA transcript produced by an RNA polymerase. An average RNA transcript may have a length of about 2 kb to 10 kb of nucleotides, or a mean of about, 5-8 kb but may range between 1000 and 20,000 nucleotides in length. An insertion density is chosen to have sufficient overlap to allow sequences to be assembled into contigs. Optionally, density is selected to minimize the overlap between RNA transcripts so as to minimize sequence redundancy. Generally, insertion densities of substantially more dense than one insertion per 500 bp result in substantial redundancy of sequence information obtained.

B. Diluting Multi-Insert Nucleic Acids

Some methods disclosed herein comprise diluting multi-insert nucleic acids into a plurality of containers, to produce a first plurality of diluted multi-insert nucleic acids in a first container and a second plurality of diluted multi-insert nucleic acids in a second container.

The extent of dilution varies according to the eventual objectives for the library. If the library is intended to be used for phase determination, then there are benefits in minimizing the chance that two parental chromosomes will be partitioned into the same compartment. Having two parental chromosomes in a single partition does not preclude phase determination, but the data from these co-diluted chromosomes may be contradictory, and may be excluded from the final analysis.

When the library is intended for de novo genome assembly, the differential segregation of parental chromosomes is not necessarily a priority. In these cases, a priority is often to minimize the amount of DNA per barcode so as to facilitate sequence assembler activity. Co-segregation of two parental chromosomes into a de novo genome assembly may lead to a branched assembly, but one that is likely to be resolved using barcoded reads from other dilutions.

Accordingly, some methods comprise diluting multi-insert nucleic acids, wherein the multi-insert nucleic acids comprise genomic DNA. Some methods comprise diluting the multi-insert nucleic acids comprising genomic DNA into a plurality of containers, such that no two containers contain the same chromosome. Some methods comprise diluting the multi-insert nucleic acids comprising genomic DNA into a plurality of containers, such that no two containers contain identical samples. Some methods comprise diluting the multi-insert nucleic acids comprising genomic DNA into a plurality of containers, such that the likelihood that two containers contain the same genomic sample sequence is very low. Some methods comprise diluting the multi-insert nucleic acids comprising genomic DNA into a plurality of containers, such that the likelihood that two containers contain the same haplotype is a percentage selected from less than about 1%, less than about 2%, less than about 3%, less than about 4%, less than about 5%, less than about 6%, less than about 7%, less than about 8%, less than about 9%, less than about 10%. Some methods comprise diluting the multi-insert nucleic acids comprising genomic DNA into a plurality of containers, such that the likelihood that two containers contain the same haplotype or sub-haploid fraction is a percentage selected from less than about 5%, less than about 10%, less than about 15%, less than about 20%, less than about 25%, less than about 30%, less than about 35%, less than about 40%, less than about 45% and less than about 50%.

Some methods comprise diluting the multi-insert nucleic acids comprising genomic DNA into a plurality of containers, such that the haplotype frequency in a container is very low. The haplotype frequency in a container is very low if there is less than about 10, less than about 5, less than about 4, less than about 3, less than about 2 or less than about 1 copy of a haplotype in each container of the plurality of containers.

Some methods comprise diluting multi-insert nucleic acids into a plurality of containers, such that each container of the plurality of containers contains less than about 1000, less than about 500, less than about 200, less than about 100, less than about 50, less than about 20 or less than about 10 multi-insert nucleic acids. Some methods comprise diluting multi-insert nucleic acids into a plurality of containers, such that each container of the plurality of containers does not contain more than one multi-insert nucleic acid.

Containers

Some methods disclosed herein comprise diluting multi-insert nucleic acids into a plurality of containers. The plurality of containers may comprise a container selected from a tube, a well, a microwell, a nanowell, droplet, a microdroplet, or an otherwise spatially separated compartment.

Methods disclosed herein comprise conducting the reaction which inserts the insertional nucleic acid, or "transposon," into the target nucleic acid, for example a transposase reaction, in the same container as the amplification of the template, for example by in vitro transcription. Often, this "one pot reaction" has the benefit of minimizing the manipulation steps of the sample and target nucleic acid which maintains the structural integrity of the sample target nucleic acid.

The container is often part of a solid support. The solid support may be selected from a rack, a chip, a column, a slide, a wafer, and a bead. Optionally, the bead comprises streptavadin. Some methods further comprise incorporating a biotin molecule into the multi-insert nucleic acids.

The container is optionally a plate. An example is a microplate, having a container that is a microwell. Often, the microplate comprises about 96 microwells, about 384 microwells, about 1536 microwells, about 3456, or about 9600 wells Containers may have a volume of 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, or 30 µL. Often, the containers have a volume of 10 µL, 15 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 954 or 100 µL. Alternately, the volume of the container is about 2 µL. The volume of the container is about 55 µL in other cases. Alternately, the volume of the container is about 330 µL. Some container volumes are on a nanoliter scale. Alternately, some container volumes are on a picoliter scale.

C. Washing

Some methods disclosed herein comprise washing the multi-insert nucleic acids to remove excess insertional nucleic acids and/or the integrase (e.g. transposase) after introducing the insertional nucleic acids into the target nucleic acid(s) to produce the plurality of multi-insert nucleic acids. Washing optionally occurs before diluting the plurality of multi-insert nucleic acids into a plurality of containers, or may occur after diluting the plurality of multi-insert nucleic acids into a plurality of containers.

Optionally, intermediate libraries are treated to remove the original nucleic acids prior to reverse transcription. This is accomplished through DNase treatment of the sample comprising the amplified RNA intermediate library and the original DNA, followed by, for example, heat inactivation of the DNase activity.

D. Amplification and Tagging of Multi-Insert Nucleic Acids & Fragments Thereof

Provided herein are methods of amplification of a target nucleic acid to synthesize a library, wherein the target sequence comprises at least one insertional nucleic acid. Methods of amplification amplify 50%, 55%, 60%, 65%, 70%, 75%, 80%, 85%, 90%, 91%, 92%, 93%, 94%, 95%, 96%, 97%, 98%, 99%, 99.5%, 99.9% or 100% of the sequence information of a nucleic acid sample such as a genomic sample. For example, the target nucleic acid often comprises a genome of a cell. Some genomic samples comprise at least 100,000 kb, 500,000 kb, 1 Mb., 1.5 Mb, 2 Mb, 5 Mb, 10 Mb, 20 Mb, 50 Mb, 100 Mb, 200 Mb, 500 Mb, 1,000 Mb or greater. Some methods provided herein amplify at least 90% of the genome of a cell, such as a human cell.

Amplification up to the percentages contemplated herein are accomplished at high levels of amplification, such that a sample as small as a sub genomic sample from a single cell or a bulk sample from a large number of cells is amplified may-fold in library generation, such as 10×, 20×, 50×, 100×, 200×, 500×, 1000×, 2000×, 5000×, 10000×, 20000×, 50000×, 100000×, 200000×, 500000×, 1,000,000×, 2,000,000×, 5,000,000× or greater than 5,000,000×. In some cases amplification is at least 1000×.

Amplification through the methods herein result in strikingly unbiased, uniform amplification of the sample, such that amplification is not skewed toward on or another region of a sample. Amplification variously results in 50%, 55%, 60%, 65%, 70%, 75%, 80%, 85%, 90%, 91%, 92%, 93%, 94%, 95%, 96%, 97%, 98%, 99%, 99.5%, 99.9% greater of the amplified library is amplified such that library members are present at a level of at least ¼ of the mean or median library constituent level.

That is, methods herein amplify a sample such that at least 90% of the sample is amplified at least 1000×, and such that the amplification is uniform to the point that 85% of the amplified sample is present at within 1/× to 4× the mean or median level of the amplified sample.

In the alternative, some methods comprise incubating the diluted plurality of multi-insert nucleic acids with a pair of PCR primers. One or both of the PCR primers can comprise a tag specific to an individual container, well or compartment ("container-specific tag"). In some cases, each PCR primer of the pair of PCR primers comprises the container-specific tag. In some cases, each PCR primer of the pair of PCR primers comprises a same container-specific tag. In some cases, each PCR primer of the pair of PCR primers comprises a different container-specific tag.

F. Sequencing Target Nucleic Acids

Some methods disclosed herein comprise sequencing the multi-insert nucleic acids and/or multi-insert nucleic acid fragments. A number of sequencing methods are known to one of skill in the art. Methods of sequencing nucleic acids disclosed herein also include methods described in PCT application number PCT/US2015/049249 filed Sep. 9, 2015 which is hereby incorporated by reference in its entirety.

Some methods further comprise pooling amplified target nucleic acids or amplified target nucleic acid fragments from two more containers before sequencing. Some methods further comprise pooling the amplified multi-insert nucleic acids or amplified multi-insert nucleic acid fragments from two more containers before sequencing. The sequencing may read the tag of an amplified multi-insert nucleic acid/target nucleic acid, thereby identifying the container from which it was pooled.

Some methods comprise annealing an oligonucleotide required for sequencing to the multi-insert nucleic acids or multi-insert nucleic acid fragments. Some sequencing comprises ligating an oligonucleotide required for sequencing to the multi-insert nucleic acids or multi-insert nucleic acid fragments. Some methods comprise utilizing the adapter sequence or portion thereof to sequence the multi-insert nucleic acids or multi-insert nucleic acid fragments.

Methods of nucleic acid sequencing are well-known and described thoroughly in the art. The methods disclosed herein may comprise any standard or known method of sequencing.

Determination of the sequence of an amplified nucleic acid may be performed using a sequencing method selected from a variety of sequencing methods including, but not limited to, ion detection technology, DNA nanoball technology, nanopore-based sequencing technology, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods such as cyclic array sequencing using platforms such as Roche 454, Illumina Solexa, ABI-SOLiD, ION Torrents, Complete Genomics, Pacific Bioscience, Helicos, Polonator platforms, are consistent with the disclosure herein.

Determination of the sequence of an amplified nucleic acid performed by a next-generation sequencing (NGS) method is consistent with the disclosure herein. NGS applies to genome sequencing, genome resequencing, transcriptome profiling (RNA-Seq), DNA-protein interactions (ChIP-sequencing), and epigenome characterization. Some methods disclosed herein comprise an NGS method selected from, but are not limited to, massively parallel signature sequencing (MPSS), Polony sequencing, 454 pyrosequencing, Ion Torrent semiconductor sequencing, Heliscope single molecule sequencing, single molecule real time (SMRT) sequencing and microfluidic Sanger sequencing.

G. Linking Sequences Together

Some methods disclosed herein further comprise determining the phase of resulting sequences. Methods may comprise aligning a first sequence and second sequence according to an overlapping sequence common to the first sequence and the second sequence.

Often, the multi-insert nucleic acids are diluted into a container before amplification/sequencing, such that the likelihood of sequencing two different haplotypes or two different alleles from a single partition or container is very small.

Often, the multi-insert nucleic acids are diluted into a container before amplification/sequencing, and more than one copy of a haplotype or allele are diluted into a first container. The more than one copy may originate from a same chromosome, or may originate from a different chromosome.

H. Sequencing Low Complexity and Repetitive Target Nucleic Acids

A benefit of methods and libraries disclosed herein is that they facilitate sequencing of genomic nucleic acid samples, including samples having locally or globally repetitive regions. That is, regions comprising a sequence unit that is completely or incompletely repeated at a single locus or at multiple discrete loci are accurately sequenced using methods or compositions as disclosed herein.

Current methods of sequencing are unable to accurately provide a sequence in such nucleic acid regions because, some regions comprise a repetitive sequence and such nucleic acid sequences are difficult to assemble. Most alternative approaches may identify repetitive regions, but do not accurately establish the number of or sequence of the repeats of a given locus, and often are unable to assign a point mutation to one rather than another monomer of a repeat region or to a repeat region at one or another locus.

Though the practice of the methods herein, an insertion nucleic acid fragment is introduced at positions distributed throughout a nucleic acid sample, such that inserts are distributed at a density of about 1 every 500 pb to 2 kb, 3 kb, 4 kb 5 kb or greater than 5 kb. Importantly, insertion site determination is largely or completely independent of sample nucleic acid sequence, such that the insertion distribution patter is independent of the underlying sample nucleic acid sequence. As a result regions of a sample that are repetitive and therefore difficult to sequence at a given locus, or difficult to assign to one or another repetitive locus of a genome, are provided with an overlying 'barcode' or 'insertion fingerprint' of insertion fragment sequence, such that the combination of underlying sample sequence and inserted sequence such as ME borders and RNA polymerase primer sequence is no longer repetitive.

Advantages provided by methods described herein include providing a fingerprint by inserting an insertional nucleic acid into the target nucleic acid. This insertion occurs in several locations across the region, providing a common locus by which to place sequence reads when assembling the sequence data.

Accordingly, sequence reads that would otherwise map to multiple loci or map only to a single, highly overrepresented repeat monomer, are mapped according to their start position and 5' insert sequence to a specific insertion site within a repetitive region. Furthermore, RNA transcription products directed by adjacent insertion events will often span an insert in a repetitive region, such that insertion site sequences in their local sequence context are obtained through sequencing of a library as generated herein. Accordingly, repeat region sequence is mapped according to its sequence start site and according to insertion sites as indicated by additional RNA intermediate reads, such that repeat region sequences are mapped to their locus in a nucleic acid sample sequence such as a genomic sample, rather than mapping to, for example, a single, highly covered but poorly assembled monomer of a repeat sequence.

Thus, repetitive sequence of a nucleic acid sample is sequenced by inserting a plurality of nucleic acid inserts into nucleic acid encoding the repetitive sequence, generating library constituents anchored by the plurality of nucleic acid inserts, sequencing the library constituents and assembling sequences of the library constituents such that sequence reads having repetitive region sequence and insert sequence having common junctions are assembled to common loci. The nucleic acid inserts in many cases comprise RNA polymerase promoter sequence, such that they direct synthesis of a population of RNA molecules spanning the promoter sequence, adjacent ME sequence, and insertion-adjacent repetitive nucleic acid sequence. RNA molecules synthesized hereby comprise insertion sequence, insertion adjacent repetitive sequence and often span at least one adjacent insertion site, and in some cases span at least one repetitive junction to nonrepetitive genomic or other sample sequence. Accordingly, regions that are otherwise partially or completely composed of repetitive nucleic acid sequence are rendered nonrepetitive through the introduction if insertion sequence at random in a plurality of repeated monomer sequences in a nucleic acid sample.

II. Compositions

A. Long Contiguous Multi-Insert Nucleic Acids

Disclosed herein are long contiguous multi-insert nucleic acids comprising a target nucleic acid and a plurality of insertional nucleic acids, wherein the plurality of insertional nucleic acids are distributed at a plurality of sites throughout the target nucleic acid. Insertional nucleic acids often comprise a minimal nucleic acid length, such as to minimize the amount of non-target nucleic acids in the composition. The adapter sequence often comprises at least one transcriptional promoter. Optionally, the adaptor sequence comprising two transcriptional promoters is arranged such that each transcriptional promoter is directed outward such that an RNA transcript can be made outward from each insertional nucleic acid. In some cases, the transcriptional promoter is recognized by an RNA polymerase. Exemplary RNA polymerases include T7, T3, and SP6 polymerases. The insertional nucleic acid often comprises a mosaic end, wherein the mosaic end is recognized by a transposase. The insertional nucleic acid often comprises a first mosaic end and a second mosaic end that flank the adapter sequence.

The treated target nucleic acid comprises a plurality of target nucleic acid fragments separated by one or more of the insertional nucleic acids of the plurality of insert insertional nucleic acids. Optionally, one or more of the plurality of insertional nucleic acids alternates with one or more of the plurality of target nucleic acid fragments. One or more of the plurality of insertional nucleic acids may be contiguous with the one or more of the plurality of target nucleic acid fragments.

An insertional nucleic acid of the plurality of insertional nucleic acids occurs at an average frequency of about 500 base pairs to about 2000 base pairs within the target nucleic acid in preferably treated samples. In some cases, an insertional nucleic acid of the plurality of insertional nucleic acids occurs at an average frequency of about 500 base pairs within the target nucleic acid. In some cases, an insertional nucleic acid of the plurality of insertional nucleic acids occurs at an average frequency of about 600 base pairs within the target nucleic acid. In some cases, an insertional nucleic acid of the plurality of insertional nucleic acids occurs at an average frequency of about 700 base pairs within the target nucleic acid. In some cases, an insertional nucleic acid of the plurality of insertional nucleic acids occurs at an average frequency of about 800 base pairs within the target nucleic acid. In some cases, an insertional nucleic acid of the plurality of insertional nucleic acids occurs at an average frequency of about 900 base pairs within the target nucleic acid. In some cases, an insertional nucleic acid of the plurality of insertional nucleic acids occurs at an average frequency of about 1000 base pairs within the target nucleic acid. In some cases, an insertional nucleic acid of the plurality of insertional nucleic acids occurs at an average frequency of about 1100 base pairs within the target nucleic acid. In some cases, an insertional nucleic acid of the plurality of insertional nucleic acids occurs at an average frequency of about 1200 base pairs within the target nucleic acid. In some cases, an insertional nucleic acid of the plurality of insertional nucleic acids occurs at an average frequency of about 1300 base pairs within the target nucleic acid. In some cases, an insertional nucleic acid of the plurality of insertional nucleic acids occurs at an average frequency of about 1400 base pairs within the target nucleic acid. In some cases, an insertional nucleic acid of the plurality of insertional nucleic acids occurs at an average frequency of about 1500 base pairs within the target nucleic acid. In some cases, an insertional nucleic acid of the plurality of insertional nucleic acids occurs at an average frequency of about 1600 base pairs within the target nucleic acid. In some cases, an insertional nucleic acid of the plurality of insertional nucleic acids occurs at an average frequency of about 1700 base pairs within the target nucleic acid. In some cases, an insertional nucleic acid of the plurality of insertional nucleic acids occurs at an average frequency of about 1800 base pairs within the target nucleic acid. In some cases, an insertional nucleic acid of the plurality of insertional nucleic acids occurs at an average frequency of about 1900 base pairs within the target nucleic acid. In some cases, an insertional nucleic acid of the plurality of insertional nucleic acids occurs at an average frequency of about 200 base pairs within the target nucleic acid. In some cases, an insertional nucleic acid of the plurality of insertional nucleic acids occurs at an average frequency of less than about 500 base pairs within the target nucleic acid. In some cases, an insertional nucleic acid of the plurality of insertional nucleic acids occurs at an average frequency of more than about 2000 base pairs within the target nucleic acid.

Presented conceptually, an insertion sequence is inserted at a first locus within a first nucleic acid sample molecule and at a second locus within a first nucleic acid molecule. Insertion sequence is often but not necessarily distributed evenly throughout a nucleic acid sample sequence, such that inserts are found, on average, about once every 500 bp-2 kb. Alternately, insertion sequence is inserted in a non-uniform pattern, such that local clusters of insertion sequence are found with a local abundance of, for example, an insertion every 500 bp-2 kb, separated by regions of greater than 2 kb that lack any insertion events. Insertion events are occasionally observed to be locally more dense that one event every 500 bp.

Often, the target nucleic acid comprises DNA. Nonexclusive examples of target DNA or sample DNA includes the following: genomic DNA; an exon; an intron; complementary DNA (cDNA); prokaryotic DNA; eukaryotic DNA; bacterial DNA; bacterial genomic DNA; bacterial DNA from multiple bacterial species. Some target DNA does not comprise plant DNA, or does not consist of plant DNA. Some DNA comprises animal DNA, such as mammalian DNA, or more narrowly human DNA. Some, target nucleic acid comprises RNA, such as messenger RNA (mRNA).

B. Transposase Mediated Oligonucleotides

Further disclosed herein are oligonucleotides comprising an adapter sequence and two mosaic ends, wherein the mosaic ends are recognized by a transposase. Some oligonucleotides, from 5' to 3', comprises a first mosaic end, a first primer binding site, a second primer binding site and a second mosaic end. Some adapter sequence comprises a first primer binding site and a second primer binding site, wherein the first primer binding site and a second primer binding site are adjacent, and the two mosaic ends flank the adapter sequence.

The first primer binding site is optionally an inverted sequence of the second primer binding site. Some first primer binding sites and second primer binding sites comprise a palindromic sequence. Alternately, the first primer binding site and the second primer binding site may comprise a different sequence.

C. Linearly Amplified Nucleic Acid Libraries

Disclosed herein are libraries comprising populations of nucleic acids comprising at least one promoter sequence, for example a T7, T3, or SP6 promoter sequence, a border sequence, and a target nucleic acid sequence. Some libraries comprise at least 90% of the target nucleic acid sequence derived from a sample. Nucleic acids in the library are derived directly from the target nucleic acid and no member of the library is derived from an early-round amplification of another nucleic acid of the library rather than the original sample. Nucleic acid in the library may have a variation in sequence that differs from the target nucleic acid sequence but each variation in sequence that differs from the target nucleic acid sequence is independently derived. As a consequence, errors in library generation, even if not uncommon, are distinct from one another and are easily distinguished from variation in the underlying sample, which will occur in multiple members of the amplified library. Even in the case where there is some late-stage library processing that involves copying of intermediates, the frequency of a variant in the library remains indicative of whether the variant arose from a mutation or from the underlying sample.

Libraries comprise RNA molecules, or may comprise DNA molecules resultant from reverse transcription of RNA intermediaries. Some libraries comprise populations of RNA molecules, wherein the RNA molecules comprise a 5' end having transposon border sequence such as ME sequence, followed by sample sequence of from 1 kb to 30 kb or greater. In some cases the 3' end spans at least one adjacent insert. RNA libraries are synthesized directly from the sample template, such that mutations differing from the sample nucleic acid molecule occur at a frequency of less than 10%, 9%, 8%, 7%, 6%, 5%, 4%, 3%, 2%, 1%, or less than 1% in an RNA library.

In cases where libraries comprise DNA molecules resultant from reverse-transcription of RNA intermediaries, such as when library constructs are made from the combined T7 transcription and barcoded reverse transcription in the library preparation, subsequent amplification using methods such as PCR are often applied to increase the yield of material in the library. This depicted, for example, in FIG. 8C. PCR produces clonal library molecules and a polymerase error may be copied during amplification. However, because these clonal library molecules are barcoded, identical in length and sequence content, they are easily identified and properly handled in downstream analysis. That is, a library sub-population that possesses a common mutation, but that all share the same barcode and size is likely to be a late clonal amplification of a single, perhaps erroneous, RNA intermediate. In contrast, if a library sub-population possesses a common mutation but otherwise differs in barcode, insert length, insert start and endpoints, or in mutations at other positions, the sub-population is more likely to represent distinct, independently derived intermediates and to be reflective of sequence in the original sample.

Moreover, this clonal amplification occurs late in the DNA library preparation, and is overlaid upon a diverse, nonclonal, uniformly amplified RNA intermediate library, such that such that clonal duplicates are easily identified.

Libraries comprise 50%, 55%, 60%, 65%, 70%, 75%, 80%, 85%, 90%, 91%, 92%, 93%, 94%, 95%, 96%, 97%, 98%, 99%, 99.5%, 99.9% or 100% of the sequence information of a nucleic acid sample such as a genomic sample. Some target nucleic acid comprises a genome of a cell, such as a genome of a cell from a subject. Some genomic samples comprise at least 100,000 kb, 500,000 kb, 1 Mb., 1.5 Mb, 2 Mb, 5 Mb, 10 Mb, 20 Mb, 50 Mb, 100 Mb, 200 Mb, 500 Mb, 1,000 Mb or greater. Some libraries provided herein amplify at least 90% of the genome of a human cell.

Libraries comprising amplification of up to the percentages contemplated herein are accomplished at high levels of amplification, such that a sample as small as a sub genomic sample from a single cell or a bulk sample from a large number of cells is amplified may-fold in library generation, such as 10×, 20×, 50×, 100×, 200×, 500×, 1000×, 2000×, 5000×, 10000×, 20000×, 50000×, 100000×, 200000×, 500000×, 1,000,000×, 2,000,000×, 5,000,000× or greater than 5,000,000×. Some libraries comprise amplification of a sample of at least 1000×.

Libraries generated as herein result in strikingly unbiased, uniform amplification of the sample, such that amplification is not skewed toward on or another region of a sample. Often, 50%, 55%, 60%, 65%, 70%, 75%, 80%, 85%, 90%, 91%, 92%, 93%, 94%, 95%, 96%, 97%, 98%, 99%, 99.5%, 99.9% greater of the amplified library is amplified such that library members are present at a level of at least ¼× and no more than 4× the mean or median library constituent level.

That is, libraries herein represent a sample such that at least 90% of the sample is amplified at least 1000×, and such that the library is uniform to the point that 85% of the amplified sample is present at within 1/× to 4× the mean or median level of the amplified sample.

III. Kits

Further disclosed herein are kits comprising: an insertional nucleic acid, wherein the oligonucleotide comprises a mosaic end that is recognized by a transposase; and a transposase. Some insertional nucleic acid further comprises an adapter sequence. The adapter sequence is flanked by an insertion-compatible sequence, such as a first mosaic end and a second mosaic end. Some adapter sequence comprises a primer annealing sequence. Some kits further comprise a PCR primer that anneals to the primer annealing sequence. Some PCR primers comprise a tag. Often, a first PCR primer comprises a first tag and a second PCR primer comprises a second tag, wherein the first tag and the second tag are different. Some kits further comprises a plurality of containers. The plurality of containers may comprises a microwell plate. One or more containers of the plurality of containers may contain a mixture comprising one or more of the transposase, a portion of the plurality of insertional nucleic acids and the first/second PCR primers. The transposase is often a Tn5 transposase, though alternatives are contemplated. some kits further comprises a polymerase. The polymerase is often a phi DNA polymerase, though alternatives are contemplated. The first/second PCR primers, if included, are random primers. Alternately or in combination, the adapter sequence comprises a transcriptional promoter. The transcriptional promoter is often a T7 RNA polymerase promoter, though alternatives are contemplated. Often, one or more containers of the plurality of containers contains a mixture comprising one or more of the transposase, a portion of the plurality of insertional nucleic acids and a T7 RNA polymerase.

Figure 2:
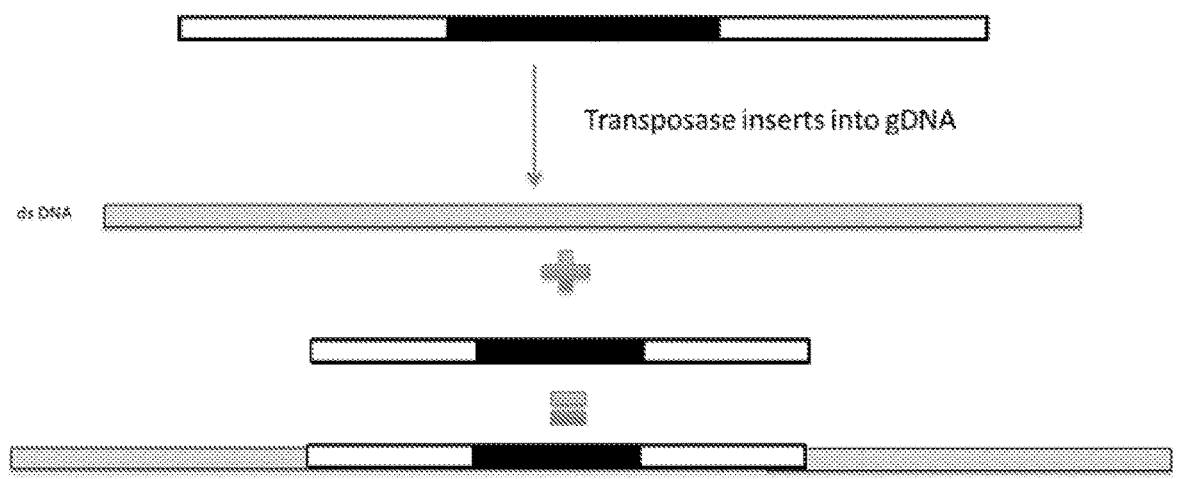
FIG. 2 depicts exemplary transposase mediated insertion of a contiguous insertional nucleic acid into target DNA.
Figure 3:
FIG. 3 depicts an exemplary multi-insert nucleic acid.

Turning to the figures for additional delineation of the disclosure herein, one sees the following. At FIG. 1 one sees an exemplary insertion schematic. The insertion comprises an ME repeat, an RNA promoter and a second ME repeat. Repeats other than ME repeats compatible with a transposase, invertase or recombinase or other enzyme as contemplated herein is also consistent with the disclosure herein. A number of RNA promoters are consistent with the disclosure herein, including T7, T3, SP6 but also including a number of eukaryotic, eubacterial, archaeal, and viral promoters as disclosed herein. At FIG. 2 one sees a schematic indicating insertion of an insert sequence into a sample, in this case a genomic DNA sample. FIG. 3 depicts a sample having a plurality of inserts randomly distributed throughout the sample. In preferred embodiments, insertions are found at a frequency of no more than one insert per 500 bases, exemplarily one insert every 500 bp to 2 kb, 3 kb, 4 kb or 5 kb. Alternate insert densities are consistent with the disclosure herein.

Figure 4:
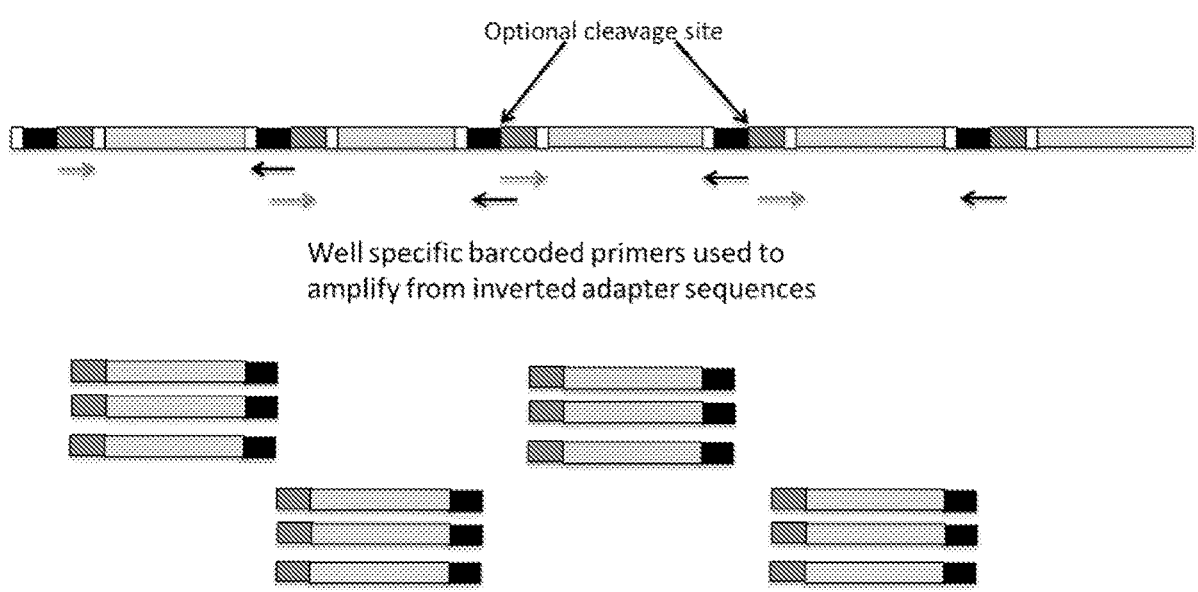
FIG. 4 depicts an alternate approach to library synthesis relying upon digestion and primer amplification rather than RNA directed intermediate synthesis.
Figure 5:
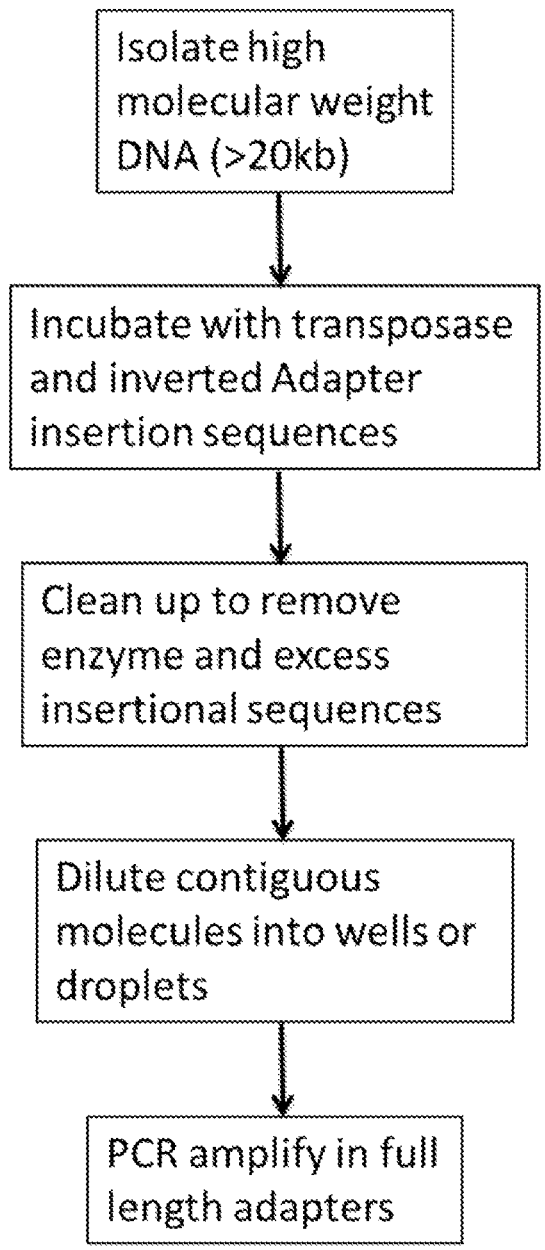
FIG. 5 depicts an exemplary flow diagram for the approach of FIG. 4.

At FIG. 4 one sees an alternate embodiment having insertion fragments comprising an inverted repeat, separated by a cleavage site. Inverted repeats are optionally inverted promoter repeats, or alternately primer binding sites. FIG. 5 presents a workflow for this alternate library generation approach.

Figure 6:
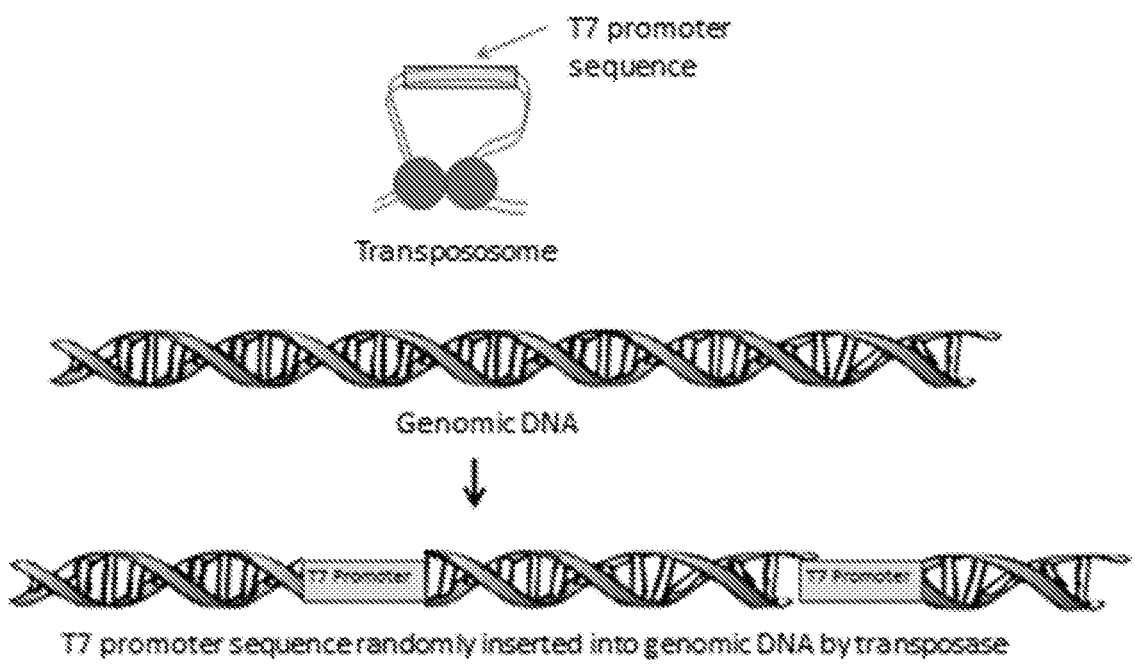
FIG. 6 depicts a transposase 'transpososome' comprising a transposase activity and an insert sequence comprising a T7 promoter sequence adjacent to a genomic target DNA, and following insertion, a genomic DNA molecule having insertion sequence comprising T7 promoter sequence introduced therein.
Figure 7:
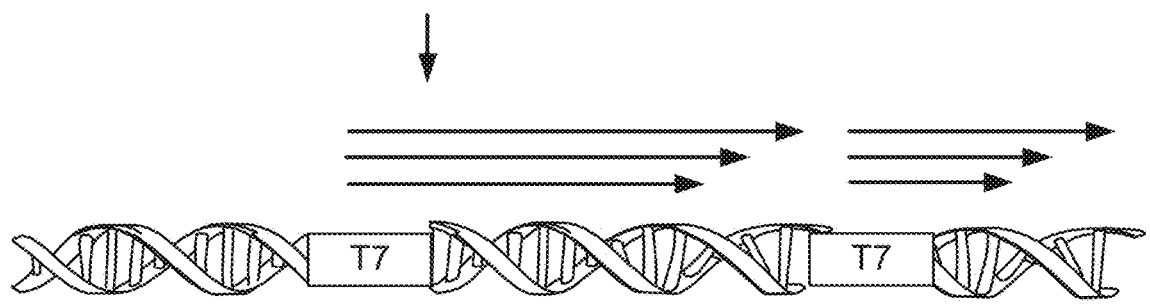
FIG. 7 depicts RNA molecules being transcribed from a T7 promoter to selectively amplify nucleic acid information adjacent to transposase insertion sites. Not shown is concurrent reverse transcription of the RNA molecules into DNA.

At FIG. 6 one sees a schematic depicting the use of a transposase to introduce an insert fragment comprising a T7 RNA polymerase promoter at random positions into a nucleic acid sample, in this case a genomic DNA sample. FIG. 7 depicts RNA transcripts being generated from T7 inserted promoters. Linear amplification occurs from the successive synthesis of multiple RNA transcripts from a single promoter. In this figure, the successively synthesized RNA products are superimposed on top of another from a common 5' end. The 3' end of these transcripts varies among the transcription reactions, and is preferably from 2 kb to 30 kb. The figure is not drawn to scale. Often, an RNA molecule synthesized from a first inserted promoter spans a second insertion site, facilitating identification of the second insertion site upon sequencing of the molecule spanning the second insertion, or sequencing of a reverse-transcribed library product resultant therefrom. It is also seen that the RNA molecules are synthesized directly from the genomic sample template rather than being templated by intermediate synthesis products. As a consequence, any errors in synthesis are individually rare, and easily recognized as errors in analysis of an aggregate sample. For example, an error in synthesis of the sequence between the two depicted T7 promoter sites is very unlikely to independently occur in the four RNA molecules depicted as partially or completely spanning the region. As a result, any error in one sequence is compared against the other three (and, in practice, against up to 1000× or more synthesized RNA intermediate molecules that span the region in question) and easily identified as an artefact of the process.

At FIGS. 8A-8C one sees a schematic presentation of methods presented herein. Genomic DNA is contacted to a population of transposons loaded using insertion fragments comprising RNA promoter sequence such as T7 promoter sequence. The inserts are introduced at a frequency of about one insert per 500 bp to 2 kb of the genomic sample. At FIG. 8B, T7 polymerase is used to synthesize RNA transcripts from the RNA promoters inserted into the sample. It is observed that, at a density of insertion of one per 500 bp to 1 per 2 kb, transcripts of an average length of, for example 2 kb to 30 kb span multiple insertion sites. FIG. 8B also details the generation of a DNA library through the reverse-transcription of RNA library intermediates. At FIG. 8C one sees bead purification and, in this case, barcoded amplification of the synthesized products. Amplification via PCR at this step does not negate the beneficial properties resulting from the RNA intermediates being synthesized directly from the sample template—namely, that errors in RNA synthesis are independently derived and thus likely to be individually rare, and chimeric intermediate synthesis is essentially eliminated.

Figure 9:
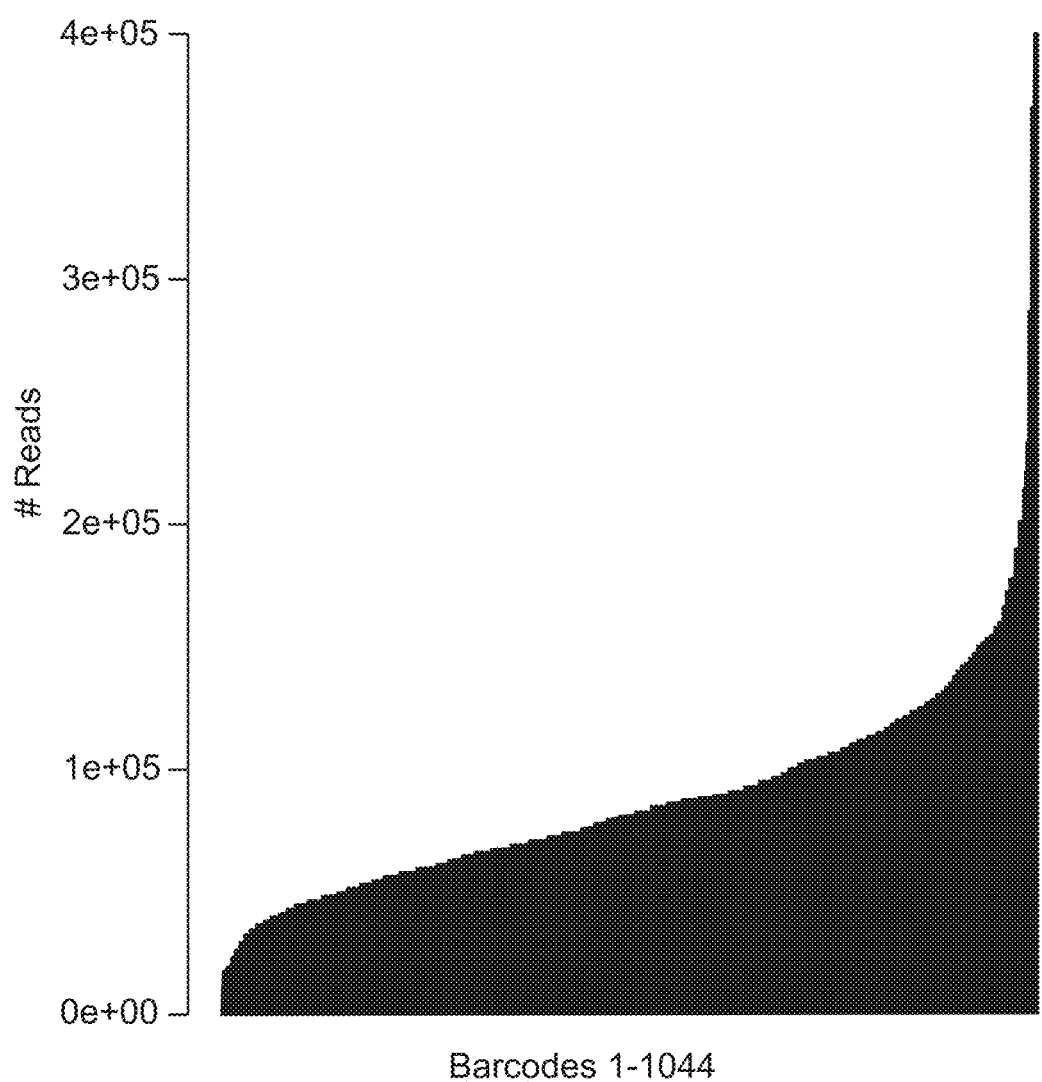
FIG. 9 depicts relative representation of 1044-8 base pair error correcting droplet barcodes sorted on the X-axis by relative abundance. 1.8 M microdroplets containing individual barcode primers were merged with gDNA and amplified. 400 M reads were generated with HiSeq 2500 Rapid mode 2×150 paired end chemistry. More than 96% of reads contained barcodes with 1 or fewer mismatched bases. Uniform representation: >90% of labels represented within a 3-fold range.

At FIG. 9 one sees a distribution of barcoded reads produced from the library intermediates as produced herein. It is observed that the vast majority of the reads occur at an abundance that differs from the median abundance by less than 4×. That is, sample amplification is strikingly uniform, such that loci that are 'hyper-amplified' or fail to be amplified are particularly rare relative to regions of the sample that are uniformly amplified.

FIG. 10 depicts a library processing workflow that generates overlapping sequences from RNA intermediates generated directly from genomic sample sequence. The RNA library is in vitro transcribed and reverse transcription is performed to generate a DNA library. Library constituents are sequenced and overlapping sequences are assembled into contigs. Insertion sites are readily identified in sequence reads, and are used to anchor reads that fall to otherwise repetitive sequence regions.

At FIG. 11 one sees final processing of a sequence data set. Sequence datasets from different insertion-tagging events of a common sample are compared. Sequences are aligned, and treatment-specific insertion sites are identified as being unique to a given sample/insertion treatment combination. These insertion sequences are identified and removed from the final sample sequence assembly.

FIG. 12 depicts the effect of random insertion events on an otherwise repetitive genomic locus. The region comprises in this figure three successive LTR monomers. Mapping a sequence to one or another of the repeats is difficult using sequencing approaches known to one of skill in the art. However, as seen in the lower panel, random insertion of T7 insertion sequence into the repeat region generates an 'insertion fingerprint' or barcode that differentially tags each LTR, such that sample sequence information in combination with insertion site and sequence information facilitates the accurate assembly of LTR sequence into a plurality of repeats at the locus, and allows LTR sequence that maps elsewhere to be excluded from the assembly of this locus.

Figure 13:
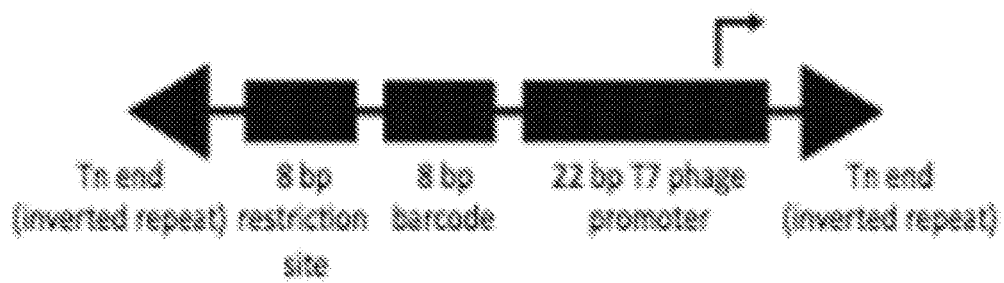
FIG. 13 depicts customized EZ-Tn5 transposon.
Figure 15A:
FIGS. 15A-D depict the application of the methods herein to the sequencing of a repetitive genomic locus.
Figure 15B:
Figure 15C:
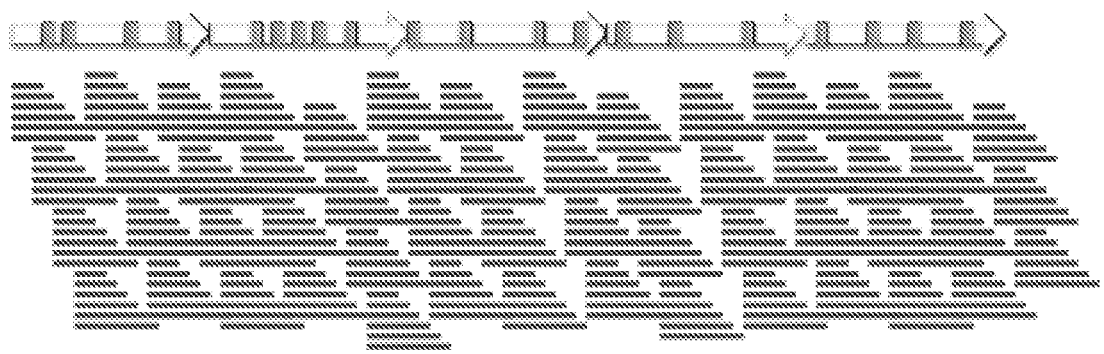
Figure 15D:
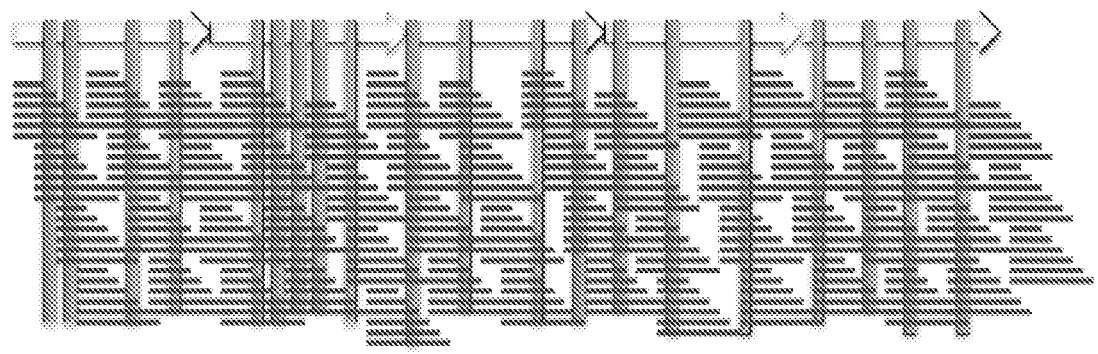

FIG. 13 depicts an alternate insertion fragment. ME ends are included as is a single T7 phage promoter, consistent with the core insertion fragment structure. Additionally included are an 8 bp barcode and an insert-specific restriction site to facilitate downstream analysis and quality control. These additional features are consistent with the disclosure herein but are not included in all embodiments.

FIGS. 14 A-D depict one processing route for RNA intermediates as synthesized herein. RNA transcripts are poly-A tailed, and reverse-transcribed through a process involving incorporation of biotinylated dNTPs. Synthesized DNA products are isolated through binding to streptavidin, and processed further to generate a library of sequence-ready fragments.

FIGS. 15A-D depict a step-by-step view of how a repetitive region is rendered nonrepetitive and through practice of the methods herein. At FIG. 15A one sees a region comprising 5 repeats of a monomer. The repeats are not easily distinguished by sequence, and sequence efforts using approaches known to one of skill in the art often collapse to a single monomer unit having a redundancy of reads mapping thereto. At FIG. 15B, insertion has been performed to generate a random pattern of insertion fragments introduced throughout the repetitive locus (and, not shown, elsewhere throughout the genomic sample). At FIG. 15C one sees the RNA intermediate library products, mapped to the insertion sites from which their synthesis was directed. Synthesis products vary in their overall lengths, and in many cases RNA transcripts span multiple insertion sites downstream of the site from which they are transcribed. Sequences of the intermediates are determined, and mapped to the various repeats of the locus. At FIG. 15D, insertion sequences are identified and used to anchor the alignment of the otherwise repetitive locus sequence. Insertion sequences are then identified and removed, resulting in a correctly sequenced multimeric repeat region. Sequences that bridge the edge of the final repeat are used to place the repeat sequence into its genomic locus in the assembled sequence product.

Figure 16:
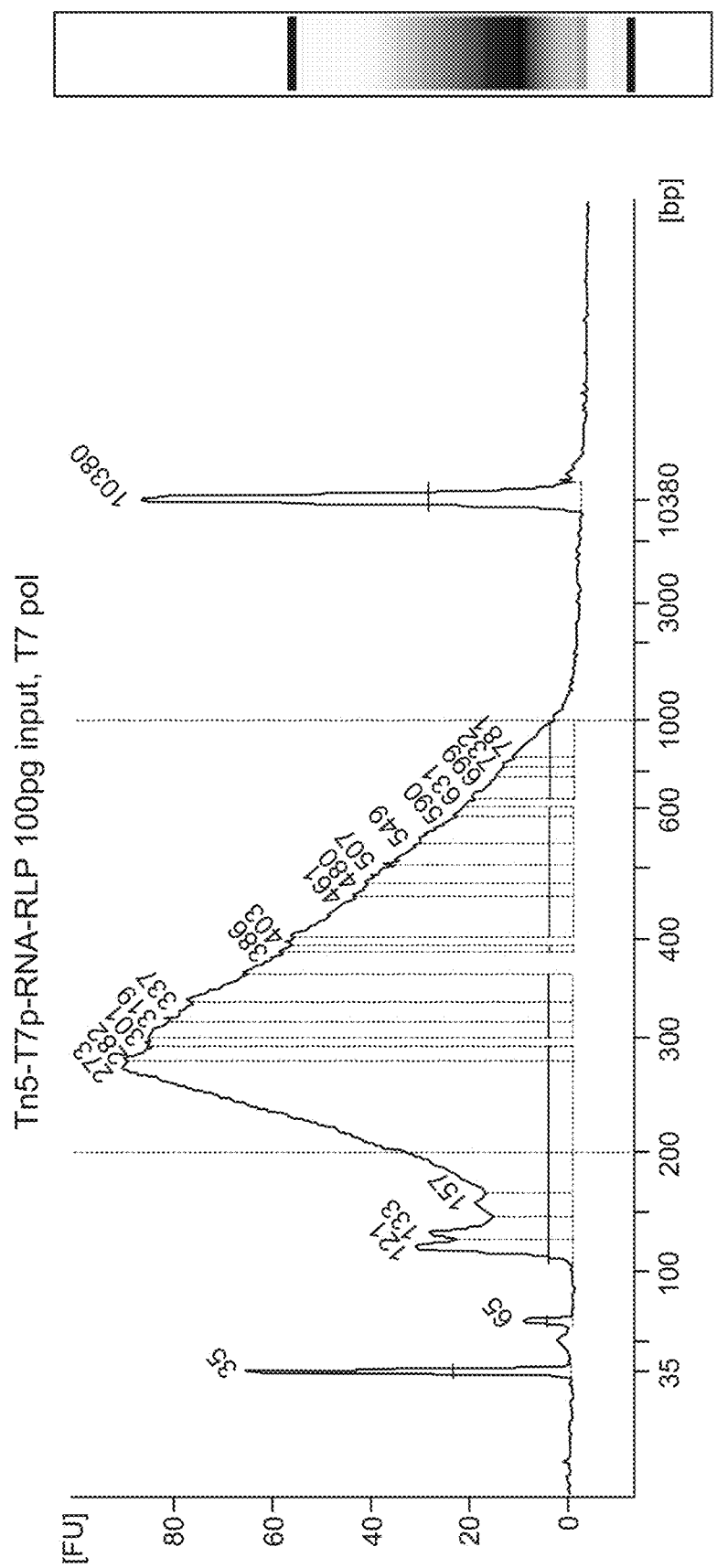
FIG. 16 depicts library length distribution for a sequencing library reverse-transcribed from an RNA intermediate library generated from a T7-inserted sample template.

At FIG. 16, one sees a bioanalyzer trace of a full reaction indicating the distribution of fragment lengths for a sequencing library reverse-transcribed from an RNA intermediate library transcribed from a T7 inserted template. Bands at 35 and at 10380 kb are markers. Library constituent lengths span from 121 bp to well over 1 kb, with a peak about 272 bp.

Figure 17:
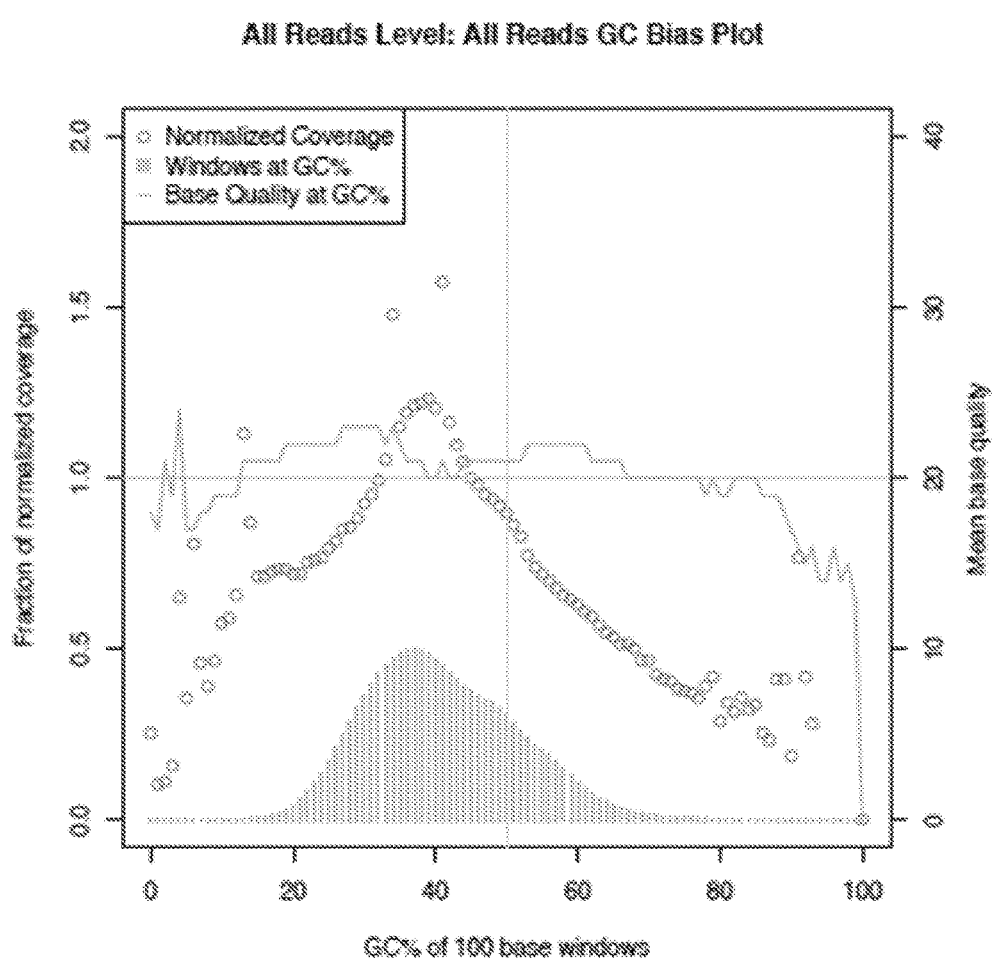
FIG. 17 shows that GC percentage for a sequencing library reverse-transcribed from an RNA intermediate library generated from a T7-inserted sample template matches that of the template human genome.

At FIG. 17, one sees a plot of GC percentage for a sequencing library reverse-transcribed from a synthesized RNA intermediate library. The library demonstrates that most commonly observed 100-base windows exhibit a 40% GC, a distribution that is expected if there is no GC amplification bias in the library relative to the underlying human genome. The figure indicates that the library is unbiased by underlying sample GC percentage, unlike many alternative library generation approaches.

The disclosure herein is further clarified in reference to a partial list of numbered embodiments as presented below.

1. A method of sequencing a nucleic acid sample having a sequence comprising an element repeated at a first region and a second region, comprising
inserting a nucleic acid tag having a nucleic acid tag sequence into the first region at a first repeat site generating a first sequence read comprising element sequence and nucleic acid tag sequence at the first repeat site, and a second sequence read comprising element sequence spanning the first repeat site from the nucleic acid sample, and
assigning the first sequence read comprising repetitive element sequence and nucleic acid tag sequence at a first repeat site to the first region.

2. The method of embodiment 1, wherein the repeat site comprises a position within a repetitive element.

3. The method of embodiment 1, wherein the region comprises a locus of a genome that harbors a repeat site.

4. The method of embodiment 1, comprising assigning the second sequence read comprising repetitive element sequence spanning the repeat site to the second region.

5. The method of embodiment 1, wherein the nucleic acid tag comprises RNA promoter sequence.

6. The method of embodiment 5, wherein the RNA promoter sequence comprises at least one of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

7. The method of embodiment 5, wherein the RNA promoter sequence comprises T7 sequence.

8. The method of embodiment 1, comprising inserting a nucleic acid tag having a nucleic acid tag sequence into a second site in the element at a second region.

9. The method of embodiment 8, comprising assigning a third sequence read comprising repetitive element sequence and comprising nucleic acid tag sequence at the second site to the second region.

10. The method embodiment 1, comprising inserting at least two nucleic acid tags having nucleic acid tag sequences into at least two sites in the element at two or more regions at an average density of no more than 1 insertion per 500 basepairs.

11. A method of converting a multimeric repeat nucleic acid region that is not uniquely sequenceable into a unique region, comprising a) treating the isolated nucleic acid sample comprising a repeated nucleic acid region that is not uniquely sequenceable a using a random insertional mutagen to insert a tag into one copy of said repeated nucleic acid region, thereby rendering said one copy of said repeated nucleic acid region unique, b) obtaining sequence reads from the insertionally mutagenized isolated nucleic acid sample, and c) assigning sequence reads having a repeated nucleic acid region sequence and a tag sequence to a unique repeated nucleic acid region.

12. The method of embodiment 11, comprising inserting two or more nucleic acid tags having nucleic acid tag sequences into two or more sites in the element at two or more regions at an average density of no more than 1 insertion per 500 basepairs.

13. The method of embodiment 11, wherein the tag comprises an RNA promoter.

14. The method of embodiment 12, wherein the promoter is at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

15. The method of embodiment 12, wherein the promoter comprises at least one of T7, T3 and SP6.

16. The method of embodiment 12, wherein the promoter comprises T7.

17. The method of embodiment 12, comprising contacting said insertionally mutagenized isolated nucleic acid sample to an RNA polymerase.

18. The method of embodiment 17, comprising generating a population of RNA molecules comprising tag sequence and repeated nucleic acid region sequence.

19. The method of embodiment 18, wherein the sequence reads are obtained from the population of RNA molecules.

20. The method of embodiment 19, wherein the population of RNA molecules is reverse transcribed to generate DNA molecules.

21. The method of embodiment 11, wherein the random insertional mutagen comprises a transposase.

22. The method of embodiment 21, wherein the transposase is at least one transposase selected from the list consisting of Tn5 transposase, sleeping beauty transposase, piggybac transposase, and Mariner transposase.

23. The method of embodiment 22, wherein the transposase is Tn5.

24. An isolated nucleic acid sample treated with an insertional mutagen such that a first repeat element is interrupted by a tag at a first position and a second copy of said repeat element is interrupted by said tag at a second position, such that sequence reads comprising tag sequence and repeat element sequence indicative of said tag at said first position uniquely map to said first repeat element.

25. The sample of embodiment 24, comprising two or more nucleic acid tags having nucleic acid tag sequences at two or more sites in the repeat element at two or more regions at an average density of no more than 1 insertion per 500 basepairs.

26. The sample of embodiment 24, wherein said tag comprises a promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

27. The sample of embodiment 24, wherein said tag comprises a promoter selected from the list consisting of a T7, T3, and SP6.

28. The sample of embodiment 24, wherein said tag comprises a T7 promoter.

29. The sample of embodiment 24, wherein said insertional mutagen comprises a transposase selected from the list consisting of Tn5 transposase, sleeping beauty transposase, piggybac transposase, and Mariner transposase.

30. The sample of embodiment 24, wherein said insertional mutagen comprises an integrase.

31. The sample of embodiment 24, wherein said repeat element is selected from the group consisting of a transposon, a retrotransposon, a DNA transposon, an insertion sequence, a plasmid, a bacteriophage, a group II intron, a group I intron, an Alu element, a MIR element, an intracisternal A particle (IAP), an ETn, a virus, a transposable element, a LINE, and a SINE.

32. An RNA library generated by contacting the sample of claim 25 to an RNA polymerase.

33. A DNA library generated by contacting the RNA library of embodiment 32 to a reverse-transcriptase.

34. A genomic nucleic acid sample sequencing library comprising a plurality of RNA molecules transcribed from an RNA promoter, said plurality of RNA molecules each comprising a first end comprising repetitive insert sequence and a second end comprising genomic nucleic acid sample sequence, wherein at least 90% of said genomic nucleic acid sample is represented in said plurality of RNA molecules.

35. The library of embodiment 34, wherein the plurality of RNA molecules is generated directly from the genomic nucleic acid sample.

36. The library of embodiment 34, wherein at least 95% of said genomic nucleic acid sample is represented in said plurality of RNA molecules.

37. The library of embodiment 34, wherein at least 99% of said genomic nucleic acid sample is represented in said plurality of RNA molecules.

38. The library of embodiment 34, wherein said sample is amplified at least 100× relative to said genomic sample.

39. The library of embodiment 34, wherein said sample is amplified at least 1000× relative to said genomic sample.

40. The library of embodiment 38, wherein at least 85% of said amplified sample is present at a level that is no more than 4× of a mean amplification level.

41. The library of embodiment 39, wherein at least 85% of said amplified sample is present at a level that is no more than 4× of a mean amplification level.

42. The library of embodiment 34, wherein said RNA promoter sequence comprises at least an identifiable portion promoter is at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

43. The library of embodiment 34, wherein said RNA promoter sequence comprises at least one of T7, T3 and SP6.

44. The library of embodiment 34, wherein said RNA promoter sequence comprises T7 promoter sequence.

45. The library of embodiment 34, wherein said genomic nucleic acid sample is treated to insert a nucleic acid encoding said RNA promoter sequence into said genomic nucleic acid sample.

46. The library of embodiment 45, wherein said genomic nucleic acid sample is contacted to an integrase.

47. The library of embodiment 45, wherein said genomic nucleic acid sample is contacted to a transposase.

48. The library of embodiment 47, wherein the transposase is selected from the list consisting of Tn5 transposase, sleeping beauty transposase, piggybac transposase, and Mariner transposase.

49. The library of embodiment 48, wherein said transposase is Tn5.

50. A DNA library comprising the RNA library of embodiment 34, contacted to a reverse-transcriptase.

51. A genomic nucleic acid sample sequencing library comprising a plurality of RNA molecules, wherein the RNA molecules are transcribed directly from the genomic nucleic acid sample, such that no RNA molecule serves as a template for a second RNA molecule.

52. The genomic nucleic acid sample sequencing library of embodiment 51, wherein at least 90% of said genomic nucleic acid sample is represented in said library.

53. The genomic nucleic acid sample sequencing library of embodiment 51, wherein at least 95% of said genomic nucleic acid sample is represented in said library.

54. The genomic nucleic acid sample sequencing library of embodiment 51, wherein at least 99% of said genomic nucleic acid sample is represented in said library.

55. The genomic nucleic acid sample sequencing library of embodiment 51, wherein said sample is amplified at least 100× relative to said genomic sample.

56. The genomic nucleic acid sample sequencing library of embodiment 51, wherein said sample is amplified at least 1000× relative to said genomic sample.

57. The genomic nucleic acid sample sequencing library of embodiment 55, wherein at least 85% of said amplified sample is present at a level that is no more than 4× of a mean amplification level.

58. The genomic nucleic acid sample sequencing library of embodiment 55, wherein at least 85% of said amplified sample is present at a level that is no more than 4× of a mean amplification level.

59. The genomic nucleic acid sample sequencing library of embodiment 51, comprising at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

60. The genomic nucleic acid sample sequencing library of embodiment 51, wherein said RNA promoter sequence comprises at least one of T7, T3 and SP6.

61. The genomic nucleic acid sample sequencing library of embodiment 51, wherein said RNA promoter sequence comprises T7 promoter sequence.

62. A nucleic acid sample comprising an isolated genomic nucleic acid sample into which a exogenous promoter is inserted at an average density of at least 1 insertion per 5 kb.

63. The nucleic acid sample of embodiment 62, wherein the exogenous promoter is inserted at an average density of no more than 1 insertion per 500 basepairs.

64. The nucleic acid sample of embodiment 62, wherein the nucleic acid sample is contacted to an RNA polymerase.

65. The nucleic acid sample of embodiment 64, comprising a plurality of RNA molecules comprising exogenous promoter sequence and isolated genomic nucleic acid sample sequence.

66. The nucleic acid sample of embodiment 65, wherein 90% of the isolated genomic nucleic acid sample sequence is represented by said plurality of RNA molecules.

67. The nucleic acid sample of embodiment 65, wherein 95% of the isolated genomic nucleic acid sample sequence is represented by said plurality of RNA molecules.

68. The nucleic acid sample of embodiment 65, wherein 99% of the isolated genomic nucleic acid sample sequence is represented by said plurality of RNA molecules.

69. The nucleic acid sample of embodiment 65, wherein said sample is amplified at least 100× relative to said genomic sample.

70. The nucleic acid sample of embodiment 65, wherein said sample is amplified at least 1000× relative to said genomic sample.

71. The nucleic acid sample of embodiment 65, wherein at least 85% of said amplified sample is present at a level that is no more than 4× of a mean amplification level.

72. The nucleic acid sample of embodiment 65, wherein at least 85% of said amplified sample is present at a level that is no more than 4× of a mean amplification level.

73. A nucleic acid sample comprising a plurality of repetitive elements having a length of at least 300 to 500 base pairs, wherein at least 90% of said plurality of repetitive elements are independently interrupted by at least one species of randomly inserted tag.

74. The nucleic acid sample of embodiment 73, wherein the plurality of repetitive elements have a length of at least 6000 base pairs.

75. The nucleic acid sample of embodiment 73, wherein the at least one species of randomly inserted tag comprises a nucleic acid encoding a promoter sequence.

76. The nucleic acid sample of embodiment 74, comprising at least one promoter selected from the list consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

77. The nucleic acid sample of embodiment 74, comprising RNA promoter sequence that comprises at least one of T7, T3 and SP6.

78. The nucleic acid sample of embodiment 74, comprising RNA promoter sequence that comprises T7 promoter sequence.

79. The nucleic acid sample of embodiment 74, wherein said sample is contact to an RNA polymerase.

80. The nucleic acid sample of embodiment 79, wherein RNA molecules representing at least 90% of said nucleic acid sample are generated.

81. The nucleic acid sample of embodiment 79, wherein RNA molecules representing at least 95% of said nucleic acid sample are generated.

82. The nucleic acid sample of embodiment 79, wherein RNA molecules representing at least 99% of said nucleic acid sample are generated.

83. The nucleic acid sample of embodiment 79, wherein said sample is subsequently contacted to a DNase.

84. A method of generating a modified nucleic acid, the method comprising: combining
a. an insertional nucleic acid comprising an adapter sequence that is flanked by nucleic acid integrase recognition sequences;
b. a target nucleic acid molecule; and
c. a nucleic acid integrase,
wherein the nucleic acid integrase covalently inserts the insertional nucleic acid into the target nucleic acid at a first location and at a second location within the target nucleic acid molecule, said first location and said second location being separated by at least 200 bp.

85. The method of embodiment 84, wherein aid first location and said second location are separated by at least 500 bp.
86. The method of embodiment 84, wherein aid first location and said second location are separated by at least 7500 bp.
87. The method of embodiment 84, wherein aid first location and said second location are separated by at least 1.0 kb.
88. The method of embodiment 84, wherein aid first location and said second location are separated by at least 1.5 kb.
89. The method of embodiment 84, wherein aid first location and said second location are separated by at least 2.0 kb.
90. The method of embodiment 84, wherein aid first location and said second location are separated by at most 2.5 kb.
91. The method of embodiment 84, wherein aid first location and said second location are separated by at most 2.0 kb.
92. The method of embodiment 84, wherein aid first location and said second location are separated by at most 1.5 kb.
93. The method of embodiment 84, wherein aid first location and said second location are separated by at most 1 kb.
94. A method of generating a plurality of multi-insert nucleic acids, the method comprising: combining
a. an insertional nucleic acid comprising an adapter sequence that is flanked by nucleic acid integrase recognition sequences;
b. a plurality of target nucleic acids; and
c. a nucleic acid integrase,
wherein the nucleic acid integrase
i. cleaves one or more of the plurality of target nucleic acids to produce one or more recombination sites,
ii. recognizes the nucleic acid integrase recognition sequences; and
iii. inserts the insertional nucleic acid into the one or more recombination sites to generate the plurality of multi-insert nucleic acids.
95. The method of embodiment 94, wherein the adapter sequence comprises an RNA promoter sequence.
96. The method of embodiment 94, wherein the adapter sequence comprises at least one of T7, T3 and SP6 RNA promoter sequence.
97. The method of embodiment 94, wherein the adapter sequence comprises T7 RNA promoter sequence.
98. The method of embodiment 94, further comprising adding a PCR primer to the plurality multi-insert nucleic acids, wherein the PCR primer anneals to the insertional nucleic acid or a portion thereof, and amplifying one or more of the plurality of multi-insert nucleic acids or a portion thereof.
99. The method of embodiment 94, wherein the PCR primer anneals to the adapter sequence or portion thereof.
100. The method of embodiment 94, further comprising diluting the plurality of multi-insert nucleic acids into a plurality of containers, to produce a first plurality of diluted multi-insert nucleic acids in a first container and a second plurality of diluted multi-insert nucleic acids in a second container.
101. The method of embodiment 100, wherein diluting the plurality of multi-insert nucleic acids into a plurality of containers dilutes the plurality of multi-insert nucleic acids such that a single multi-insert nucleic acid is present in each container of the plurality of containers.
102. The method of any one of embodiments 100 or 101, wherein the plurality of multi-insert nucleic acids comprises genomic DNA, and wherein diluting the plurality of multi-insert nucleic acids into a plurality of containers dilutes the genomic DNA such that a haplotype frequency in a container is very low.
103. The method of embodiment 100, wherein the plurality of containers comprises a container selected from a tube, a microwell and a droplet.
104. The method of any one of embodiments 100-103, further comprising
a. providing a first PCR primer comprising a first tag to the first container, wherein at least a portion of the first PCR primer anneals the insertional nucleic acid or portion thereof;
b. providing a second PCR primer comprising a second tag to the second container, wherein at least a portion of the second PCR primer anneals to the insertional nucleic acid or portion thereof, and wherein the second tag is different than the first tag;
c. providing a nucleic acid polymerase into the first container and the second container;
d. amplifying the first plurality of diluted multi-insert nucleic acids or portions thereof, thereby producing a first plurality of tagged nucleic acids; and
e. amplifying the second plurality of diluted multi-insert nucleic acids or portions thereby producing a second plurality of tagged nucleic acids.
105. The method of embodiment 104, wherein the first tag comprises a first tag nucleic acid sequence and the second tag comprises a second tag nucleic acid sequence, wherein the first tag nucleic acid sequence and the second tag nucleic acid sequence are different.
106. The method of embodiment 104 or 105, wherein the nucleic acid polymerase is a phi29 DNA polymerase and the insertional nucleic acid comprises random primer annealing sites.
107. The method of embodiment 104 or 105, wherein the nucleic acid polymerase is T7 polymerase and the insertional nucleic acid comprises a T7 primer annealing site.
108. The method of embodiment 107, further comprising introducing a reverse transcriptase and random primers.
109. The method of any one of embodiments 104-108, further comprising cleaving the insertional nucleic acid of the plurality of multi-insert nucleic acids to produce a plurality of multi-insert nucleic acid fragments, wherein each multi-insert nucleic acid fragment is flanked by the first portion of the insertional nucleic acid and the second portion of the insertional nucleic acid.
110. The method of embodiment 109, wherein the cleaving occurs before adding the first and/or second PCR primer and the amplifying.
111. The method of any one of embodiments 104-110, further comprising pooling the first plurality of tagged nucleic acids and the second plurality of tagged nucleic acids.
112. The method of any one of embodiments 104-111, further comprising adding an affinity molecule to the first plurality of tagged nucleic acids and/or the second plurality of tagged nucleic acids.
113. The method of embodiment 112, wherein the affinity molecule is biotin.
114. The method of embodiment 112 or 113, further comprising capturing the first plurality of tagged nucleic acids and/or the second plurality of tagged nucleic acids via the affinity molecule.
115. The method of any one of embodiments 104-113, further comprising sequencing the first plurality of tagged nucleic acids and the second plurality of tagged nucleic acids.
116. The method of any one of embodiments 104-114, wherein the first portion of the insertional nucleic acid comprises a first portion of the adapter sequence and the second portion of the insertional nucleic acid comprises a second portion of the adapter sequence.

117. The method of embodiment 115, wherein the first portion of the adapter sequence and the second portion of the adapter sequence comprise a different sequence.

118. The method of embodiment 115, wherein the first portion of the adapter sequence is the same as the second portion of the adapter sequence.

119. The method of embodiment 115, wherein the first portion of the adapter sequence and the second portion of the adapter sequence are adjacent prior to combining the insertional nucleic acid, plurality of target nucleic acids and integrase.

120. The method of embodiment 118, wherein the first portion of the adapter sequence is an inverted sequence of the second portion of the adapter sequence.

121. The method of embodiment 118, wherein the first portion of the adapter sequence and the second portion of the adapter sequence form a palindromic sequence.

122. The method of any one of embodiments 94-120, wherein the nucleic acid integrase is a transposase.

123. The method of embodiment 122, wherein the transposase is a Tn5 transposase.

124. The method of embodiments 121 or 122, wherein the nucleic acid integrase recognition sequences are mosaic ends.

125. The method of any one of embodiments 94-124 wherein the ratio of transposase to insertional nucleic acid is set such that insertional nucleic acids are introduced at an average density of 500 bp to 2 kb over a span of at least 3 insertional nucleic acid insertion sites.

126. A nucleic acid molecule comprising a chromosome-sized target nucleic acid and a plurality of insertional nucleic acids, wherein the plurality of insertional nucleic acids are distributed at a plurality of recombination sites throughout the target nucleic acid at an average density of at least one insert per 10 kb.

127. The nucleic acid molecule of embodiment 126, wherein the insertional nucleic acid comprises a primer annealing sequence.

128. The nucleic acid molecule of embodiment 126, wherein the insertional nucleic acid comprises a first primer annealing sequence and a second primer annealing sequence.

129. The nucleic acid molecule of embodiment 126, wherein the first primer annealing sequence and the second primer annealing sequence are adjacent.

130. The nucleic acid molecule of embodiment 127 or 128, wherein the first primer annealing sequence and the second primer annealing sequence are different.

131. The nucleic acid molecule of embodiment 129, wherein the first primer annealing sequence is an inverted sequence of the second primer annealing sequence.

132. The nucleic acid molecule of embodiment 128 or 129, wherein the first primer annealing sequence and the second primer annealing sequence comprise the same sequence.

133. The nucleic acid molecule of embodiment 132, wherein the first primer annealing sequence and the second primer annealing sequence form a palindrome.

134. The nucleic acid molecule of embodiment 126, wherein the insertional nucleic acid comprises a transcriptional promoter 135. The nucleic acid molecule of embodiment 134, wherein the insertional nucleic acid encodes a promoter selected from the list of promoters consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

136. The nucleic acid molecule of embodiment 134, wherein the insertional nucleic acid encodes a promoter selected from the list of promoters consisting of a T7, T3, and SP6.

137. The nucleic acid molecule of embodiment 134, wherein the insertional nucleic acid encodes a T7 promoter.

138. The nucleic acid molecule of embodiment 134, wherein the transcriptional promoter is recognized by an RNA polymerase.

139. The nucleic acid molecule of any one of embodiments 126-138, wherein the insertional nucleic acid comprises a mosaic end, wherein the mosaic end is recognized by a transposase.

140. The nucleic acid molecule any one of embodiments 126-139, wherein the target nucleic acid comprises a plurality of target nucleic acid fragments separated by one or more of the insertional nucleic acids of the plurality of inserted nucleic acids.

141. The nucleic acid molecule of any one of embodiments 126-140, wherein each insertional nucleic acid of the plurality of insertional nucleic acids occurs at an average frequency of about 500 base pairs to about 2000 base pairs within the target nucleic acid.

142. The nucleic acid molecule of any one of embodiments 126-141, wherein the target nucleic acid comprises DNA.

143. The nucleic acid molecule of embodiment 142, wherein the DNA comprises genomic DNA.

144. The nucleic acid molecule of embodiment 142 or 143, wherein the DNA is mammalian DNA.

145. An insertional nucleic acid comprising an adapter sequence and two mosaic ends, wherein the mosaic ends are recognized by a transposase.

146. The insertional nucleic acid of embodiment 145, wherein the adapter sequence comprises a first primer binding site and a second primer binding site, wherein the first primer binding site and a second primer binding site are adjacent, and the two mosaic ends flank the adapter sequence.

147. The insertional nucleic acid of embodiment 145, wherein the first primer binding site is an inverted sequence of the second primer binding site.

148. The insertional nucleic acid of embodiment 145, wherein the first primer binding site is a palindromic sequence of the second primer binding site.

149. The insertional nucleic acid of embodiment 145, wherein the first primer binding site and the second primer binding site comprise a different sequence.

150. The insertional nucleic acid of embodiment 145, wherein the insertional nucleic acid, from 5' to 3', comprises a first mosaic end, a first primer binding site, a second primer binding site and a second mosaic end.

151. The insertional nucleic acid of embodiment 145, wherein the adapter sequence comprises a transcriptional promoter.

152. A kit comprising:
a. an insertional nucleic acid, wherein the oligonucleotide comprises a mosaic end that is recognized by a transposase; and
b. a transposase.

153. The kit of embodiment 152, wherein the insertional nucleic acid further comprises an adapter sequence.

154. The kit of embodiment 153, wherein the adapter sequence is flanked by a first mosaic end and a second mosaic end.

155. The kit of embodiment 153 or 154, wherein the adapter sequence comprises a primer annealing sequence.

156. The kit of embodiment 155, further comprising a PCR primer that anneals to the primer annealing sequence.
157. The kit of embodiment 156, wherein the PCR primer comprises a tag.
158. The kit of embodiment 157, wherein a first PCR primer comprises a first tag and a second PCR primer comprises a second tag, wherein the first tag and the second tag are different.
159. The kit of embodiment 158, further comprising a plurality of containers.
160. The kit of embodiment 159, wherein the plurality of containers comprises a microwell plate.
161. The kit of embodiment 160, wherein one or more containers of the plurality of containers contains a mixture comprising one or more of the transposase, a portion of the plurality of insertional nucleic acids and the first/second PCR primers.
162. The kit of any one of embodiments 152-161, wherein the transposase is a Tn5 transposase.
163. The kit of any one of embodiments 152-162, further comprising a polymerase.
164. A target nucleic acid molecule comprising a first nucleic acid insert sequence at a first insertion site, a first nucleic acid insert sequence at a second insertion site, and a first nucleic acid sequence at a third insertion site, wherein said first insertion site and said second insertion site are separated by at least 250 bp of nucleic acid molecule sequence that is not first nucleic acid insert sequence.
165. The molecule of embodiment 164, wherein said first nucleic acid insert sequence comprises a left border and a right border bound by a transposase.
166. The molecule of embodiment 165, wherein said left border is bound by a transposase if not covalently linked to flaking sequence on either side of said left border.
167. The molecule of embodiment 165, wherein said right border is bound by a transposase if not covalently linked to flaking sequence on either side of said right border.
168. The molecule of embodiment any one of embodiments 165-167, wherein a transposon directs covalent insertion of a molecule having said first nucleic acid insertion sequence into a nucleic acid molecule to generate a target nucleic acid molecule.
169. The nucleic acid molecule of embodiment 164, wherein said second insertion site and said third insertion site are separated by at least 250 bp of nucleic acid molecule sequence that is not first nucleic acid insert sequence.
170. The nucleic acid molecule of any one of embodiments 164-169, comprising a fourth insertion site, wherein said third insertion site and said fourth insertion site are separated by at least 250 bp of nucleic acid molecule sequence that is not first nucleic acid insert sequence.
171. The nucleic acid molecule of any one of embodiments 164-170, wherein a first insertion site and a second insertion site are separated by at most 2.5 kb.
172. The nucleic acid molecule of any one of claims 164-171, wherein said first nucleic acid insert sequence comprises a first primer binding site.
173. The nucleic acid molecule of any one of embodiments 164-172, wherein said first nucleic acid insert sequence comprises a palindromic sequence such that a first primer binding site is present in a first orientation and a second orientation, said second orientation being antipolar to said first orientation.
174. The nucleic acid molecule of embodiment 173, wherein said first nucleic acid insert sequence comprises a restriction endonuclease cleavage site between said first primer binding site orientation and said second primer binding site orientation.
175. The nucleic acid molecule of any one of embodiments 164-172, wherein said first nucleic acid insert sequence comprises a first primer binding site and a second primer binding site.
176. The molecule of embodiment 175, wherein said first nucleic acid insert sequence comprises a restriction endonuclease cleavage site between said first primer binding site and said second primer binding site.
177. The nucleic acid molecule of any one of embodiments 164-171, wherein said first nucleic acid insert sequence comprises an RNA polymerase promoter.
178. The nucleic acid molecule of embodiment 177, wherein the RNA polymerase promoter is a T7 RNA polymerase promoter.
179. A composition comprising
a) a nucleic acid molecule comprising a first nucleic acid insert sequence at a first insertion site, a first nucleic acid insert sequence at a second insertion site, and a first nucleic acid sequence at a third insertion site, wherein said first insertion site and said second insertion site are separated by at least 250 bp of nucleic acid molecule sequence that is not first nucleic acid insert sequence, and
b) a population of oligonucleotide primers, said population of oligonucleotide primers comprising a plurality of oligonucleotide primers each having sequence reverse complementary to said first nucleic acid insert sequence, and each of said plurality of oligonucleotide primers having a common barcode sequence.
180. The composition of embodiment 179, wherein said common barcode sequence corresponds to said nucleic acid molecule.
181. The composition of embodiment 179, wherein said common barcode sequence corresponds to a container of said composition.
182. The composition of embodiment 179, wherein said common barcode sequence corresponds to at least one container of a plurality of containers of said composition.
183. The composition of any one of embodiments 181-182, wherein said container is a well in a multiwell plate.
184. The composition of any one of embodiments 181-182, wherein said container is a droplet.
185. The composition of any one of embodiments 181-182, wherein said container is a micelle.
186. A method of assigning nucleic acid molecule-specific sequence information, comprising: obtaining a nucleic acid sample comprising a nucleic acid molecule,
inserting an insertion sequence into said nucleic acid molecule at a first site,
amplifying nucleic acid molecule sequence adjacent to said first site, and
sequencing said nucleic acid molecule sequence adjacent to said first site.
187. The method of embodiment 186, wherein inserting said insertion sequence comprises contacting said nucleic acid with a nucleic acid integrase.
188. The method of embodiment 187, wherein said nucleic acid integrase comprises a transposase.
189. The method of any one of embodiments 186-188, comprising inserting an insertion sequence into said nucleic acid molecule at a second site, said second site separated from said first site by about 500 bp to 3 kb.
190. The method of any one of embodiments 186-189, wherein said amplifying comprises contacting said insertion sequence with a first primer that anneals to said first insertion sequence at said first insertion site.

191. The method of embodiment 190, wherein said amplifying comprises contacting said insertion sequence with a second primer that anneals to said first insertion sequence at a second insertion site.

192. The method of any one of embodiments 186-191, comprising segregating said nucleic acid sample among a plurality of partitions prior to said amplifying.

193. The method of any one of embodiments 190-192, wherein said first primer sequence comprises a first tag that corresponds to a subset of said plurality of said partitions.

194. The method of any one of embodiments 190-193, wherein said second primer sequence comprises a second tag that corresponds to a subset of said plurality of said partitions.

195. The method of any one of embodiments 193-194, wherein said first tag and said second tag comprise identical sequence.

196. The method of any one of embodiments 193-194, wherein said first tag and said second tag comprise non-identical sequence.

197. The method of any one of embodiments 186-196, comprising contacting said first insertion sequence to an RNA polymerase prior to said amplifying.

198. The method of embodiment 197, wherein said RNA polymerase is a T7 RNA polymerase.

199. The method of any one of embodiments 197-198, comprising contacting said first insertion sequence with DNase subsequent to contacting to an RNA polymerase.

200. The method of any one of embodiments 197-198, comprising contacting said first insertion sequence with reverse-transcriptase subsequent to contacting to an RNA polymerase.

201. The method of any one of embodiments 197-198, comprising contacting said first insertion sequence with reverse-transcriptase concurrently with contacting said first insertion sequence with RNA polymerase.

202. The method of any one of claims 186-201, wherein said first insertion sequence comprises a restriction endonuclease cleavage site.

203. The method of claim 202, comprising cleaving said first insertion site prior to said amplifying.

204. A method of telomere end mapping, comprising inserting a plurality of nontelomeric extension supporting sequences into a telomeric region, extending nucleic acids from the insertion sites so as span additional insertion sites, sequencing the extension products, and assigning a telomeric order to an extension terminus common to a plurality of extension products.

205. The method of claim 204, wherein the nontelomeric extension supporting sequences comprise primer binding sites.

206. The method of claim 204, wherein the nontelomeric extension supporting sequences comprise RNA polymerase promoters.

207. The method of claim 206, wherein the RNA polymerase promoters are selected from the list of promoters consisting of a T7, T3, T7lac, SP6, pL, CMV, SV40, CaMV35S, araBAD, trp, lac, Ptac, pol I, pol II, pol III, EF1a, PGK1, Ubc, beta actin, CAG, TRE, UAS, Ac5, Polyhedrin, CaMKIIa, ALB, GAL1, GAL10, TEF1, GDS, ADH1, Ubi, H1, and U6.

208. The method of claim 206, wherein the RNA polymerase promoters are selected from the list of promoters consisting of T7, T3, and SP6.

209. The method of claim 206, wherein the RNA polymerase promoters are T7 promoters.

210. The method of claim 204, wherein the nontelomeric extension supporting sequences comprise promoter pairs, directing RNA transcription in opposite directions.

211. The method of claim 204, wherein the extension products comprise RNA molecules.

212. The method of claim 204, wherein the extension products comprise 5' insertion border sequence and 3' telomere sequence.

213. The method of claim 212, wherein some extension products span at least one independent insertion site.

EXAMPLES

Example 1. Insertional Modification for in Silico Sequencing

The following example describes a method for obtaining genomic sequence information while preserving allelic phase origin.

Step 1: Genomic DNA is subjected to Tn5 transposase enzyme and insertional nucleic acids. The genomic DNA is pooled from the genomic DNA of twenty cells. The insertional nucleic acids contain an insertional sequence that encodes two Mosaic End borders and a single RNA promoter sequence as depicted in FIG. 1. Insertional nucleic acids are introduced to the genomic DNA at a frequency of about 500 bp to 2 kb. This produces long continuous genomic DNA molecules with insertional sequences distributed evenly throughout, as exemplified in FIG. 2 and FIG. 3.

Step 2: Long continuous genomic DNA molecules are diluted and distributed into the wells of a 384-well microtiter plate, such that there is a low frequency of similar chromosomes in a single well.

Step 3: Insertion-treated samples are contacted to T7 RNA polymerase and an NTP population under conditions sufficient to allow RNA synthesis directed by the T7 promoter sites.

Step 4: RNA synthesis products are reverse-transcribed to generate a sequencing library.

Step 5: Sequences of PCR products containing the same barcode are arranged in order according to overlapping sequences to produce a whole genome sequence.

Example 2. Cleavage Before Amplification

The following example describes a method for obtaining genomic sequence information while preserving allelic phase origin.

Step 1: Genomic DNA is subjected to Tn5 transposase enzyme and insertional nucleic acids. The genomic DNA is pooled from the genomic DNA of twenty cells, in order to account for intercellular genomic variation. The insertional nucleic acids contain an insertional sequence that encodes two adapter sequences. The first adapter sequence is the inverse sequence of the second adapter sequence. The insertional sequence contains two mosaic ends, which flank the two adapter sequences as depicted in FIG. 4. The insertional sequence also contains a restriction endonuclease cleavage site between the first adapter sequence and the second adapter sequence as depicted in FIG. 4. Insertional nucleic acids are introduced to the genomic DNA at a frequency of about 500 bp to 2 kb. This produces long continuous genomic DNA molecules with insertional sequences distributed evenly throughout, as exemplified in FIG. 3.

Step 2: Long continuous genomic DNA molecules are diluted and distributed into the wells of a 384-well microtiter plate, such that there is a low frequency of similar chromosomes in a single well.

Step 3: The restriction endonuclease is added cleaving the long continuous genomic DNA molecule with insertional sequences into many fragments of genomic DNA flanked by mosaic ends and a first adapter sequence a one end and a second adapter sequence a the other end, as depicted in FIG. 4.

Step 4: The fragments of genomic DNA are PCR amplified in each well with a pair of primers, the first of which anneals to the first adapter sequence and the second of which anneals to the second adapter sequence, priming in opposite directions to amplify the genomic DNA fragments, as depicted in FIG. 4. Each primer of the pair of primers also contains a well-specific barcode sequence. This produces multiple PCR products in each well with a well-specific barcode.

Step 5: All PCR products are pooled and sequenced using a Next Generation automated sequencing machine.

Step 6: Sequences of PCR products containing the same barcode are arranged in order according to overlapping sequences to produce a whole genome sequence.

Example 3. Single Target Nucleic Acid Amplification

The following example describes a method for obtaining genomic sequence information while preserving allelic phase origin.

Step 1: Genomic DNA is subjected to Tn5 transposase enzyme treatment loaded using insertional nucleic acids. The genomic DNA is pooled from the genomic DNA of a single cell. The insertional nucleic acids contain an insertional sequence that encodes a T7 RNA promoter. The insertional sequence also contains two mosaic ends, which flank the promoter as depicted in FIG. 1. Insertional nucleic acids are introduced to the genomic DNA at a frequency of about 500 bp to 2 kb. This produces long continuous genomic DNA molecules with insertional sequences distributed evenly throughout, as exemplified in FIG. 3.

Step 2: Long continuous genomic DNA molecules are diluted and distributed into droplets such that there is only a single long continuous genomic DNA molecule per droplet.

Step 3: Each long continuous genomic DNA molecule, in its individual droplet, is amplified by contacting to T7 RNA polymerase in the presence of reagent sufficient for RNA transcription. This produces 1000× amplification of the single cell genomic sample, generating a library where library constituents are directly derived from the sample template rather than from amplified intermediate templates.

Example 4. Reverse Transcription of Multi-Insert Nucleic Acids

The following example describes a method for obtaining genomic sequence information while preserving allelic phase origin.

Step 1: Genomic DNA is subjected to Tn5 transposase enzyme and insertional nucleic acids. The genomic DNA is pooled from the genomic DNA of twenty cells, in order to account for intercellular genomic variation. The insertional nucleic acids contain an insertional sequence that encodes a T7 primer annealing sequence. The insertional sequence also contains two mosaic ends, which flank the T7 primer annealing sequence. Insertional nucleic acids are introduced to the genomic DNA at a frequency of about 500 bp to 1 kb. This produces long continuous genomic DNA molecules with insertional sequences distributed evenly throughout, as exemplified in FIG. 3.

Step 2: Long continuous genomic DNA molecules are diluted and distributed into droplets such that there is only a single long continuous genomic DNA molecule per droplet.

Step 3: T7 polymerase and superscript 2 reverse transcriptase (RT) are added along with random primers which contain a well-specific barcode sequence. The T7 polymerase produces linear RNA copies of the genomic DNA between the insertional nucleic acids, and the RT will make random primed DNA copies of the RNA molecules.

Step 4: these template droplets are merged with droplets containing the labeled oligos Step 5: T7 polymerase amplifies from the T7 promoter sites making RNA copies Step 6: superscript II reverse transcribes the RNA copies into cDNA while incorporating a ddNTP biotin which fragments the cDNA and introduces a 3' terminal biotin. Molecules are now within a desired length and have an affinity molecule (biotin) at the 3' terminal end.

Step 7: Captured PCR products are sequenced using a Next Generation automated sequencing machine.

Sequences of PCR products containing the same barcode are arranged in order according to overlapping sequences to produce a whole genome sequence.

Example 5: Insertion of T7 Promoter Sequences into Genomic DNA Using a Transposase (Tn5)

Conventional methods for whole genome amplification are based on random-primed PCR, Phi29 (or other strand displacing) polymerase-based multiple displacement amplification, or a combination of the two. While these methods are highly efficient at amplifying even sub genomic quantities of DNA, they have problems including nucleotide preferences of the polymerase, error propagation from DNA amplification in which copies of DNA are template for new copies, and polymerase extension artifacts that generate spurious tandem repeats and inversions during the amplification. Consequently, attempts to use these conventional methods for amplification of sub genomic fractions of DNA for the purposes of phasing and de novo assembly applications have not been successful. Methods disclosed herein utilize linear amplification through in vitro transcription (IVT) from T7 RNA promoter sequences inserted into genomic DNA at high density. The T7 transcription system is ideal for IVT amplification due to the strength of the promoter sequence and the high processivity of the polymerase resulting in a high yield of long contiguous transcripts initiated by the promoter sequence. The method disclosed herein inserts the T7 promoter into genomic DNA at high frequency using a transposase enzyme, Tn5 such as EZ-Tn5. The Tn5 transposition system of this method inserts Tn5 transposable elements with T7 promoter sequences throughout the human genome at an average of one insertion per 500-2000 bp.

The EZ-Tn5 transposon is customized to insert T7 phage promoter sequence within the transposon required for transcription initiation by T7 RNA polymerase and an 8 bp restriction site for an enzyme that cuts less frequently in the human genome to create larger sub genomic pieces of the genome (FIG. 13). The transposon ends contain inverted repeats to which the Tn5 transposase binds and which are essential for successful transposition.

In vitro transposition requires a minimum of four components: a transposase, a donor (transposon), a target (DNA, genomic or otherwise) and magnesium ions. In their presence, the Tn5 transposon is inserted randomly into genomic DNA creating a 9-bp duplication on either side of each insertion. There is also a gap produced by transposon insertion on one of the DNA strands (opposite the 9 base pair duplications) that is filled and ligated prior to initiation of in vitro transcription. The gap is in the template strand, i.e., the strand that is used as template for transcription from the T7 promoter. Gap repair enzymes (T4 DNA polymerase and ligase), are used to close the transposase induced gaps as well as any pre-existing nicks in the genomic DNA.

Insertions are generated randomly throughout the genome at a frequency of 500-2000 bp. Since T7 RNA polymerase can generate transcripts in excess of 9 to 10 kb, the entire genome is transcribed from one or more T7 promoters. The insertion frequency is controlled by modulating the ratio of transposon to genomic DNA or by varying the length of the transposition reaction. The frequency of transposition is assessed by several different methods such as restriction enzyme digestion directed to the restriction site designed into the transposon, digestion with an endonuclease, such as 51 nuclease to detect nicks and gaps created by transposition events, and direct sequencing of transposed genomic DNA samples. After gap repair is successfully completed, the complete Tn5 insertion profile is evaluated by creating a library and sequencing target DNA and analyzing the frequency and distribution of insertion events in NGS reads.

Example 6: IVT Amplification of a DNA Sequence Containing a T7 Promoter and Conversion into cDNA Containing Molecular Barcodes A model system is used to optimize the in vitro transcription reaction performed concomitantly with the reverse transcription reaction. The model system uses an RNA polymerase promoter element containing a linearized plasmid, pTRI-Xef, generating an RNA transcript approximately 1.9 Kb in length. The plasmid contains three different promoter elements; T7, T3, and SP6, so all three respective RNA polymerases are tested. The reverse transcription reaction is done testing several different reverse transcriptases, such as, Superscript III or IV (Thermo Fisher), ThermoScript (Thermo Fisher), HIV reverse transcriptase (CHIMERx), or RocketScript (Bioneer). The reaction includes: standard dNTPs, small percentage of biotin-dCTP and biotin-dUTP to incorporate the capture moiety, and a small fraction of ddNTPs to control the distribution size of the DNA products. Reverse transcription reactions are optimized for the best biotin-dNTP and ddNTP concentrations to work with the standard dNTPs for the best yields and the best product size distributions, without affecting the sequencing quality of the data. Buffer components are also optimized, e.g., pH, salt concentrations, as well as other additives, like spermine or DTT. The in vitro transcription reactions and the reverse transcription are done in a decoupled successive format, isolating the RNA from the in vitro transcription reaction (with ethanol precipitation or column based cleanup methods) before proceeding to reverse transcription. The best performing reactions in the decoupled format are chosen to move on into a coupled format, where both reactions occur concomitantly. Lastly, in either the decoupled or coupled format the reverse transcribed material are taken into the second-strand synthesis reaction and PCR.

In the decoupled format discussed above; for the in vitro transcription reaction, RNA yields and product size distribution are used to assess reaction efficiency. In either the decoupled or coupled format, the reverse transcription reaction is assessed based on the yield, product size distribution, and sequencing data of the final PCR product generated after second-strand synthesis. The yields are measured by UV-vis and Fluorescent based assays (Qubit, ThermoFisher). Product size distributions are measured by agarose gel or Bioanalyzer 2100 instrument (Agilent) using either the RNA or dsDNA chip-based assays. Sequencing is done on Illumina MiSeq or NextSeq instruments and reads are aligned to confirm the coverage of the linearized plasmid, pTRI-Xef. Yields assess how efficiently the reactions are proceeding. For in vitro transcription, typical yields generated are around 1000-2000 fold amplification, thus, if 1 ng DNA template input is used, roughly 1 μg to 2 μg of RNA product is expected. For the reverse transcription reaction, yields of the final PCR product generated indicate how well this reaction is proceeding. For example, for the three RNA-RLP experiments the input of RNA used was roughly 5 ng after ribosomal depletion. This generated approximately 200 ng of final product after PCR amplification that was used for sequencing. Similar yields are expected with the same amount of RNA input. Product sizes for the in vitro transcription reaction, based on the sequence of the pTRI-Xef plasmid, are 1.92 Kb, 1.89 Kb, and 1.86 Kb, for the SP6, T7, and T3 RNA polymerases, respectively. Product size distribution of the reverse transcription is assessed from the final PCR product sizes. For the RNA-RLP, the final PCR product size distribution ranged from approximately 200-600 bp. Sequencing results match that of the plasmid and uniformity of coverage and sequencing fidelity is assessed. Successful completion of this optimization is demonstrated by the ability to generate a sequencing library from 1 ng of input DNA template, all the way through (in the coupled format for the in vitro transcription and reverse transcription) to approximately 200 ng final PCR products in the size range of 200-600 bp after 12 cycles of PCR.

Example 7: Sequencing of Human Genomic DNA Using the Isothermal "One-Pot" Reaction The method herein uses the genomic DNA sample with T7 promoter sequences inserted at high frequency using a transposase generated for a substrate for the optimized one-pot IVT/cDNA synthesis reaction. An aliquot of genomic DNA, for example 20 ng, represents approximately 6000 haploid genomic copies that is treated with a transposase and transposon containing the T7 promoter sequence. An aliquot of this T7-transposed genomic DNA is diluted in a Raindance micro-droplet system such that each droplet contains only a tiny fraction of one haploid genome. Inside the droplet, the T7 IVT reaction amplifies the genomic sequence while the cDNA reaction copies the RNA into cDNA containing molecular barcodes and the Illumina Rd1 adapter. After the amplification/cDNA synthesis reaction is complete, the droplets are destabilized and the biotinylated cDNA molecules are captured with streptavidin coated magnetic beads. Next, second strand synthesis is performed which adds the Rd2 adapter sequence, followed by PCR and sequencing. The effect of droplets is mimicked by performing multiple reactions with sub genomic quantities in micro tubes and sequencing these to high coverage. Standard de novo assembly tools (ABSySS, Velvet, String Graph Assembly) are used to assemble long molecules. Analysis of this data allows determination of the length of contiguous molecules in the reaction as well as the uniformity of coverage for each molecule sequenced.

Genomic DNA with T7 promoter sequences inserted at high frequency (every 500-2000 bps) is generated as discussed above. Between 0.1 and 1 pg of the T7 transposed genomic DNA is used as substrate for the IVT/cDNA isothermal amplification reaction discussed above. Multiple replicate reactions are performed with sub-genomic quantities of input DNA, individually barcoded during library preparation, and sequenced to an average depth of 20× or greater. A target of 2M reads for each subgenomic fraction using 2×75 bp MiSeq sequencing is used to optimize use of assembly algorithms (ABSySS, Velvet, SOAPdenovo, String Graph Assembly) and metrics such as % reads assembled, # of contigs, switch error rate, and N50 molecule size is used for optimization and quality control. Coverage per molecule and uniformity of coverage within a molecule is also assessed.

Contiguous assembly of molecules is performed with an average length of >20,000 bp (N50=20 kb) and ranging from 10,000 to greater than 100,000 bps. On average, 10 s to 100 s of non-overlapping contiguous synthetic long reads for each aliquot of sub-genomic DNA input result. The number of individual molecules identified by de novo assembly multiplied by the average length of each molecule correlates with the input amount of T7-mutagenized gDNA input into each reaction. With the desired 20× average sequencing depth for each molecule, greater than 90% of each molecule is covered with a sequencer read depth greater than 4× (0.2× mean coverage per molecule) without gaps. The data generated enables determination the overall efficiency of the reaction. In particular, the amount of input material into a massively parallel droplet device (e.g., RainDance Technologies) required for complete de novo assembly using a reasonable amount of short read sequencer capacity (<200 Gbp of raw sequence) is determined.

Example 8: Telomere End Mapping

Insertion fragments having a T7 promoter are inserted into a eukaryotic genomic sample at a density of about one insert every 2 kb. The sample is subjected to T7 RNA polymerase activity under conditions supporting transcription. RNA intermediates are synthesized having an average length of about 10 kb.

Intermediates are reverse transcribed and the subsequent library is synthesized. It is observed that a plurality of library constituents comprise telomeric sequence and share a common termination site. Many of the molecules also share common insertion promoter initiation sites, indicating that they arise from a common promoter. It is also observed that some of the molecules harbor independently derived single-position point mutations, indicating that the molecules are independently derived rather than being clonal amplicons. Populations of molecules sharing distinct separate initiation sites are observed, and the longer populations are seen to comprise insertion sites that are consistent with the initiation sites of the shorter populations. A common extreme 3' end is seen across these populations. This 3' end is inferred to be a telomeric DNA endpoint.

Further extension products overlapping in insertion pattern with the 5' end of the telomere-terminal extension products are obtained, and the entire telomeric region is assembled, having an insertion pattern that facilitates accurate determination of the full telomeric sequence and length.

Additional telomeric sequence is obtained that does not have the corresponding insertion pattern. This sequence is assigned to a separate telomere in the genomic sample.

The sample is found to harbor a telomeric length consistent with pre-cancerous telomere extension.

Example 9: Amplification of a Sub Genomic Sample from a Single Cell

A genomic sample from a single cell is obtained and aliquotted into a plurality of fractions. The fractions are not suitable for downstream applications without amplification.

A fraction is contacted to an insertion fragment comprising an RNA promoter and a transposase activity. Insertions are introduced into the genomic sample at a frequency of about 1 insertion per 2 kb.

The inserted sample is subjected to T7 RNA polymerase transcription to form RNA transcripts directed by the insertion promoters.

The sample is amplified 10000× as RNA transcripts. Each RNA transcript is derived directly from the genomic sample. RNA transcripts are converted into a sequencing library and sequenced.

It is determined that the library does not contain a substantial proportion of clonally amplified library constituents. Point mutations, identified as rare single base mutations in the library, are observed at a base frequency. Point mutations are also observed that occur at a frequency of about 50% relative to one another. The point mutations occurring at a frequency of from 20% to 80% are inferred to represent allelic variation in the diploid sample. Rare point mutations are inferred to comprise errors in library generation, and are easily identified and removed from the sequence assembly.

It is determined that at least 90% of the starting material is amplified in the library. It is also determined that, of the 90% of the ample represented in the library, about 85% of the amplified sequence is present within a factor of four of the abundance of the median transcript. That is, the amplification is largely uniform rather than being skewed by the selective amplification of a subset of the sub genomic fraction.

Example 10: Heterogeneous Sample Amplification

A sample comprising 10 diploid genomes is subjected to amplification. Some mutations are found to occur at a frequency of about 5% in the amplified genomic sequence. These mutations are inferred to represent an allele of a single heterozygous individual in the heterogeneous sample.

Other mutations are found to occur at a frequency of about 1/1000. These mutations are inferred to have occurred in the library synthesis process. As the library synthesis process involves synthesizing RNA intermediates directly from the genomic sample template rather than from amplified template intermediates, errors in RNA intermediate synthesis do not proliferate though, for example, PCR amplification bias. These mutations remain independently derived and rare, and are easily identified in even a highly heterogeneous bulked genomic sample.

Example 11: Translocation Detection

A tumor sample is extracted, genomic DNA obtained and a library is generated using a primer-extension based method. An intermediate primer extension product anneals to the sample at a random position during synthesis, and further extension is observed. The extension results in a chimeric molecule that is indistinguishable from a rare translocation event in the tumor nucleic acid sample. The extension product serves as a template for further rounds of amplification, resulting in multiple copies of the chimeric molecule being generated.

The chimeric molecule is indistinguishable from a translocation event, demonstrating a challenge with using primer extension-based library generation.

Example 12: Translocation Detection

A tumor sample is extracted, genomic DNA obtained and a library is generated using an RNA promoter directed synthesis of RNA intermediates, each of which is derived directly from a sample template. No RNA intermediates serve as templates for early round PCR reactions, and the RNA intermediate 3' ends do not prime further extension.

A sequence is observed indicative of a translocation. The event is observed in about 1000 overlapping reads of a 1000× amplified library. The translocation is inferred to represent an event in the genomic sample that occurred in a small subset of the tumor genomic DNA.

Example 13: Library Generation

A library was generated from 100 pg of nucleic acids, derived from 10 human cells. 90% of the reads from the library mapped to previously generated human scaffold sequences. The library demonstrated a 40% GC content, indicating that the library did not suffer significant GC bias. The library comprised a diversity of 40-50 million unique molecules. 9 million reads were generated from the library, amounting to a mean coverage of 1.4× of the human scaffold.

As indicated in FIG. 16, DNA library constituents display lengths ranging from 121 bp to well over 1 kb, having a peak about 272 bp. At an insertion density of about 500 pb to 1 kb or more, one expects complete coverage of the sample.

As indicated in FIG. 17, the % GC for a sequencing library reverse-transcribed from the RNA intermediate library mimics that of the underlying human genomic sample. This indicates that the library generation is unbiased relative to sample GC percentage, a beneficial feature not share by most library amplification approaches.

What is claim is:

1. A method of generating a plurality of multi-insert nucleic acids, the method comprising: combining
    a) an insertional nucleic acid comprising an adapter sequence and an RNA promoter sequence that is flanked by nucleic acid integrase recognition sequences;
    b) a plurality of target nucleic acids; and
    c) a nucleic acid integrase,
    wherein the nucleic acid integrase
        i) cleaves one or more of the plurality of target nucleic acids to produce one or more recombination sites,
        ii) recognizes the nucleic acid integrase recognition sequences;
        iii) inserts the insertional nucleic acid into the one or more recombination sites to generate the plurality of multi-insert nucleic acids
    d) providing a nucleic acid polymerase that binds to the RNA promoter sequence; and
    e) amplifying the plurality of multi-insert nucleic acids or portions thereof, thereby producing a plurality of amplified nucleic acids,
    wherein both strands of the plurality of multi-insert nucleic acids are amplified, and
    wherein the plurality of target nucleic acids is obtained from a genomic sample from a single cell.

2. The method of claim 1, wherein the adapter sequence comprises an RNA promoter sequence.

3. The method of claim 1, wherein the nucleic acid integrase is a transposase.

4. The method of claim 1, further comprising adding a PCR primer to the plurality multi-insert nucleic acids, wherein the PCR primer anneals to the insertional nucleic acid or a portion thereof, and amplifying one or more of the plurality of multi-insert nucleic acids or a portion thereof.

5. The method of claim 1, wherein the nucleic acid polymerase is a phi29 DNA polymerase and the insertional nucleic acid comprises random primer annealing sites.

6. The method of claim 1, wherein the nucleic acid polymerase is T7 polymerase and the insertional nucleic acid comprises a T7 primer annealing site.

7. The method of claim 6, further comprising introducing a reverse transcriptase and random primers.

8. The method of claim 1, further comprising cleaving the insertional nucleic acid of the plurality of multi-insert nucleic acids to produce a plurality of multi-insert nucleic acid fragments, wherein each multi-insert nucleic acid fragment is flanked by the first portion of the insertional nucleic acid and the second portion of the insertional nucleic acid.

9. The method of claim 1, further comprising sequencing plurality of multi-insert nucleic acids.

10. The method of claim 1, wherein at least 90% of the target nucleic acids are amplified at least 1000×.

* * * * *